(12) United States Patent
Lazarus et al.

(10) Patent No.: US 11,284,934 B2
(45) Date of Patent: Mar. 29, 2022

(54) METHODS FOR TREATING SLEEP DISORDERS IN PATIENTS VIA RENAL NEUROMODULATION

(71) Applicant: Medtronic Ardian Luxembourg S.a.r.l., Luxembourg (LU)

(72) Inventors: Gabriel Lazarus, Santa Rosa, CA (US); Douglas Hettrick, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 688 days.

(21) Appl. No.: 16/027,149

(22) Filed: Jul. 3, 2018

(65) Prior Publication Data

US 2019/0008577 A1   Jan. 10, 2019

Related U.S. Application Data

(60) Provisional application No. 62/570,597, filed on Oct. 10, 2017, provisional application No. 62/570,603, (Continued)

(51) Int. Cl.
*A61B 18/14* (2006.01)
*A61B 18/02* (2006.01)
(Continued)

(52) U.S. Cl.
CPC ............ *A61B 18/14* (2013.01); *A61B 5/25* (2021.01); *A61B 5/4815* (2013.01);
(Continued)

(58) Field of Classification Search
CPC ..... A61B 18/14; A61B 18/02; A61B 18/1492; A61B 5/25; A61B 5/4815; A61B 5/4818;
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| WO | 2013/134733 | 9/2013 |
| WO | 2014/150595 | 9/2014 |

(Continued)

OTHER PUBLICATIONS

Allen, E.V., Sympathectomy for essential hypertension, Circulation, 1952, 6:131-140.

(Continued)

*Primary Examiner* — Michael F Peffley
*Assistant Examiner* — Bo Ouyang
(74) *Attorney, Agent, or Firm* — Shumaker & Sieffert, P.A.

(57) ABSTRACT

Methods for treating sleep disorders and for reducing a risk associated with developing a sleep disorder in patients via therapeutic renal neuromodulation and associated systems are disclosed herein. Sympathetic nerve activity can contribute to several cellular and physiological conditions associated with sleep disorders as well as an increased risk of developing a sleep disorder. One aspect of the present technology is directed to methods for improving a patient's calculated risk score corresponding to a sleep disorder status in the patient. Other aspects are directed to reducing a likelihood of developing a sleep disorder in patients presenting one or more sleep disorder risk factors. Renal sympathetic nerve activity can be attenuated to improve a patient's sleep disorder status or risk of developing a sleep disorder. The attenuation can be achieved, for example, using an intravascularly positioned catheter carrying a therapeutic assembly configured to use, e.g., electrically-induced, (Continued)

thermally-induced, and/or chemically-induced approaches to modulate the renal sympathetic nerve.

18 Claims, 11 Drawing Sheets

Related U.S. Application Data filed on Oct. 10, 2017, provisional application No. 62/528,876, filed on Jul. 5, 2017, provisional application No. 62/528,867, filed on Jul. 5, 2017.

(51) Int. Cl.
*A61B 5/00* (2006.01)
*G16H 20/30* (2018.01)
*A61B 5/25* (2021.01)
*A61N 1/05* (2006.01)
*A61N 1/36* (2006.01)
*A61B 18/00* (2006.01)
*A61B 5/08* (2006.01)
*A61B 18/24* (2006.01)
*A61N 7/02* (2006.01)
*G16H 50/30* (2018.01)

(52) U.S. Cl.
CPC ............ *A61B 5/4818* (2013.01); *A61B 18/02* (2013.01); *A61B 18/1492* (2013.01); *A61N 1/0551* (2013.01); *A61N 1/36096* (2013.01); *G16H 20/30* (2018.01); *A61B 5/082* (2013.01); *A61B 18/24* (2013.01); *A61B 2018/00404* (2013.01); *A61B 2018/00434* (2013.01); *A61B 2018/00511* (2013.01); *A61B 2018/00577* (2013.01); *A61B 2018/00589* (2013.01); *A61B 2018/0212* (2013.01); *A61N 1/36135* (2013.01); *A61N 7/022* (2013.01); *G16H 50/30* (2018.01)

(58) Field of Classification Search
CPC A61B 2018/00404; A61B 2018/00434; A61B 2018/00511; A61B 2018/00577
See application file for complete search history.

(56) References Cited

U.S. PATENT DOCUMENTS

| | | | |
|---|---|---|---|
| 4,764,504 A | 8/1988 | Johnson et al. |
| 4,976,711 A | 12/1990 | Parins et al. |
| 5,300,068 A | 4/1994 | Rosar et al. |
| 5,358,514 A | 10/1994 | Schulman et al. |
| 5,423,744 A | 6/1995 | Gencheff et al. |
| 5,571,147 A | 11/1996 | Sluijter et al. |
| 5,626,576 A | 5/1997 | Janssen |
| 5,700,282 A | 12/1997 | Zabara |
| 5,707,400 A | 1/1998 | Terry, Jr. et al. |
| 5,865,787 A | 2/1999 | Shapland |
| 5,944,710 A | 8/1999 | Dev et al. |
| 5,983,141 A | 11/1999 | Sluijter et al. |
| 6,004,269 A | 12/1999 | Crowley et al. |
| 6,009,877 A | 1/2000 | Edwards |
| 6,066,134 A | 5/2000 | Eggers et al. |
| 6,099,524 A | 8/2000 | Lipson et al. |
| 6,117,101 A | 9/2000 | Diederich et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,405,732 B1 | 6/2002 | Edwards et al. |
| 6,506,189 B1 | 1/2003 | Rittman et al. |
| 6,514,226 B1 | 2/2003 | Levin et al. |
| 6,522,926 B1 | 2/2003 | Kieval et al. |
| 6,562,034 B2 | 5/2003 | Edwards et al. |
| 6,635,054 B2 | 10/2003 | Fjield et al. |
| 6,685,648 B2 | 2/2004 | Flaherty et al. |
| 6,736,835 B2 | 5/2004 | Pellegrino et al. |
| 6,845,267 B2 | 1/2005 | Harrison et al. |
| 6,850,801 B2 | 2/2005 | Kieval et al. |
| 6,885,888 B2 | 4/2005 | Rezai |
| 6,893,436 B2 | 5/2005 | Woodard et al. |
| 6,978,174 B2 | 12/2005 | Gelfand et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,520 B2 | 4/2012 | Demarais et al. |
| 8,175,711 B2 | 5/2012 | Demarais et al. |
| 8,347,891 B2 | 1/2013 | Demarais et al. |
| 8,888,773 B2 | 11/2014 | Chang et al. |
| 9,060,755 B2 | 6/2015 | Buckley et al. |
| 9,084,610 B2 | 7/2015 | Goshgarian et al. |
| 2003/0060858 A1 | 3/2003 | Kieval et al. |
| 2005/0228460 A1 | 10/2005 | Levin et al. |
| 2006/0099594 A1* | 5/2006 | Yamada ............ C07K 14/7158 435/6.11 |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0207758 A1* | 8/2011 | Sobotka ............ A61N 1/36057 514/272 |
| 2011/0208175 A1 | 8/2011 | Sobotka et al. |
| 2012/0116382 A1 | 5/2012 | Ku et al. |
| 2012/0130289 A1 | 5/2012 | Demarais et al. |
| 2012/0130345 A1 | 5/2012 | Levin et al. |
| 2012/0150267 A1 | 6/2012 | Buckley et al. |
| 2012/0172837 A1 | 6/2012 | Demarais et al. |
| 2014/0088575 A1* | 3/2014 | Loeb .................... A61B 18/24 606/7 |
| 2014/0276718 A1 | 9/2014 | Turovskiy et al. |
| 2015/0223877 A1* | 8/2015 | Behar .................... A61B 18/04 600/1 |
| 2016/0058503 A1 | 3/2016 | Tunev et al. |

FOREIGN PATENT DOCUMENTS

| | | |
|---|---|---|
| WO | 2015/113027 | 7/2015 |
| WO | 2015/143372 | 9/2015 |
| WO | 2016/033543 | 3/2016 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain

(56) References Cited

OTHER PUBLICATIONS

Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H et al., "The Effect of Renal Denervation on Patients Suffering From Nephritis," Feb. 27, 1935;443-458.
Page, I.H et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based Yenal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Brown et al., "Cardiovascular abnormalities in patients with major depressive disorder autonomic mechanisms and implications for treatment." CNS Drugs, 2009, vol. 23(7), pp. 583-602 (Abstract only), doi: 10.2165/00023210-200923070-00004, [accessed online Mar. 10, 2017].
Buckley et al., "Review: On the Interactions of the Hypothalamic-Pituitary-Adrenal (HPA) Axis and Sleep: Normal HPA Axis Activity and Circadian Rhythm, Exemplary Sleep Disorders," The Journal of Clinical Endocrinology & Metabolism, May 2005, vol. 90(5), pp. 3106-3114.
Buysse et al., "The Pittsburgh Sleep Quality Index: A New Instrument for Psychiatric Practice and Research," Psychiatry Research (Elsevier), Nov. 1988, vol. 28, pp. 193-213.
Chung et al., "Sleep Disorders and Increased Risk of Subsequent Acute Coronary Syndrome in Individuals without Sleep Apnea: A Nationwide Population-Based Cohort Study," Sleep, Jun. 2013, vol. 36(12):1963-1968A, 7 pages.
Cai et al., "Sparse whole genome sequencing identifies two loci for major depressive disorder," Nature, Jul. 30, 2015, vol. 523(7562), doi:10.1038/nature14659, 25 pages.
Dorr et al., "Beneficial effects of renal sympathetic denervation on cardiovascular inflammation and remodeling in essential hypertension," Clin Res Cardiol., published online Oct. 2014 (2015), vol. 104, pp. 175-184.
Enman et al., "Targeting the neuropeptide Y system in stress-related psychiatric disorders," Neurobiology of Stress 1 (Elsevier), published online: Oct. 2014 (2015), pp. 33-43.
Fitzgerald et al.,"Effects of dipping and psychological traits on morning surge in blood pressure in healthy people," Journal of Human Hypertension, published online: Apr. 2011 (2012), vol. 26, pp. 228-235.
Halaris, "Inflammation-Associated Co-morbidity Between Depression and Cardiovascular Disease," Curr Topics Behav Neurosci, 2016, 26 pages, DOI 10.1007/7854_2016_28.
Huang et al.,"Nonapnea Sleep Disorders and Incident Chronic Kidney Disease: A Population-Based Retrospective Cohort Study," Medicine, Jan. 2015, vol. 94(4), pp. 1-7, DOI: 10.1097/MD.0000000000000429.
Hyde et al., "Identification of 15 genetic loci associated with risk of major depression in individuals of European descent," Nat Genet. Author Manuscript, Sep. 2016, vol. 48(9), 23 pages, doi:10.1038/ng.3623.
Irwin et al., "Sleep Disturbance, Sleep Duration, and Inflammation: A Systematic Review and Meta-Analysis of Cohort Studies and Experimental Sleep Deprivation," Biol Psychiatry Author Manuscript, Jul. 2016, vol. 80(1), 25 pages, doi:10.1016/j.biopsych.2015.05.014.
Jedema et al., "Corticotropin-Releasing Hormone Directly Activates Noradrenergic Neurons of the Locus Ceruleus Recorded In Vitro," The Journal of Neuroscience, Oct. 27, 2004, vol. 24(43), pp. 9703-9713.
Kario et al., "Nocturnal Blood Pressure Surge Behind Morning Surge in Obstructive Sleep Apnea Syndrome: Another Phenotype of Systemic Hemodynamic Atherothrombotic Syndrome," The Journal of Clinical Hypertension, Sep. 2015, vol. 17(9), pp. 682-685.
Mark R. de Jong et al. "Renal Nerve Stimulation-Induced Blood Pressure Changes Predict Ambulatory Blood Pressure Response After Renal Denervation" Mar. 9, 2016, Hypertension 2016; 68:707-714.
Kario et al.,"Effect of Catheter-Based Renal Denervation on Morning and Nocturnal Blood Pressure: Insights From Symplicity HTN-3 and SYMPLICITY HTN-Japan," Hypertension (Clinical Trials), Dec. 2015, vol. 66, pp. 1130-1137 and Supplementary Appendix. [published online Oct. 5, 2015; doi: 10.1161/HYPERTENSIONAHA.115.06260].
Lanfranchi et al., "Nocturnal Blood Pressure in Chronic Insomnia: Nighttime Blood Pressure in Normotensive Subjects With Chronic Insomnia: Implications for Cardiovascular Risk," SLEEP, Feb. 2009, vol. 32(6), pp. 760-766.
Mahan et al.,"Fear conditioning, synaptic plasticity and the amygdala: implications for posttraumatic stress disorder," Trends in Neurosciences, Jan. 2012, vol. 35(1), pp. 24-35.
Menke et al., "Genetic variation in FKBP5 associated with the extent of stress hormone dysregulation in major depression," Genes, Brain and Behavior, 2013, vol. 12, pp. 289-296.

(56) References Cited

OTHER PUBLICATIONS

Miller et al., "Inflammation and Its Discontents: The Role of Cytokines in the Pathophysiology of Major Depression," Biol Psychiatry, 2009, vol. 65, pp. 732-741.
Pitman et al., "Biological Studies of Posttraumatic Stress Disorder," Nat Rev Neurosci., Nov. 2012, vol. 13(11), pp. 769-787.
Rizzi et al., "May diabetes patients have trouble sleeping despite not having obesity?" Journal of Clinical & Translational Endocrinology 1 (Elsevier), Mar. 2014, pp. 44-48.
Sah et al., "Neuropeptide Y and posttraumatic stress disorder," Mol Psychiatry, Jun. 2013, vol. 18(6), pp. 646-655, doi:10.1038/mp.2012.101.
Sherin et al., "Post-traumatic stress disorder: the neurobiological impact of psychological trauma," Dialogues in Clinical Neuroscience, 2011, vol. 13(3), pp. 263-278.
Spijker et al., "Glucocorticoid Sensitivity in Mood Disorders," Neuroendocrinology Published online: Nov. 8, 2011 (2012), vol. 95, pp. 179-186.
Wang et al., "Glucocorticoid receptors in the locus coeruleus mediate sleep disorders caused by repeated corticosterone treatment," Scientific Reports, Mar. 24, 2015, vol. 5:9442, 11 pages, DOI: 10.1038/srep09442.
Alvares et al., "Autonomic nervous system dysfunction in psychiatric disorders and the impact of psychotropic medications: a systematic review and meta-analysis," J Psychiatry Neurosci, 2016 (early publication: Oct. 8, 2015), 41 (2), pp. 89-104.
Anda et al., "Depressed Affect, Hopelessness, and the Risk of Ischemic Heart Disease in a Cohort of U.S. Adults," Epidemiology, Jul. 1993, vol. 4(4), pp. 285-294.
Baroni et al., "Effects of Renal Sympathetic Denervation on Arterial Stiffness and Blood Pressure Control in Resistant Hypertensive Patients: A Single Centre Prospective Study." High Blood Press Cardiovasc. Prev., Dec. 2015, 22(4), pp. 411-416.
Bearden et al., "Altered hippocampal morphology in unmedicated patients with major depressive illness," ASN Neuro, Oct. 20, 2009, vol. 1 (4):art:e00020, doi: 10.1042/AN20090026, pp. 265-273.
Bech et al., "Psychometric evaluation of the Major Depression Inventory (MDI) as depression severity scale using the LEAD (Longitudinal Expert Assessment of All Data) as index of validity," BMC Psychiatry, Aug. 2015, vol. 15(190), 7 pages.
Bissette et al., "Elevated Concentrations of CRF in the Locus Coeruleus of Depressed Subjects," Neuropsychopharmacology, Jul. 2003, vol. 28, pp. 1328-1335.
Boscarino et al., "The New York PTSD Risk Score for Assessment of Psychological Trauma: Male and Female Versions," Psychiatry Res., Dec. 30, 2012, 200(2-3): 827-834, 18 pages.
Brandt et al., "Effects of Renal Sympathetic Denervation on Arterial Stiffness and Central Hemodynamics in Patients With Resistant Hypertension," Journal of the American College of Cardiology, Nov. 2012, vol. 60, No. 19, pp. 1956-1965.
Delahanty, "Toward the Predeployment Detection of Risk for PTSD," Am. J. Psychiatry, Jan. 2011, 168:1, pp. 9-11.
Dhar et al., "Depression and the Link with Cardiovascular Disease," Frontiers in Psychiatry, Mar. 2016, vol. 7(33), 9 pages.
Everson-Rose et al., "Chronic Stress, Depressive Symptoms, Anger, Hostility, and Risk of Stroke and Transient Ischemic Attack in the Multi-Ethnic Study of Atherosclerosis," Stroke (American Heart Association, Inc.), Aug. 2014, 45:2318-2323, 6 pages.
Halaris, "Inflammation-Associated Co-morbidity Between Depression and Cardiovascular Disease," Current Topics in Behavioral Neurosciences, vol. 31, Nov. 8, 2016, pp. 45-70.
Hirschfeld et al., "The Comorbidity of Major Depression and Anxiety Disorders: Recognition and Management in Primary Care," Primary Care Companion J Clin Psychiatry, Dec. 2001, 3(6), pp. 244-254.

Huang et al., "Nonapnea sleep disorders are associated with subsequent ischemic stroke risk: a nationwide, population-based, retrospective cohort study", Sleep Medicine, vol. 14, Issue 12, Dec. 2013, pp. 1341-1347.
Jangpangi et al., "Alteration of Heart Rate Variability in Patients of Depression", Journal of Clinical and Diagnostic Research:JCDR, Dec. 2016, vol. 10(12): CM04-CM06, 3 pages.
Liu et al., "The link between angiotensin 11-mediated anxiety and mood disorders with NADPH oxidase-induced oxidative stress," International Journal of Physiology, Pathophysiology, and Pharmacology, 2012 (published online Feb. 15, 2012), vol. 4(1):28-35, 8 pages.
Liu et al., "A Risk Score for Predicting Post-Traumatic Stress Disorder in Adults in a Chinese Earthquake Area," The Journal of International Medical Research, Dec. 2012, vol. 40, pp. 2191-2198.
Michopoulos et al., "Posttraumatic stress disorder: A metabolic disorder in disguise?" Experimental Neurology (Elsevier), May 2016, vol. 284, pp. 220-229.
Michopoulos et al., "Diagnostic Biomarkers for Posttraumatic Stress Disorder (PTSD): Promising Horizons from Translational Neuroscience Research," Bioi Psychiatry. Author Manuscript, Sep. 1, 2015, 78(5):344-353, 21 pages.
Morris et al., "Cortisol, heart rate, and blood pressure as early markers of PTSD risk: A systematic review and meta-analysis," Clinical Psychology Review, Sep. 2016, vol. 49, 35 pages.
Mortensen et al., "Catheter-Based Renal Sympathetic Denervation Improves Central Hemodynamics and Arterial Stiffness: A Pilot Study," The Journal of Clinical Hypertension, Dec. 2012, vol. 14(12), pp. 861-870.
Oparil et al., "New Approaches in the Treatment of Hypertension," Circulation Research, Mar. 13, 2015, 116:1074-1095, 23 pages.
Raison et al., "Do Cytokines Really Sing the Blues?" Cerebrum, Aug. 2013, 16 pages.
Sapolsky, "Depression, antidepressants, and the shrinking hippocampus," PNAS, Oct. 23, 2001, vol. 98(22), pp. 12320-12322.
Serra F, Spoto A, Ghisi M and Vidotto G (2017) Improving Major Depressive Episode Assessment: A New Tool Developed by Formal Psychological Assessment. Front. Psychol. 8:214. doi: 10.3389/fpsyg.2017.00214. Feb. 17, 2017, 14 pages.
Schlaich et al., "Effects of renal denervation on sympathetic activation, blood pressure, and glucose metabolism in patients with resistant hypertension," Frontiers in Physiology, Feb. 2012, vol. 3, Article 10, 7 pages.
Spijker et al., "Glucocorticoid Sensitivity in Mood Disorders", Neuroendocrinology, 2012, vol. 95, pp. 179-186, Epublished Nov. 8, 2011.
Towfighi et al., "Poststroke Depression: A Scientific Statement for Healthcare Professionals From the American Heart Association/American Stroke Association," Stroke, Feb. 2017, 48:e30-e44, 14 pages.
Tsuda, "Renin-Angiotensin System and Sympathetic Neurotransmitter Release in the Central Nervous System of Hypertension," International Journal of Hypertension, (accepted) Oct. 18, 2012, vol. 2012, Article ID 4 7 4870, 12 pages.
Ulmer et al., "Nocturnal Blood Pressure Non-Dipping, Posttraumatic Stress Disorder, and Sleep Quality in Women," Behav Med. Author Manuscript, 2013, 39(4):111-121, 19 pages, first published Mar. 2014.
Veith et al., "Sympathetic Nervous System Activity in Major Depression", Arch Gen Psychiatry, May 1994, vol. 51, Article 5, pp. 411-422.
Young et al., "Cortisol and Catecholamines in Posttraumatic Stress Disorder An Epidemiologic Community Study," Arch Gen Psychiatry, Apr. 2004, vol. 61, pp. 394-401.
Zuern et al., "Effects of renal sympathetic denervation on 24-hour blood pressure variability," Frontiers in Physiology, May 2012, vol. 3(134), 8 pages.

\* cited by examiner

*Arterial Vasculature*

*Venous Vasculature*

Renal Denervation Preclinical Efficacy:
Review of 66 Treated and 64 Naïve Swine

| Group N=Arteries or kidneys | % Non-functional Area | Cortical Axon Area per mm$^2$ | Mean NE (pg/mg) |
|---|---|---|---|
| Naïve 7 day N=64 | 14.6 ± 8.0 | 207.2 ± 134.6 | 264.8 ± 82.9 |
| Symplicity 7 day N=54 | 56.9 ± 28.3 | 66.8 ± 84.6 (68% Decrease) | 92.7 ± 92.7 (65% Decrease) |
| Spyral 7 Day N=12 | 47.3 ± 26.5 | 97.4 ± 73.1 (54% Decrease) | 88 ± 75 (68% Decrease) |

FIG. 8A

*The following questions ask about how you have been feeling over the past month. Please put a tick (x) in the box which is the closest to how often you had trouble sleeping because you:*

| | | Not At All 0 | Less Than Once/Week 1 | Once or Twice/Week 2 | 3 or More Times/Week 3 |
|---|---|---|---|---|---|
| 1 | Cannot get to sleep within 30 minutes | | | | x |
| 2 | Wake up in the middle of the night or early morning | | x | x | |
| 3 | Have to get up to use the bathroom | | | x | |
| 4 | Cannot breathe comfortably | x | | | |
| 5 | Cough or snore loudly | | x | | |
| 6 | Feel too cold | x | | | |
| 7 | Feel too hot | x | | | |
| 8 | Have bad dreams | | | | |
| 9 | Have pain | | x | | |
| 10 | Other reason(s), please describe: | x | | | |
| 11 | During the last month, how often have you take medicine (prescribed or over-the-counter) to help you sleep? | | x | | |
| 12 | During the last month, how often have you had trouble staying awake while driving, eating meals, or engaging in social activities | | | x | |
| 13 | During the last month, how much of a problem has it been for you to keep up enthusiasm to get things done? | | | x | |
| | | Very Good (0) | Fairly Good (1) | Fairly Bad (2) | Very Bad (3) |
| | During the past month, how would you rate your sleep quality overall? | | | x | |

| Total Score: | 17 | Score>10 → Sleep Quality Threshold |
|---|---|---|

FIG. 9

| Answer the questions below by placing "y" or "n" in the box | |
|---|---|
| SDNN (Standard Deviation NN intervals) < 50 ms | y |
| Baroreceptor Sensitivity (BRS) < 1.74 ms/mmHg | y |
| Heart Rate increase > 10 bpm during Stroop Color Test | n |
| Heart Rate increase > 10 bpm or Systolic Blood Pressure increase > 10 mmHg during Stroop Color Test | n |
| Heart Rate increase > 10 bpm or Systolic Blood Pressure increase > 10 mmHg during Cold Pressor Test | n |
| Muscle Sympathetic Nerve Activity > 25 bursts/min | n |

RDN Candidate

FIG. 9 (Cont.)

METHODS FOR TREATING SLEEP DISORDERS IN PATIENTS VIA RENAL NEUROMODULATION

CROSS-REFERENCE TO RELATED APPLICATION(S)

The present application claims priority to U.S. Provisional Patent Application No. 62/528,867, filed Jul. 5, 2017; U.S. Provisional Patent Application No. 62/528,876, filed Jul. 5, 2017; U.S. Provisional Patent Application No. 62/570,597, filed Oct. 10, 2017; and to U.S. Provisional Patent Application No. 62/570,603, filed Oct. 10, 2017, all of which are incorporated herein by reference in their entireties.

TECHNICAL FIELD

The present technology relates generally to systems, devices, and methods for treating sleep disorders and/or for reducing a risk associated with developing a sleep disorder in patients via renal neuromodulation.

BACKGROUND

Sleep disorders are medical conditions causing disruption to a person's sleep quality or pattern. Depending on the severity or the type of sleep dysfunction, the number of symptoms and/or persistence (e.g., duration) of symptoms, sleep disorders can interfere with mental, physical and/or social function in the affected person, thereby greatly impacting quality of life. Numerous studies have demonstrated that sleep is vital for both physical and mental function, and sleep disorders causing, for example, lack of sleep (e.g., insomnia) or poor sleep quality (e.g., sleep apnea) can result in daytime fatigue, impaired cognitive function, mood disturbances, increased rates of illness, and depression having significant impact in professional performance and social function. The Center for Disease Control estimates that one third of adults in the United States are getting insufficient sleep (e.g., short sleep duration) and the World Health Organization estimates sleep disorders are significantly on the rise (currently 10% of U.S. adults) with 1 in 3 people globally suffering from at least one aspect of insomnia. In addition to physical and mental health impacts, sleep disorders also have significant economic burden attributable to work absences and reduced productivity, as well as direct health care costs to patients.

Sleep disorders are typically treated with a combination of medication and psychotherapy. Despite current treatment options, however, the burden of sleep disorders and other related mental health conditions remains high. As sleep disorders can have severe psychological, cognitive, physical, social and economic impact on patients as well as families and society, there is a need for treatments that effectively treat and/or manage sleep-related disorders, including the severity of symptoms associated with such disorders. Furthermore, there is a need for treatments that effectively reduce the incidence or development of a sleep disorder, or provide other improvements in prognosis and outcomes for patients having, or at risk of developing, a sleep-related disorder.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 8A is a display table illustrating results from a study to determine the effects of renal denervation on cortical axon density and mean norepinephrine concentration in animal subjects.

FIG. 9 illustrates a sleep disorder risk score calculator for determining a patient's sleep disorder risk score in accordance with an embodiment of the present technology.

DETAILED DESCRIPTION

Figure 1:
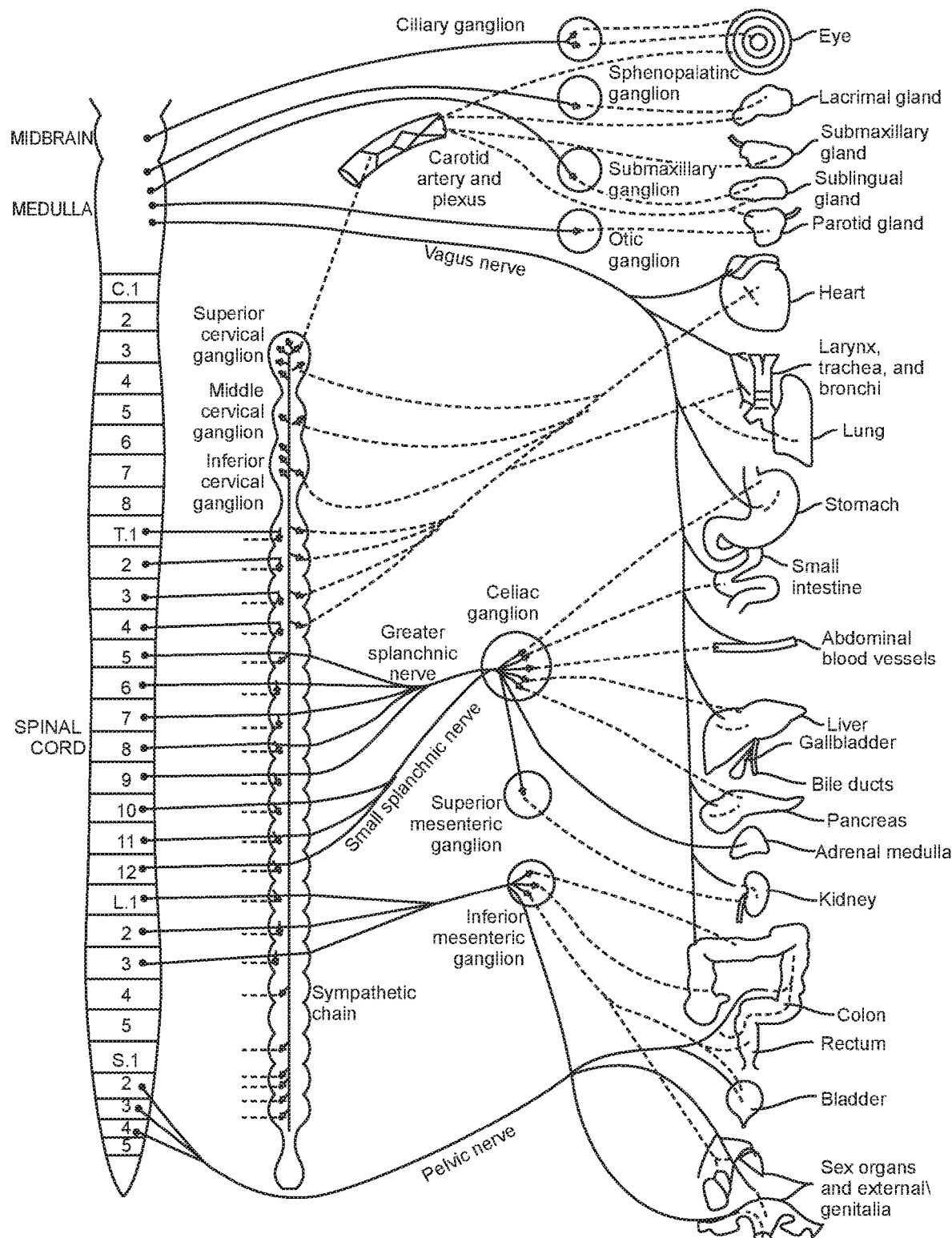
FIG. 1 is a conceptual illustration of the sympathetic nervous system (SNS) and how the brain communicates with the body via the SNS.

The present technology is directed to methods for treating sleep disorders, managing symptoms or sequelae associated with sleep disorders, reducing a severity of sleep disorders, and/or for reducing a risk associated with developing a sleep disorder in patients via renal neuromodulation. In certain embodiments, the present technology is directed to beneficially improving one or more measurable physiological parameters associated with sleep disorders in a patient via renal neuromodulation. Other embodiments of the present technology include performing therapeutically-effective renal neuromodulation on a patient to reduce a severity of neurobiological symptoms relating to a sleep disorder. Further embodiments of the present technology include performing therapeutically-effective renal neuromodulation on a patient to reduce the risk of occurrence of a sleep disorder in at-risk patients.

In yet another embodiment, a patient having had one or more previous episodes or diagnosis of a sleep disorder can be treated with therapeutically-effective renal neuromodulation to reduce a risk associated with reoccurrence of the sleep disorder or development of another sleep disorder. In a particular embodiment, for example, the patient has experienced one or more periods of sleep deprivation (inability to fall asleep or maintain sleep) that poses a measurable risk for experiencing a reoccurrence or a pattern of such symptoms, but the patient does not currently meet the standard for a sleep disorder diagnosis. In another particular embodiment, the patient has had a previous, but not current, diagnosis of a sleep disorder that poses a measurable risk for developing the same or a different related Axis I disorder (e.g., anxiety disorder, depression, etc.). In some embodiments, the patient exhibits one or more additional risk factors for the development of a sleep disorder following a traumatic event, life change or stressful situation. Other embodiments of the present technology include performing therapeutically-effective renal neuromodulation on a patient prior to the patient experiencing a potentially life-debilitating or life-threatening episode. For example, the patient may also be diagnosed with depression, an anxiety disorder (e.g., general anxiety disorder, post-traumatic stress disorder (PTSD), etc.) and/or other psychotic disorder, have had one or more suicide attempts during previous depressive or debilitating episodes or, in another embodiment, the patient may also be experiencing physical health issues related to chronic/uncontrollable stress.

The present technology is further directed to methods for reducing an incidence of cardiovascular disease or a cardiovascular event in patients diagnosed with a sleep disorder. In certain embodiments, for example, the present technology is directed to improving one or more measurable physiological parameters associated with cardiovascular health in the patient experiencing sleep dysfunction-associated symptoms or having a sleep disorder diagnosis via renal neuromodulation. Other embodiments of the present technology include performing therapeutically-effective renal neuromodulation on a patient diagnosed with a sleep disorder to reduce a severity of a cardiovascular condition. Further embodiments of the present technology include performing therapeutically-effective renal neuromodulation on a patient diagnosed with a sleep disorder to reduce the risk of occurrence of a cardiovascular event in such patient in later life.

As discussed in greater detail below, therapeutically-effective renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-9. The embodiments can include, for example, modulating nerves proximate (e.g., at or near) a renal artery, a renal vein, and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-9.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. SLEEP DISORDERS

Sleep disorders can be categorized as dyssomnias, parasomnias, circadian rhythm sleep disorders involving the timing of sleep, and other disorders caused by medical or psychological conditions. Dyssomnias are characterized by either hypersomnia or insomnia, but also include sleep disordered breathing (e.g., sleep apnea, snoring, upper airway resistance syndrome), restless leg syndrome (i.e., irresistible urge to move legs), and periodic limb movement disorder (i.e., sudden involuntary movement of arms and/or legs during sleep). Insomnia is characterized by chronic difficulty in falling asleep and/or maintaining sleep. Hypersomnia, or excessive sleepiness, is a condition in which the patient has trouble staying awake during the day, even at inappropriate times/places (e.g., while at work, while driving). Hypersomnia may be result of narcolepsy or may be due to fatigue associated with disrupted sleep during the night (e.g., conditions associated with insomnia, sleep disordered breathing, restless leg syndrome, periodic limb movement, etc.).

Parasomnias are a category of sleep disorders that are characterized by abnormal behavioral, experiential or physiological events that occur during sleep or sleep-wake transitions, such as, bedwetting, sleep terrors, sleep walking, sleep talking, and sleep-related eating, among others.

Circadian rhythm sleep disorders include delayed sleep phase disorder (e.g., typical sleep pattern is delayed by two or more hours at night), advanced sleep phase disorder (e.g., typical sleep pattern causes early rising and difficulty with sleepiness later in the day), and non-24-hour sleep-wake disorder (e.g., individual's sleep patterns don't align with a 24 hour clock and constantly have shifting sleep schedules). In all cases of circadian rhythm sleep disorders, the disorders impact daytime function when the individual attempts to conform to conventional sleep schedules for work or social situations.

Medical or psychological conditions that can cause or contribute to sleep disorders include, for example, anxiety disorders (including, e.g., a fear of falling asleep), depression, alcoholism, psychosis (e.g., Schizophrenia), and sleeping sickness (i.e., parasitic disease). Additional causes of sleep disorders or sleep-related symptoms may accompany or be due to diseases or illnesses such as, for example, thyroid disorders, cardiovascular disease, stroke, obesity, metabolic disorders (e.g., diabetes), menopause, autoimmune disorders, and brain degenerative diseases (e.g., Parkinson's disease, multiple sclerosis, dementia, Huntington's disease) and well as brain trauma (e.g., traumatic brain injury (TBI)).

Persons with chronic (e.g., greater than 3 months), unpredictable and/or uncontrollable sleep-related symptoms (e.g., narcolepsy), as well as other sleep disruptive disorders (e.g., insomnia, sleep apnea, circadian rhythm disorders, parasomnias) report difficulties with work, school, home, relationships and/or social activities, and numerous studies have also shown that persons with a sleep disorder have more functional limitations than those without a sleep disorder.

As used herein, "sleep disorder" refers to any form of sleep disorder or illness associated with disruptions in sleep patterns or sleep quality experienced by an individual and persisting for several weeks or months (e.g., 1 month, at least three months), and/or in which one or more sleep quality screening tools or instruments are used to give a professionally-accepted diagnosis.

As there are several forms of sleep disorders that are distinguished by a spectrum of symptom types and severity as well as the persistence of the disorder in an affected individual, clinically-accepted diagnosis of a sleep disorder, may be found in the American Psychiatric Association defines the criteria in its Diagnostic and Statistical Manual of Mental Disorders (DSM-5). While occasional sleep disruption (i.e., difficulty falling asleep, waking during the night) and sleep deprivation (i.e., jet lag, work schedule changes) are normal and/or can accompany periods of acute stress or result from a life event or circumstance, a sleep disorder can be characterized by symptoms that are excessive and/or non-temporary (e.g., longer than three months, age inappropriate, causing injury to the individual or others, hinder ability to function appropriately, etc.). In some situations, patients can be afflicted with more than one sleep disorder. In all forms of sleep disorders, however, affected and/or susceptible individuals may develop ongoing (chronic), short-term (acute) or recurring sleep dysfunction-associated episodes with potential for debilitating mental and physical health outcomes.

As discussed above, diagnosis of a sleep disorder is based on the identification of the clinical criteria (e.g., symptoms and signs) as set forth in DSM-5. Clinicians and other mental health practitioners typically use conventionally accepted diagnostic test methods, such as screening tools (e.g., for use during diagnostic interviews, patient health questionnaires, etc.) or sleeping tests for identifying sleep disorder risk, severity and diagnosis. These screening tools are typically focused on core symptoms as set forth in DSM-5, but some screening tools provide further diagnostic capability to determine symptom severity, various specifiers, and/or other risk factors. For example, severity is typically determined by the degree of disability (e.g., cognitive, physical, social, occupational, etc.) or pain experienced by the patient as well as the duration of the symptoms. These screening tools are also designed to differentiate sleep disorders from other mental disorders (e.g., depressive disorders). For example, patients can be diagnosed with a sleep disorder and/or a measure of sleep disorder severity can be determined using the Pittsburgh Sleep Quality Assessment (PSQI), the Epworth Sleepiness Scale (ESS), Iowa Sleep Disturbances Inventory (ISDI), Morningness-Eveningness Questionnaire (MEQ), or a Visual Analogue Scale for Sleep Quality (VAS). Other questionnaires combine anxiety and depression measurement, such as the Hamilton Anxiety Rating Scale, the Hospital Anxiety and Depression Scale (HADS), and the Patient Health Questionnaire (PHQ-ADS), Laboratory or at-home sleep tests utilizing sensors for detecting patient's brain waves, electroencephalograms (EEG), muscle activity and eye movements for assessing sleep patterns and sleep quality can include the Multiple Sleep Latency Test (MSLT) or a multi-parametric test such as polysomnography test that can test for additional parameters, such as heart rhythm by electrocardiogram (ECG), respiratory airflow, peripheral pulse oximetry, etc. As disclosed herein, such screening tools can be used to provide a risk score for predicting a patient's sleep disorder status with respect to disorder diagnosis, sleep disorder severity and/or identifying at-risk populations.

Certain risk factors have been identified that may make an individual more likely (e.g., increase a risk) to develop a sleep disorder during their lifetime. For example, some identified risk factors for increasing a likelihood of developing a sleep disorder include having a family history and/or personal history of a sleep disorder, depression, an anxiety disorder or other mental illness, experiencing adverse life events (e.g., illness, abuse, loss of a loved one, unemployment, psychological trauma, etc.), having experienced prior traumatic events, being a childhood survivor of abuse, experiencing trauma during childhood, experiencing parental loss or separation, having a history of substance abuse, having a history of eating disorder, experiencing a difficult relationship, being in a stressful situation, experiencing a major life change, experiencing an extended period of stress (e.g., chronic stress), a smoker, and physically inactive, among others.

Patients presenting with a sleep disorder may also experience other adverse mental and physical diseases and disorders. For example, sleep disorders have high comorbidity with mental disorders such as major depressive disorder, substance and alcohol abuse, and suicidal tendencies. Further, cardiovascular disease, stroke, hypertension, obesity (e.g., high body mass index (BMI)), cancer, chronic kidney disease, female infertility, osteoporosis, and metabolic disorders, such as type 2 diabetes, among others are also highly comorbid with sleep disorders (Huang, S T, et. al., Medicine, 2015, 94:1-7; Chung, W S, et al., Sleep, 2013, 12: 1963-1968; Rizzi, M., et al., J Clin Transl Endocrinol, 2014, 1:44-48). Without being bound by theory, it is possible that sleep disorders share underlying neuroendocrine, metabolic and other psychophysiological patterns with these other disorders that either increase risk for the development of a sleep disorder or reduce treatment success and/or increase risk for the development of these additional conditions.

A. Biophysical Characteristics of Individuals With Sleep Disorders

Sleep disorders belong to a mental disorder category encompassing complex and multifactorial disorders that are thought to be caused by many contributing factors. The underlying neurobiological and metabolic mechanisms or etiology of sleep disorders are uncertain and/or may vary depending on the category of sleep disorder; however, evidence suggests that psychological, genomic and other biological risk factors are present in patients identified with sleep disorders. Moreover, neurobiological heterogeneity in monoaminergic transmitter systems, the hypothalamic-pituitary-adrenal (HPA) axis, metabolic hormonal pathways, inflammatory mechanisms, and psychophysiological reactive and neural circuits have been demonstrated between individuals diagnosed with sleep disorders and healthy individuals (Irwin, M. R., et al., *Biol Psychiatry*, 2016, 80: 40-52; Buckley, T. M., and Schatzberg, A. F., *J Clin Endocrinol Med*, 2005, 90: 3106-3114). In addition to differences between individuals diagnosed with a sleep disorder and healthy individuals, those who do meet the criteria for a diagnosis of a sleep disorder can vary in the severity of their symptoms as well as the type of symptoms they experience.

Psychological stress, including chronic stress, can have deleterious effects on the brain's neural circuits as well as whole-body physiological states, and is a crucial factor underlying mental disorders, with variation in stress susceptibility, responsivity and resilience providing variances in disorder presentation and severity (Halaris, A., *Curr Topics Behav Neurosci*, 2017, 31:45-70). The neuro-hormonal systems that play a critical role in stress responses and homeostasis include the HPA axis and noradrenergic systems. The noradrenergic system includes a dense network of axons that extend from the locus coeruleus in the brain stem throughout the brain including the hippocampus, amygdala, thalamus and hypothalamus, as well as projections that extend down the brain stem to synapse with sympathetic nerve fibers in the thoracic region.

Correlative links have been implicated between a variety of mood and cognitive disorders and chronic or prolonged hyperactivity of the sympathetic branch of the autonomic nervous system. As shown in FIG. 1, the SNS is a branch of the autonomic nervous system along with the enteric nervous system and parasympathetic nervous system. The SNS is primarily an involuntary bodily control system typically associated with stress responses. It is always active at a basal level (called sympathetic tone) and becomes more active during times of stress. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. The SNS regulates the function of virtually all human organ systems by localized release of catecholamines (e.g., norepinephrine) from sympathetic nerve terminals innervating these tissue and organ systems, spillover of norepinephrine from vascular neuromuscular junctions (the primary source of norepinephrine in plasma), and by systemic circulation of catecholamines (e.g., epinephrine, norepinephrine) released from the adrenal gland in response to acute, transient stress or threats. Long-term variations in basal levels, increases in basal levels due to aging, as well as spikes of circulating catecholamines from hyperactivity of the SNS responding to life circumstances can also exert more enduring regulatory effects on gene expression by altering constitutive gene expression profiles in a wide variety of tissues and organ systems.

In addition to release of norepinephrine from sympathetic nerve terminals innervating these tissue and organ systems, perivascular adipose tissue, which closely surrounds most blood vessels (except in the brain), has been shown to contain pools of norepinephrine. Renal perivascular adipose tissue, in particular, can release stored norepinephrine, thereby altering renal vascular function and contributing to spillover of norepinephrine to plasma.

Once released, norepinephrine binds adrenergic receptors on peripheral tissues. In addition, activation (e.g., norepinephrine release) of noradrenergic nuclei in the central nervous system (CNS) can result from transmitted impulses from activated afferent renal sympathetic neurons. Binding to adrenergic receptors either in the periphery or in the CNS causes a neuronal and hormonal response. The physiologic manifestations include pupil dilation, increased heart rate, occasional vomiting, and increased blood pressure. Increased sweating is also seen due to binding of cholinergic receptors of the sweat glands. It is known that long-term SNS hyperactivity has been identified as a major contributor to the complex pathophysiology of hypertension, states of volume overload (such as heart failure), and progressive renal disease, both experimentally and in humans. Moreover, correlative links between activation of the SNS and systemic inflammation, arterial stiffness, atherosclerosis, metabolic disorders, insulin resistance, and other cardiovascular conditions have been established. As mentioned above, many of these conditions are comorbid with sleep disorders.

Increased levels of catecholamine (e.g., norepinephrine) spillover and secretion are associated with sleep disorders. For example, higher levels of circulating catecholamines, such as norepinephrine (in the periphery and central nervous systems), have been reported in sleep disorders including sleep apnea and non-apnea sleep disorders (e.g., insomnia); and an activated noradrenergic system is implicated in psychological stress, which is one of the primary risk factors for sleep disorder development. Without being bound by theory, this suggests that increased SNS activity is present in sleep disorder patients.

Other indicators of increased SNS tone in patients with sleep disorders include elevations in heart rate, blood pressure, skin conductance, and platelet activation as well as a decrease in heart rate variability (e.g., a measure of beat-to-beat fluctuations in heart rate). In contrast, healthy individuals that do not meet the criteria for a sleep disorder may exhibit significantly lower plasma catecholamine levels and may not display other indicators of elevated SNS activity.

Without being bound by theory, increased levels of norepinephrine can account for many aspects of sleep disorder-associated symptoms, including sleep disturbances (e.g., difficulty in falling asleep, waking in the middle of the night or early morning, waking to use the bathroom, snoring and/or coughing, unable to breath comfortably, too cold or hot, experiencing bad dreams, experiencing pain, and experiencing restless legs before or during sleep), difficulty staying awake during the day, experiencing difficulty in maintaining enthusiasm in activities or hobbies, impaired concentration, irritability, and feelings of sadness or anxiousness. Hyperactive SNS activity in patients with sleep disorders would also present an on-going challenge to treatment success as levels of norepinephrine increase or spike in response to stressors and/or worsening psychological stress in these individuals.

Individuals with sleep disorders also exhibit altered HPA axis function as evidenced by elevated levels of corticotropin-releasing hormone (CRH) and increased nocturnal CRH activity, which initiates stimulation of the HPA axis in response to stress (e.g., psychological stress, etc.) (Buckley, T. M., and Schatzberg, A. F., *J Clin Endocrinol Med*, 2005, 90: 3106-3114). Hyperactivity of the HPA axis as well as higher circulating cortisol (i.e., glucocorticoid) levels compared to healthy controls (e.g., patients without sleep disorders) also exemplify HPA axis dysfunction in remitted as well as currently diagnosed patients (Id.). Decreased responsiveness to glucocorticoids (e.g., glucocorticoid resistance) and subsequent HPA axis dysfunction is a hallmark of major depression (Miller, A. H., et al., *Biol Psychiatry*, 2009, 65: 732-741), and may also be in related disorders (e.g., sleep disorders). Alterations to HPA axis function, both reflecting a current mood state as well as long lasting changes to brain function, may be mediated, in part, by alterations in the glucocorticoid receptor. In particular, it has been demonstrated that patients with depression, anxiety and sleep disorders exhibit reduced glucocorticoid sensitivity, preferential expression of a dominate negative form (GR-β) of the glucocorticoid receptor, and increased levels of FKBP5, which is a co-chaperone of the glucocorticoid receptor that inhibits ligand binding and pathway activation (Menke, A., et al., *Genes, Brain and Behav*, 2013, 12: 289-296; Spijker, A. T. and van Rossum, E. F. C., *Neuroendocrinology*, 2012, 95:179-186; Miller, A. H., et al., *Biol Psychiatry*, 2009, 65: 732-741). Without being bound by a theory, an individual's level of chronic exposure to stress, and thereby cortisol exposure, in brain regions associated with emotion and cognition (e.g., the limbic system), may be important in the development or prediction of future risk of a sleep disorder in the individual, and this additional major stress response system may determine longer-term patterns of stress responses in sleep disorder patients (Wang, Z J, et al., *Nature Scientific Reports*, 2015, 5: 9442).

CRH and norepinephrine are known to interact in regions of the brain involved in stress responses to increase fear conditioning, interfere in emotional response, cognition and encoding of emotional memories (Jedema, H. P. and Grace, A. A., *J Neurosci*, 2004, 24:9703-9713). Further reinforcing a prolonged psychological stress response and the pathophysiology of sleep disorders, CRH is elevated in the locus coeruleus of sleep disorder patients and has been shown to activate neurons in the locus coeruleus which would result in increased norepinephrine levels throughout the CNS (Wang, Z J, et al., *Nature Scientific Reports*, 2015, 5: 9442; Buckley, T. M., and Schatzberg, A. F., *J Clin Endocrinol Med*, 2005, 90: 3106-3114).

Neuropeptide Y (NPY), a 36-amino-acid peptide transmitter that is expressed in brain regions that regulate stress and emotional behaviors, has shown to buffer stress responses and promote increased ability to cope with emotional trauma (Enman, N. M., et al., *Neurobiol Stress*, 2015, 1: 33-43; Sah, R. and Geracioti, T. D., *Mol Psychiatry*, 2013, 18:646-655). In particular, central nervous system NPY concentration levels may normally control or suppress pro-stress transmitters such as CRH and norepinephrine in the brain (Id.). However, both central and peripheral nervous system NPY concentrations are significantly lower in individuals with sleep and mood disorders when compared to healthy controls (Id.), possibly attenuating the individuals' resilience and coping ability in response to psychological stress. Without being bound by theory, and since NPY functions to inhibit CRH and norepinephrine promotion of stress and fear responses, as well as reduces the release of norepinephrine from sympathetic neurons, decreased NPY activity may contribute to SNS hyperactivity in patients with sleep disorders.

An additional physiological characteristic associated with a sleep disorder includes a pro-inflammatory state, including chronic inflammation (Irwin, M. R., et al., *Biol Psychiatry*, 2016, 80: 40-52; Buckley, T. M., and Schatzberg, A. F., *J Clin Endocrinol Med*, 2005, 90: 3106-3114). For example, elevated levels of inflammatory cytokines, such as interleukin-6 (IL-6), IL-8, tumor necrosis factor-alpha (TNF-$\alpha$) as well as other inflammatory markers, such as C-reactive protein (CRP), are elevated in individuals with a sleep disorder, and peripheral levels of these inflammatory markers correlate positively with sleep disorder symptomology (e.g., fatigue, cognitive dysfunction, impaired sleep) (Id.). Moreover, higher levels of inflammatory biomarkers are associated with exacerbated sleep disorder symptoms, and without being bound by theory, may pose an increased risk in the development of a sleep disorder.

Sleep disorders are also associated with increased activation of the transcriptional factor, nuclear factor-$\kappa$B (NF-$\kappa$B), which is activated by exposure to psychosocial stress and sympathetic nervous system outflow pathways, and is responsible for cytokine production (Irwin, M. R., et al., *Biol Psychiatry*, 2016, 80: 40-52). Cytokine-induced increases in neural activity in brain regions, such as the anterior cingulated cortex and the basal ganglia, have been associated the development of mood and anxiety symptoms, and are associated with alterations in brain neurotransmitter metabolism (e.g., serotonin, norepinephrine and dopamine), neuroendocrine function and neural plasticity (Id.). For example, cytokine-induced immune responses have shown to increase the number of reuptake pumps, thereby decreasing neurotransmitter availability, and shunting tryptophan away from the production of serotonin in the brain. Without being bound by theory, increased SNS activity coupled with reduced sensitivity to the anti-inflammatory effects of glucocorticoids (e.g., due to glucocorticoid resistance) as a result of chronic psychological stress, both contribute to chronic activation of inflammatory responses.

Currently prescribed treatment plans for patients diagnosed with sleep disorders typically consist of pharmaceutical drugs and/or psychotherapy. Conventional drug therapies are administered to address particular symptoms associated with sleep disorders in attempts to lessen those particular symptoms. For example, sleeping medications, such as insomnia medications (e.g., temazepam, triazolam, zaleplon, zolpidem, etc.), anti-anxiety medication (e.g., benzodiazepines, buspirone, $\beta$-blocker, etc.), antidepressants (e.g., selective serotonin reuptake inhibitors (SSRIs) that raise the level of serotonin in the brain, tricyclic antidepressants, monoamine oxidase inhibitors (MAOIs), etc.), anti-psychotic drugs, anti-hypertensive drugs, mood stabilizers, etc., may provide mild to moderate and/or temporary relief from sleep-related symptoms, anxiety-related symptoms, cognitive and/or memory difficulties, etc. However, most patients do not get adequate treatment and for many patients, medications are ineffective. Moreover, drug adherence over several years or decades in a manner than maintains sleep quality, mood, anxiety disorder-related symptoms, blood pressure, etc., remains a challenge for most patients. For many patients, improvements may not be apparent until after up to 4 or more weeks of drug treatment, causing delays in ascertaining whether the prescribed drug or drug combination is suitable for the particular patient. Furthermore, some medications do not work or stop working effectively over time, and some become addictive and/or cause other intolerable side effects. Additional drawbacks to use of drugs for treating a patient with a sleep disorder include the possibilities of adverse reactions associated with these medications (e.g., heart failure, hypotension, bradycardia, severe depressive episodes, suicide ideation, sexual dysfunction, weight gain or unhealthy weight loss, death, etc.), as well as other undesirable side-effects, on a patient-by-patient basis.

Additionally, pharmaceutical intervention for other contributors and risk factors associated with sleep disorders further complicates drug administration and management of contraindications between anti-inflammatory medications, anti-hypertensive drugs, anti-anxiety drugs, antidepressant drugs, mood stabilizers among others administered to support patients with sleep disorders, and adherence over years remains a challenge. Various psychotherapy treatments can be prescribed in combination with a medication plan or as a stand-alone treatment. While psychotherapy (e.g., cognitive-behavioral therapy, interpersonal therapy, etc.) may provide some patients with skills in new ways of thinking and behaving, it may not be effective for more severe forms of sleep disorders such as insomnia, sleep apnea (e.g., obstructive sleep apnea), narcolepsy, among others. Some patients with severe or medication adverse and/or resistant disorders may be treated with several sessions of electroconvulsive therapy, phototherapy, deep brain stimulation and others with mixed results. Various aspects of the present technology address SNS effects on risk factors associated with sleep disorders while overcoming these challenges.

B. Risk Factors Associated With Development of Sleep Disorders and/or Related Conditions As discussed above, sleep disorders are psychophysiological disorders encompassing dysregulation of complex neuro- and hormonal-biochemical pathways that are known to be caused by many contributing factors. While many biomarkers distinguishing patients with a sleep disorder and healthy individuals demonstrate heterogeneity following pathogenesis in an individual, certain earlier-identifiable conditions as well as genetic and/or biophysical variances in a patient are recognized as being either contributory factors and/or predictors of a likelihood that a patient will develop a sleep disorder or, in the case of remitted patients, a likelihood that the patient will redevelop the same sleep disorder or develop a different sleep disorder. In particular, many underlying conditions, genetic variances and other abnormalities detectable in individuals either prior to the development of a sleep disorder or during remittance, may affect the likelihood of the individual subsequently developing one or more sleep disorders. Such underlying conditions and genetic/biophysical variances constitute sleep disorder predictors or risk factors.

As discussed above, some identified risk factors for increasing a likelihood of developing a sleep disorder include certain demographic variables such as, for example, smoking, drug or alcohol abuse, being overweight, and being physically inactive. Additionally, it has been shown that if the patient has a history of sleep disorders, mental illness or substance abuse, has a family history of sleep disorders, depression or other mental illness, has experienced one or more adverse life events (e.g., illness, abuse, loss of a loved one, unemployment, psychological trauma, etc.), has or is experiencing a difficult relationship, has experienced prior traumatic events, has had an adverse childhood experience, is currently in a stressful situation, has or is experiencing a major life change, or has or is experiencing an extended period of stress (e.g., chronic stress), among others, the patient has an increased likelihood of developing a sleep disorder.

Without being bound by theory, increased SNS activity in the patient as a result of psychological and/or other forms of chronic stress can predispose the individual to developing a sleep disorder. For example, chronic stress has been shown to alter neural circuits and structures in the brain (e.g., hippocampus, prefrontal cortex, etc.) (Pitman, R. K., et al., *Nat Rev Neurosci.*, 2012, 13: 769-787) that may increase the individual's sensitivity to contextual threat. Such sensitization of the SNS may be responsible for higher heart rates during a subsequent exposure to a trigger, stressful situation or a traumatic event, which may be a predictive risk for future development of a mood disorder accompanied by a sleep disturbances. Moreover, lower heart rate variability characterizes sleep disorders and may also be predictive of sleep disorder development. In certain embodiments, prior exposure to trauma (e.g., childhood abuse, prior sexual abuse, prior combat experience, etc.) may increase the individual's sensitization of the SNS, thereby lowering the threshold barriers for the development of a sleep disorder.

While there is evidence for the presence of SNS hyperactivity in patients presenting with a sleep disorder, there is further evidence that a strong adrenergic response to a traumatic event or other adverse life circumstance may mediate or in part contribute to the development of a sleep disorder in certain individuals. Some biochemical inducements of the increase in norepinephrine release in response to SNS activation include genetic and/or other inhibition paths that lower NPY levels, as well as lower numbers or affinity of α2-adrenergic receptors (Pitman, R. K., et al., *Nat Rev Neurosci.*, 2012, 13: 769-787; Sherin, J. E., et al., *Dialogues Clin Neurosci*, 2011, 13: 263-278). Additionally, there is evidence that a pro-inflammatory state (e.g., as indicated by increased levels of inflammatory cytokines) may increase risk or vulnerability for development of a sleep disorder particularly when patients present with chronic stress. For example, it has been shown that increased levels of CRP (e.g., greater than about 3 mg/L; greater than about 5 mg/L; etc.) were predictive of psychological distress and depression, and without being bound by theory, elevated levels of CRP can present as an additional risk factor that can establish a predictive risk for the development of a sleep disorder (Irwin, M. R., et al., *Biol Psychiatry*, 2016, 80: 40-52; Buckley, T. M., and Schatzberg, A. F., *J Clin Endocrinol Med*, 2005, 90: 3106-3114).

Correlative links between activation of the SNS and high blood pressure, coronary heart disease, stroke, systemic inflammation, arterial stiffness, endothelium dysfunction, atherosclerosis, metabolic disorders, insulin resistance, end organ damage, obesity (e.g., high body mass index (BMI)), and other cardiovascular conditions have also been established. As discussed above, these conditions/diseases have further been shown to be correlative with an incidence of sleep disorders. As such, it is posited that these conditions/diseases, which are indicative of chronic activation of SNS, present as risk factors that can establish a predictive risk for the development of a sleep disorder. In fact, sleep disorders are more prevalent in people who have suffered a major cardiac event. Strokes (e.g., acute ischemic stroke, lacunar stroke, transient ischemic attack (TIA), hemorrhagic stroke, etc.) are also highly associated with the development of a sleep disorder (e.g., insomnia, sleep apnea), and post-stroke sleep disorders are associated with increased morbidity and mortality in such patients.

Additionally, with respect to blood pressure regulation, the nocturnal blood pressure of healthy individuals drops or "dips" more than 10% of the average daytime blood pressure value, which is followed by an increase in blood pressure with arousal from sleep, known as the morning surge in blood pressure (MSBP). In contrast, "elevated," i.e. limited drops in blood pressure during the nighttime (e.g., nighttime blood pressure reduction that is less than 10% of average daytime blood pressure) as well as excessive surge in MSBP (e.g., early morning hours), is associated with an increased risk of cardiovascular events and strokes even in normotensive patients (FitzGerald, L., et al., *J Hum Hypertens*, 2012, 26: 228-235; Kario, K. and Hamasaki, H., *J Clin Hypertens*, 2015, 17: 682-685). Sleep disorders correlate with higher MSBP and the increase in MSBP is proportional to the severity of the sleep-related symptoms and is irrespective of "dipping" status (Id.). Men and older populations of patients further demonstrate "non-dipping" nocturnal blood pressure which is further associated with more sleep-related symptoms and poorer overall sleep quality as well as increased risk in cardiovascular events (Id.). Psychological risk factors, such as depression and anxiety, are reported to influence cardiovascular events and to impact hypertension, and excessive MSBP and/or "non-dipping" nocturnal blood pressure may be risk factors for the development and/or the severity for hypertension, cardiovascular disease and stroke. Moreover, excessive MSBP and/or "non-dipping" nocturnal blood pressure may be risk factors for the development or progression of sleep disorders in such patients.

In addition to chronic and/or acute SNS hyperactivity, increased glucocorticoid (e.g., cortisol) levels, and HPA axis dysfunction, e.g., as a measurement of basal cortisol levels in response to awakening as an indicator for endogenous stress response, provide additional risk factors that can be considered in establishing a predictive risk assessment for the development of a sleep disorder in a patient (Buckley, T. M., and Schatzberg, A. F., *J Clin Endocrinol Med*, 2005, 90: 3106-3114). For example, and without being bound by theory, an abnormally high measurement of cortisol awakening rise (CAR), which reflects the natural response to awakening with a normal/natural increase in cortisol levels, may not only be characteristic of patients with a sleep disorder, but can be predictive for developing a sleep disorder, and thereby provides an additional risk factor of subsequent sleep disorder development. Without being bound by theory, it is thought that high levels of cortisol resulting in glucocorticoid resistance and increased HPA axis activity fails to inhibit CRH/norepinephrine responses to stress and further exacerbates cognitive dysfunction (e.g., memory deficits, inability to concentrate) and sleep-related symptoms in these individuals.

In addition to predisposition factors associated with activation of the SNS and other demographic risk factors, certain genetic variations among individuals have also been shown to be predictive risk factors for the development of sleep disorders. Some of these genetic risk factors are common to both major depressive disorder, anxiety disorder and sleep disorders. For example, genes that affect risk for development of a sleep disorder may also influence risk for other psychiatric disorders and vice versa. As with other mental disorders, influences on sleep-related disorders are likely polygenic; at least 17 single nucleotide polymorphisms (SNPs) in 15 different genomic regions have been associated with depression and related psychiatric disorders in at least one published study (Hyde, C. L., et al., *Nature Genet*, 2016, 48: 1031-1036). These and other genetic variants demonstrated to influence risk for anxiety, depression, and associated sleep disturbance symptoms include genes involved in HPA axis regulation, the locus coeruleus/noradrenergic system, dopaminergic and serotonergic systems (e.g., regulation of synapses, monoamine metabolism, etc.) and other neurodevelopment programs (Hyde, C. L., et al., *Nature Genet*, 2016, 48: 1031-1036; Converge Consortium, *Nature*, 2015, 523: 588-591; Miller, A. H., et al., *Biol Psychiatry*, 2009, 65: 732-741).

With respect to HPA axis regulation, several known genetic variations in the glucocorticoid receptor gene, NR3C1, affect glucocorticoid sensitivity (Spijker, A. T. and van Rossum, E. F. C., *Neuroendocrinology*, 2012, 95:179-186). For example, the ER22/23EK polymorphism, which is associated with mild glucocorticoid resistance, and the Bc/I polymorphism, which is associated with increased stability of the mRNA of the dominant negative GR-β isoform, are both associated with a higher risk of developing a mood and related disorders (Id.). Additionally, carriers of particular heritable polymorphisms in the genes encoding for FK506-binding protein 5 (FKBP5; co-chaperone of the glucocorticoid receptor that inhibits ligand binding and pathway activation) leading to increased intracellular FKBP5 protein expression, the CRH receptor 1 (CRHR1 rs242939 polymorphism), and serotonin transporter (SLC6A4; responsible for serotonin transport and reuptake) have been shown to be overrepresented in patients with depression, and carriers of these genetic variants have an increased likelihood of developing some types of sleep disorders (Mahan, A. L. and Ressler, K. J., *Trends Neurosci*, 2012, 35: 24-35; Pitman, R. K., et al., *Nat Rev Neurosci.*, 2012, 13: 769-787; Spijker, A. T. and van Rossum, E. F. C., *Neuroendocrinology*, 2012, 95:179-186; Miller, A. H., et al., *Biol Psychiatry*, 2009, 65: 732-741).

Further evidence has suggested that in addition to genotype, epigenetic factors such as gene methylation, histone deacetylation, and other gene expression differences can influence or accompany the development of sleep and other mental disorders, and these genetic profiles can be screened to determine patients presenting certain genetic pre-dispositions associated with high or increased risk of developing a sleep disorder (Spijker, A. T. and van Rossum, E. F. C., *Neuroendocrinology*, 2012, 95: 179-186; Mahan, A. L. and Ressler, K. J., *Trends Neurosci*, 2012, 35: 24-35; Pitman, R. K., et al., *Nat Rev Neurosci.*, 2012, 13: 769-787).

Once a clinical sleep disorder is present, a host of physiological changes occur in the patient, including SNS and immune system activation/hyperactivation, neuroendocrine changes, rhythm disturbances, oxidative stress, platelet hypercoagulability and endothelial dysfunction, all of which exert a negative impact on cardiovascular health. As discussed above, sleep and other mental disorders are characterized by, among other things, elevated SNS activity, reduced heart rate variability, increased plasma cortisol levels and elevated inflammatory responses, all of which are associated with increased risk of cardiovascular disease (Brown, A. D., et al., *CNS Drugs*, 2009, 23:583-602). In particular, psychological stress accompanying a sleep disorder causes dysregulation of the SNS and the HPA axis which can precipitate numerous downstream physiological effects throughout the body, including hypertension, left ventricular hypertrophy, coronary vasoconstriction, endothelial dysfunction, platelet activation and the production of pro-inflammatory cytokines, all of which carry an elevated risk of ventricular arrhythmias and MI. Additionally, sleep disorders (e.g., both sleep apnea and non-apnea sleep disorders) have been shown to be associated with increased morbidity and mortality in patients having cardiovascular disease (Wang, W S, et al., *Sleep*, 2013, 36:1963-1968). Without being bound by theory, mental stress (which accompanies and/or precipitates sleep disorders) has been shown to activate cardiac sympathetic nerves with downstream effects of heart rhythm disturbances, increased risk of ventricular arrhythmias, decreased blood flow, left ventricular hypertrophy, MI and sudden death. Furthermore, essential hypertension can be triggered by and maintained by chronic psychological stress. Accordingly, sleep disorders are a risk factor for the development of cardiovascular disease and stroke, with the relative risk level proportional to the severity of disorder in the patient. Furthermore, sleep disorders in patients significantly increase future risk of stroke and transient ischemic attacks (TIAs), with higher levels of sleep-related symptoms proportional to the increased risk of stroke and TIA (Huang W S, et al., *Sleep Med*, 2013 14: 1341-1347). Excess stroke and TIA risk associated with sleep disorders may stem from activation of the HPA axis, elevated catecholamines, and elevated inflammatory responses (e.g., increased CRP, IL-6, etc.) which are all related to stroke risk.

C. Identification of Patients or Cohorts Diagnosed With a Sleep Disorder or at Risk of Developing a Sleep Disorder Patients presenting with a high likelihood of having a sleep disorder can include patients presenting with one or more of (1) sleep dysfunction-associated symptoms (e.g., difficulty in getting to sleep, difficulty in maintaining sleep, snoring loudly, having bad dreams, feeling too hot or cold, having difficulty breathing comfortably while sleeping, experiencing night pain, requiring medication to sleep, drinking alcohol to fall asleep, feeling fatigued or sleepy while driving or eating meals or engaging in social activities, sleepwalking, impaired concentration, excessive sleeping (e.g., hypersomnia), and irritability), (2) family history of depression, anxiety disorder or other mental illness, (3) prior diagnosis of an acute or chronic stress disorder, (4) prior diagnosis of any mood disorder (e.g., depression, anxiety, bipolar, panic disorder, etc.), and/or (5) depression symptoms (e.g., depressed mood for most of the day, anhedonia, psychomotor agitation or retardation nearly every day, anergia, poor appetite or overeating, low self-esteem or feelings of worthlessness, changes in cognitive ability, and/or negative feelings about self or the world). Patients demonstrating certain risk factors or sleep dysfunction-associated symptoms may also have an increased likelihood of having a sleep disorder if they exhibit with one or more of elevated SNS activity (e.g., catecholamines detected in urine or plasma), low central nervous system NPY levels, elevated cortisol levels, glucocorticoid resistance (e.g., as assessed via dexamethasone suppression test), elevated CAR, low heart rate variability, elevated MSBP, limited or no "dipping" of nocturnal blood pressure, elevated levels of serum inflammatory cytokine levels (e.g., IL-6, IL-8, TNF-α, CRP, etc.), and/or endothelial dysfunction.

Some patients may also present with comorbid conditions or diseases such as cardiovascular disease, having suffered a major cardiac event (e.g., MI, coronary artery bypass surgery), having had a stroke or risk of stroke, hypertension or pre-hypertension, ventricular arrhythmias, left ventricular hypertrophy, above-normal cholesterol levels, atherosclerosis, chronic kidney disease, insulin resistance or other metabolic disorder, arterial stiffening or aneurysm(s), obesity or being overweight (e.g., high BMI), cancer, and/or patients with active substance abuse, a history of substance abuse, or prior mental disorder. In certain embodiments, the patient can present with one or more risk factors and/or comorbid conditions associated with an increased likelihood of having a sleep disorder. However, in other embodiments, such associated conditions may not be present in a patient having a sleep disorder and/or at risk of developing a sleep disorder. For example, the patient may be normotensive, have no evidence of cardiovascular disease, normal BMI, normal insulin sensitivity, and/or no elevated levels of inflammatory biomarkers.

Patients presenting with a high or increased risk of developing a sleep disorder can include patients having one or more demographic or biophysical risk factors as described herein and who have not met the diagnosis standard as set forth in DSM-5 and/or patients in which one or more sleep quality screening tools or instruments used to give a professionally-accepted diagnosis have not confirmed a sleep disorder. However, such patients may present one or more risk factors associated with an increased likelihood of developing a sleep disorder. For example, the patient may have an increased likelihood of a present condition progressing toward a sleep disorder, such as a patient presenting some but not a qualifying number of symptoms on the DSM-5, or in another embodiment, a patient may present a qualifying number of symptoms but has not experienced a threshold level of severity for one or more of those symptoms. In another example, the patient may demonstrate a combination of described risk factors (e.g., elevated SNS tone, high CAR, glucocorticoid resistance, elevated levels of CRP, low levels of central NPY, having experienced depressive episodes and/or anxiety attacks, history of child abuse or trauma, and/or family history of anxiety disorder, depression and/or other mental illness, etc.) and currently be experiencing chronic and/or excessive psychological stress (e.g., experiencing major life change, a difficult relationship, illness or disease of self or loved one, death of loved one, occupational stress, etc.).

In particular embodiments, patients having an increased risk of developing a moderate or severe sleep disorder may have, for example, mild or acute sleep dysfunction-associated symptoms and demonstrate one or more of the following risk factors: (1) occasions of difficulty falling asleep, episodes of night awakening, occasional snoring, falling asleep during the day, occasional leg restlessness, impaired concentration, irritability, and increased muscle aches or soreness, (2) previously experienced traumatic events or experiences, (3) personal history of a sleep disorder, (4) family history of depression, anxiety disorder or other mental illness, (5) prior diagnosis of acute stress disorder, (6) prior diagnosis of any mood disorder (e.g., depression, anxiety, bipolar, panic disorder, etc.), and/or (7) depression symptoms (e.g., depressed mood for most of the day, anhedonia, psychomotor agitation or retardation nearly every day, anergia, poor appetite or overeating, low self-esteem or feelings of worthlessness, changes in cognitive ability, and/or negative feelings about self or the world). Further risk factors for the development of a sleep disorder in patients can include physiological markers such as elevated SNS activity (e.g., increased levels of catecholamines as detected in urine or plasma), elevated cortisol levels, low central nervous system NPY levels, glucocorticoid resistance (e.g., as assessed via dexamethasone suppression test), elevated CAR, low heart rate variability, elevated MSBP, limited or no "dipping" of nocturnal blood pressure, low baroreceptor sensitivity (e.g., an assessment of cardiovascular autonomic neuropathy), and/or elevated levels of serum inflammatory cytokine levels. A patient at-risk of developing a sleep disorder may be hypertensive or pre-hypertensive and/or show elevated SNS tone in the form of blood pressure dysregulation (e.g., elevated 24-hour blood pressure variability). However, in many instances, patients having a sleep disorder or being at-risk of developing a sleep disorder can have normal blood pressure levels (e.g., do not have hypertension or pre-hypertension).

In some embodiments of the present technology, the patient can have a calculated risk score for (i) determining a sleep disorder status (e.g., diagnosis, severity, etc.) or (ii) the prediction of developing a sleep disorder that is above a threshold sleep disorder risk score. Such a calculated sleep disorder risk score can indicate a likelihood of a sleep disorder diagnosis or, in another embodiment, a likelihood of developing a sleep disorder. In one embodiment, for example, a calculated sleep disorder risk score for determining a sleep disorder status can be based upon one or more data sets known in the art. For example, a sleep disorder risk score based upon the Pittsburgh Sleep Quality Assessment (PSQI). The PSQI, among other assessment tools, can be used to establish a sleep disorder risk score for determining a sleep disorder status (e.g., diagnosis/severity), and can be based upon an analysis of the patient's assessment across multiple possible risk factors. For example, the patient can be queried and assessed for core sleep dysfunction-associated symptoms indicated in the DSM-5 and the International Statistical Classification of Diseases and Related Health Problems (ICD-10) classification systems to determine if a patient has a mild, moderate, or severe sleep disorder. One of ordinary skill in the art will recognize that the PSQI scale study is only one study in which a risk score calculation can be developed and applied. Other published data sources documenting multiple possible risk factors and corresponding scores may use any of many well described techniques. Such techniques for developing tools to calculate a sleep disorder risk score could be empirical, based on multivariate regression, or using artificial intelligence (e.g. Bayesian probability, machine learning, etc.) among other techniques known in the art.

In other embodiments, a patient presenting a high or increased risk of developing a sleep disorder can have a genetic disorder or determined genetic pre-disposition to developing a sleep or other associated mental disorder. For example, specific forms (e.g., polymorphisms) of the glucocorticoid receptor gene, NR3C1, affect glucocorticoid sensitivity and additional polymorphisms in the gene known as FKBP5, a co-chaperone of the glucocorticoid receptor, is associated with increased glucocorticoid resistance and increased risk for sleep-related disorders. Additionally, carriers of polymorphisms in the genes encoding for the CRH receptor 1 are associated with an increased likelihood of developing a sleep or mood disorder. As evidence has suggested that genotype, gene methylation, histone deacetylation, and gene expression differences among other epigenetic factors, influence or accompany the development of sleep disorders, these genetic profiles can be screened to determine patients presenting certain genetic pre-dispositions associated with high or increased risk of developing a sleep disorder.

A patient suspected of having a sleep disorder can be evaluated for a level of dysfunction or severity of symptoms and/or sequelae associated with sleep disorders. Evaluation of core symptoms (e.g., difficulty in falling asleep, waking in the middle of the night or early morning, waking to use the bathroom, snoring and/or coughing, unable to breath comfortably, too cold or hot, experiencing bad dreams, experiencing pain, needing medication to fall asleep, feeling sad, feeling nervous or anxious, experiencing restless legs before or during sleep, difficulty staying awake during the day, experiencing difficulty in maintaining enthusiasm in activities or hobbies, etc.), can include a self-reporting or assessment of changes from a person's usual level of function (e.g., prior to on-set of symptoms) to a current condition. Evaluation input may also come from trusted sources (e.g., trusted family members, friends, primary physician, etc.) that can provide information on changes in performance on daily activities, job/employment performance, behavior or mood changes, sleep patterns, as well as angry outbursts, irritability or aggression and/or other risky or destructive behaviors, etc.

Physicians or other qualified clinicians may also administer one or more questionnaires or diagnostic tests, such as screening tools, to assess sleep disorder risk, severity and diagnosis. Sleep quality screening tools such as the PSQI, ESS, ISDI, MEQ, HADS, PHQ-ADS, a VAS, MSLT and/or a polysomnography, among others, as well as other screening instruments that look at multiple risk factors for predicting the patient-specific clinical features along with sleep disorder status can be utilized in the assessment process. One of ordinary skill in the art will recognize other sleep tests and scales that can be used to determine the status of sleep dysfunction of a patient. In some embodiments, for example, a patient may be suspected of having a sleep disorder based upon a single test score or outcome, combined test scores from multiple tests, or one or more test scores from multiple tests. Diagnosis can be made based upon, for example, meeting or exceeding a threshold test score. In other embodiments, a patient may demonstrate an increase in symptom severity as reflected in test scores taken over time. For example, a particular patient may show an increase in sleep disorder risk via a result in a test score between taking tests two weeks after on-set of symptoms, one month after on-set of symptoms, six months after on-set of symptoms, and a year or more after on-set of symptoms. Cognitive functioning (e.g., cerebral activities encompassing reasoning, memory, attention, and language), emotional/social functioning (e.g., traits and abilities involving positive and negative aspects of social and emotional life like empathy, interpreting emotion, speed and intensity of emotion generation, and efficacy of coping with negative emotions, etc.), and sleep-dysfunction-associated symptoms, as well as other data that can be collected in an evaluation of a patient, are based on self-report, observational (behavioral), or psychological data.

In a particular example, if a patient could respond (or a clinician could so indicate with respect to a patient) in affirmation (i.e., answering "yes") and/or if the a patient can indicate at least a moderate level of severity to one or more of the following statements, then the patient could be diagnosed with a sleep disorder and, in some embodiments, be treated with renal neuromodulation to treat the sleep disorder: Over the past month, and at a frequency of less than once a week, once or twice a week, or three or more times a week.
1. You cannot get to sleep within 30 minutes.
2. You wake up in the middle of the night or early morning.
3. You have to get up to use the bathroom during the night.
4. You cannot breathe comfortably while sleeping.
5. You cough or snore loudly while sleeping.
6. You feel too cold and/or hot while sleeping.
7. You have bad dreams while sleeping.
8. You experience pain during the night.
9. During the past month, you have had to take medicine (over-the-counter or prescribed) to help you sleep.
10. During the past month, you have had trouble staying awake while driving, eating meals, or engaging in social activity.
11. During the past month, it has been a problem for you to keep up enthusiasm to get things done.

Additional screening tools or sleep disorder risk score calculating tools may ask additional questions to identify the presence or absence of known sleep disorder risk factors. For example, a patient may be asked to respond to one or more of the following questions in an assessment:
Do you use alcohol to help you sleep?
Do you have any medical conditions that disrupt your sleep?
Have you lost interest in hobbies or activities?
Do you feel sad, irritable, or hopeless?
Do you feel nervous or worried?
Do you think something is wrong with your body?
Are you a shift worker or is your sleep schedule irregular?
Are your legs restless and/or uncomfortable before bed?
Have you been told that you are restless or that you kick your legs in your sleep?
Do you talk or walk in your sleep?
Has anyone said that you stop breathing, gasp, snort, or choke in your sleep?
Do you have a personal or family history of a sleep disorder or mental illness?
How many adverse life events (e.g., major illness, abuse, loss of a loved one, unemployment, psychological trauma, etc.) have you experienced that has caused you either high levels of stress or chronic (e.g., greater than one year) stress?
Did you experience traumatic life events and/or abuse as a child or adolescent?

Physicians or other qualified clinicians may also administer one or more questionnaires or diagnostic tests, such as screening tools, to assess depression symptoms that may accompany core sleep disorder symptoms. For example, the Patient Health Questionnaire (PHQ-2) scale is a two-item depression screener as exemplified in the following questions:
1. Have you ever had a period of two weeks or longer when you were feeling depressed or down most of the day or nearly every day?
2. Have you ever had a period of two weeks or longer when you were uninterested in most things or unable to enjoy things you used to do?

A patient having sleep disorder symptoms and one or more depression symptoms can be a candidate for renal neuromodulation.

In addition to self-reporting, observational, or other psychological data, a patient may also be evaluated for physiological data. Accordingly, a patient may demonstrate one or more physiological parameters associated with a sleep disorder or, in other embodiments, with chronic psychological stress. Non-limiting examples of sleep-associated physiological parameters may include low heart rate variability (e.g., as assessed by Standard Deviation NN intervals (SDNN)), decreased baroreceptor sensitivity (as an assessment of cardiovascular autonomic neuropathy), heightened heart rate responses to stimuli/stress (e.g., via Stroop Color Test or Cold Pressor Test), elevated muscle sympathetic nerve activity (MSNA; a marker of SNS activity), elevated systolic blood pressure, increased MSBP, lack of or low levels of nocturnal blood pressure "dipping", higher skin conductance (e.g., a measure of sweat activity thought to be under SNS influence), higher resting heart rate, disrupted sleep patterns or low quality sleep, elevated peripheral inflammatory markers (e.g., IL-6, IL-8, CRP, TNF-α, etc.), low NPY levels (e.g., in the CNS and plasma), and other measures of sympathetic activity (e.g., increased renal and/or total body norepinephrine spillover, increased plasma norepinephrine levels, increased urine levels of norepinephrine and metabolites thereof, etc.). Further physiological parameters that can be risk factors for a sleep disorder may include increased cortisol levels, glucocorticoid resistance (e.g., as assessed via dexamethasone suppression test), previous traumatic brain injury (TBI), and/or decreased levels of neurotransmitter receptors (e.g., GABA, 5-HT/serotonin, dopamine) in the brain (e.g., as assessed via administered radioligands followed by positron emission tomography (PET)).

In accordance with aspects of the present technology, patients presenting with one or more risk factors for having a sleep disorder, having a calculated sleep disorder risk score, and/or one or more risk factors for developing a sleep disorder can be candidates for treatment for a sleep disorder. In other embodiments, some patients may also be candidates for renal neuromodulation for the prevention of developing a sleep disorder in the patient. As noted above, renal neuromodulation is expected to efficaciously treat a sleep disorder including one or more symptoms associated with a sleep disorder. Renal neuromodulation is also expected to efficaciously prevent an incidence of, reduce a severity of, or slow a progression of a sleep disorder. Renal neuromodulation is further expected to improve a patient's calculated sleep disorder risk score correlating to a sleep disorder status/diagnosis.

In certain embodiments, for example, renal neuromodulation treats several clinical conditions characterized by increased overall sympathetic activity and, in particular, conditions associated with central sympathetic overstimulation such as pre-hypertension, hypertension, blood pressure variability, heart rate variability, vascular disease (e.g., vessel stiffening), metabolic syndrome, insulin resistance, diabetes, cancer, cognitive impairment (e.g., which can progress to dementia), systemic inflammation, depression, and anxiety disorder, among others, that may be associated with and/or contribute to a severity or progression of a sleep disorder in a patient. The reduction of afferent neural signals typically contribute to the systemic reduction of sympathetic tone/drive, and renal neuromodulation is expected to be useful in treating several conditions associated with systemic sympathetic overactivity or hyperactivity. For example, and in accordance with other aspects of the present technology, patients presenting with one or more risk factors for having a sleep disorder and/or having a positive clinical diagnosis for a sleep disorder can be candidates for renal neuromodulation treatment for preventing, reducing an incidence of, and/or reducing a severity of a cardiovascular condition (e.g., coronary heart disease, MI, left ventricular hypertrophy, ventricular arrhythmias, etc.) and/or stroke (e.g., acute ischemic stroke, lacunar stroke, transient ischemic attack (TIA), hemorrhagic stroke, etc.) in the patient. In other embodiments, treating patients having a sleep disorder in younger (e.g., 18-40 years of age) or in middle-aged (e.g., 40-65 years of age) patients may reduce an incidence of or improve an outcome of many comorbid conditions and diseases including, but not limited to, cardiovascular disease, stroke, metabolic disorders, diabetes, elevated cholesterol, obesity, cancer, dementia, etc. Accordingly, in particular examples, patients having or at risk of having a sleep disorder and who are suitable candidates for treatment via renal neuromodulation can be between the ages of 18 and 45, between the ages of 18 and 30, between the ages of 20 and 40, or between the ages of 20 and 35. In other embodiments, the patients may be between the ages of 35 and 65, between the ages of 45 and 65, between the ages of 50 and 70, or the patient can be at least 35 years old, or at least 18 years old.

II. RENAL NEUROMODULATION FOR TREATING SLEEP DISORDERS AND/OR REDUCING A RISK ASSOCIATED WITH THE DEVELOPMENT OF A SLEEP DISORDER

Therapeutically-effective renal neuromodulation can be used for the treatment of a sleep disorder or for the treatment of one or more symptoms and/or sequelae associated with a sleep disorder, the management of a sleep disorder, or to reduce an incidence of a sleep disorder in patients identified as having a risk of developing a sleep disorder at a future time. In further embodiments, therapeutically-effective renal neuromodulation can be used for treating a patient (e.g., a patient having one or more risk factors associated with developing a sleep disorder) prior to the development of one or more comorbid conditions (e.g., substance and alcohol abuse/addiction, depression and/or depressive disorder, psychotic and/or personality disorders, cardiovascular disease, stroke, hypertension, obesity (e.g., high BMI), metabolic disorders, such as type 2 diabetes, cancer, and cognitive impairment (e.g., leading to dementia), etc.) and for reducing a risk associated with developing a sleep disorder.

In other embodiments, therapeutically-effective renal neuromodulation can be used to treat sleep disorder patients or patients diagnosed with a sleep disorder to reduce an incidence of cardiovascular disease (e.g., coronary heart disease, etc.) or a cardiovascular event (e.g., MI, stroke, etc.) in the patient. In further embodiments, therapeutically-effective renal neuromodulation can be used for treating a patient having a sleep disorder to improve one or more parameters associated with cardiovascular health, or to reduce a severity of a cardiovascular condition.

While sympathetic drive regulation can have adaptive utility in maintaining homeostasis or in preparing many organs in the body for a rapid response to environmental factors, chronic activation of the SNS (e.g., associated with acute stress syndrome, chronic stress, primary aging, age-associated obesity, etc.) is a common maladaptive response that can contribute to diseases/conditions (e.g., hypertension, systemic or localized inflammation, vascular remodeling, atherosclerosis, obesity, insulin resistance, metabolic syndrome, etc.) or predispose individuals to psychophysiological adaptations that can increase a patient's risk of developing a sleep disorder and/or drive progression and/or severity of a sleep disorder in a patient. Excessive activation of the renal sympathetic nerves in particular has been identified experimentally and in humans as a likely contributor to the complex pathophysiology of hypertension, states of volume overload (such as heart failure), systemic inflammation, and progressive renal disease. As examples, radiotracer dilution has demonstrated increased renal norepinephrine spillover rates in patients with essential hypertension.

Aspects of the present technology include targeting renal nerve fibers for neuromodulation in patients (1) having been diagnosed with a sleep disorder, (2) demonstrating one more physiological and/or psychological symptoms associated with a sleep disorder, and/or (3) having an increased risk associated with developing a sleep disorder. Targeting renal nerve fibers for neuromodulation in patients can effectively attenuate neural traffic along the sympathetic nerves. Without being bound by theory, attenuation of neural traffic along renal sympathetic nerves can be used, for example, to treat or prohibit one or more hallmark symptoms associated with a sleep disorder, decrease systemic inflammatory responses associated with a sleep disorder, and/or decrease a level of severity of a sleep disorder and/or reduce a number of symptoms associated with a sleep disorder in the patient. In some embodiments, hallmark symptoms of a sleep disorder that can be treated, reduced or prevented via attenuation of neural traffic along renal sympathetic nerves can include, for example, difficulty in getting to sleep, difficulty in maintaining sleep, snoring loudly, having bad dreams, feeling too hot or cold, having difficulty breathing comfortably while sleeping, experiencing night pain, requiring medication to sleep, drinking alcohol to fall asleep, feeling fatigued or sleepy while driving or eating meals or engaging in social activities, sleepwalking, impaired concentration, excessive sleeping (e.g., hypersomnia), irritability, excessive anxiety and worry, depression-related symptoms (e.g., sadness, loss of hope, etc.), and undesirable elevations in heart rate, blood pressure, and inflammation. In yet another embodiment, attenuation of neural traffic along renal sympathetic nerves in an individual having one or more risk factors associated with developing a sleep disorder can be used for reducing a risk associated with developing a sleep disorder.

As discussed above, several diseases and conditions have high comorbidity with a sleep disorder diagnosis, including, for example, substance and alcohol abuse/addiction, depression and/or depressive disorder, anxiety disorder (e.g., general anxiety disorder, social anxiety disorder), PTSD, psychotic and/or personality disorders, cardiovascular disease, stroke, hypertension, obesity (e.g., high BMI), metabolic disorders, such as type 2 diabetes, cancer, chronic kidney disease, peripheral artery disease, and cognitive impairment (e.g., leading to dementia). In certain embodiments, patients having a sleep disorder and one or more comorbid conditions and/or diseases can be treated with renal neuromodulation to treat and/or reduce severity of the sleep disorder and/or the one or more comorbid conditions/diseases. In another example, renal neuromodulation can be used to therapeutically treat a patient diagnosed with a sleep disorder for preventing and/or reducing an incidence of developing one or more comorbid conditions/diseases, including those conditions/diseases wherein chronic SNS activity is known to be a contributing factor (e.g., hypertension, cardiovascular disease, etc.).

In one example, renal neuromodulation can be used to reduce a patient's systolic blood pressure, including a MSBP and/or a nocturnal blood pressure level. In another example, renal neuromodulation can be used to increase heart rate variability (e.g., the beat-to-beat fluctuations in heart rate) in a patient. In other embodiments, attenuation of neural traffic along renal sympathetic nerves can be used to treat or prevent metabolic disorders, obesity and/or insulin resistance in the patient having a sleep disorder or at increased risk associated with developing a sleep disorder. In yet a further embodiment, renal neuromodulation can be used to lower one or more levels of inflammatory biomarkers in a patient.

Certain effects of chronic SNS activation (such as resulting from chronic psychological stress) that take place prior to experiencing sleep dysfunction-associated symptoms may be associated with an increased risk of developing a sleep disorder. Many of these effects may not yield noticeable signs or symptoms associated with a disease; however, the effects of chronic SNS activation can cause unseen damage to cardiac tissue, brain tissue, and/or vascular tissue, as well as disrupt normal neurophysiological and hormonal balances throughout the body prior to the appearance of quantifiable disease indicators typically associated with maladaptive SNS activation and/or prior to exposure to experiencing sleep dysfunction-associated symptoms in the predisposed or at-risk individual. Accordingly, in one embodiment, neuromodulation treatment can be used to treat patients having a high risk of developing a sleep disorder. For example, patients may present one or more risk factors for developing a sleep disorder (e.g., having been diagnosed with chronic stress, having an elevated heart rate, having reduced heart rate variability, having elevated cortisol levels and/or CRH levels, presenting with glucocorticoid resistance, elevated CAR, low levels of central NPY, having elevated systemic plasma levels of inflammatory biomarkers (e.g., IL-6, IL-8, TNF-α, CRP, etc.), having high blood pressure, having a genetic predisposition (e.g., polymorphisms in genes encoding for NR3C1, FKBP5, CRHR1, TNF-α, etc.). In other examples, such patients having a high risk of developing a sleep disorder may present one or more social or demographic risk factors for the development of a sleep disorder (e.g., adverse childhood experience(s), prior traumatic brain injury, personal or family history of having a sleep disorder, depression or mental illness, anxiety disorder, experiencing adverse life events, prior exposure to trauma, history of substance abuse, being in a stressful situation or relationship, smoker, physically inactive, etc.).

In still further embodiments, neuromodulation treatment can be used to treat patients for improving a sleep disorder risk score for a patient diagnosed with a sleep disorder. Such a risk score may be determined, for example, using a sleep quality screening tool for determining a severity of a sleep disorder in the patient. For example, certain patients can have a sleep disorder risk score above a threshold sleep disorder risk score, can have one or more sleep disorder risk factors, have a combination of sleep disorder risk factors, etc., and renal neuromodulation can be used to therapeutically reduce (a) systemic plasma levels of norepinephrine from, e.g., spillover from innervation of smooth muscle surrounding blood vessels, (b) systemic plasma levels of inflammatory biomarkers (e.g., IL-6, IL-8, TNF-α, CRP, etc.), and/or (c) high blood pressure. In other embodiments, neuromodulation treatment can be used to increase heart rate variability or decrease MSBP in patients.

In one embodiment, a patient having extreme or chronic psychological/mental stress in response to an adverse life event or condition and presenting with one or more acute stress indicators or other indicators, such as pre-hypertension (e.g., systolic BP of 120-139 mmHg/diastolic BP of 80-89 mmHg), hypertension (e.g., systolic BP>140 mmHg/ diastolic BP>90 mmHg), increased serum levels of IL-6 or CRP, higher levels of glucocorticoid (e.g., cortisol), higher CAR, higher MSBP, decreased heart rate variability, or having other factors presenting an increased risk of developing a sleep disorder (e.g., persons having experienced a traumatic brain injury, having experienced traumatic events, adverse childhood, family history of mental illness, sleep disorder-associated genetic polymorphisms, etc.) can be treated with renal neuromodulation to reduce a level of renal sympathetic drive and/or reduce a level of systemic norepinephrine spillover in circulating plasma (Schlaich, M. P., et al., *Frontiers in Physiology,* 2012, 3(10): 1-7).

In some embodiments, a patient demonstrating chronic stress indicators for greater than 1 year and presenting with sleep dysfunction-associated symptoms can be diagnosed with a sleep disorder by a physician or qualified clinician. In other embodiments, a patient demonstrating chronic stress indicators and sleep dysfunction-associated symptoms can present with a qualifying result on a sleep quality screening tool (e.g., tool for assessing a sleep disorder diagnosis, tool for assessing a sleep disorder risk status, etc.). In further embodiments, chronic psychological stress indicators precipitated by an adverse life condition or event can refer to patients at risk of developing a sleep disorder, and patients may be treated with renal neuromodulation to prevent a future on-set of a sleep disorder, reduce a risk factor score associated with the severity of a sleep disorder, reduce a severity of one or more symptoms associated with a sleep disorder, or reduce an incidence of developing one more comorbid conditions/diseases.

Several embodiments of the present technology utilize intravascular devices that reduce sympathetic nerve activity by applying, for example, radiofrequency (RF) energy to target nerve(s) or target site(s) in patients presenting one or more physiological symptoms associated with a sleep disorder, or having a risk of developing a sleep disorder, such as having one or more sleep disorder risk factors. In certain embodiments, neuromodulation is used to reduce renal sympathetic nerve activity in patients having a high risk (e.g., a predisposition or increased likelihood) of developing a sleep disorder, one or more signs or symptoms associated with sleep disorder development, or, in further embodiments, in patients having been diagnosed with a sleep disorder. In a particular embodiment, neuromodulation is used to reduce renal sympathetic nerve activity in patients having a sleep disorder risk score (e.g., indicating a status or severity of a sleep disorder) above a threshold risk score.

Renal neuromodulation is the partial or complete incapacitation or other effective disruption of the nerves of the kidneys, including nerves terminating in the kidneys or in structures closely associated with the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for preventing incidence of or treating a sleep disorder, reducing a severity of a sleep disorder, or for alleviating symptoms and other sequelae associated with a sleep disorder over longer periods of time, short-term modulation of the renal nerves may also be desirable. For example, some patients may benefit from short-term renal nerve modulation to address acute symptoms presenting during or following an adverse life event or condition, such as hyperarousal, social or other anxiety, PTSD, mood swings, or other stress/sleep-related behavioral changes. In particular, some patients may benefit from short-term renal nerve modulation to address a period of insomnia following a traumatic event such as, for example, an accident or natural disaster, recently serving in combat, illness, or loss of a loved one. In other instances, some patients may benefit from short-term renal nerve modulation as adjuvant therapy to increase effectiveness of co-administered drugs (e.g., anti-anxiety drugs, antidepressant drugs, anti-psychotic drugs, anti-inflammatory medications (e.g., antihistamines), anti-hypertensive drugs, and sleeping medications (e.g., sedatives) among others administered to support patients), sleeping aides (e.g., melatonin), intervention devices (e.g., continuous positive airway pressure (CPAP)) and/or psychotherapy (e.g., cognitive-behavioral therapy, interpersonal therapy, etc.).

Figure 2:
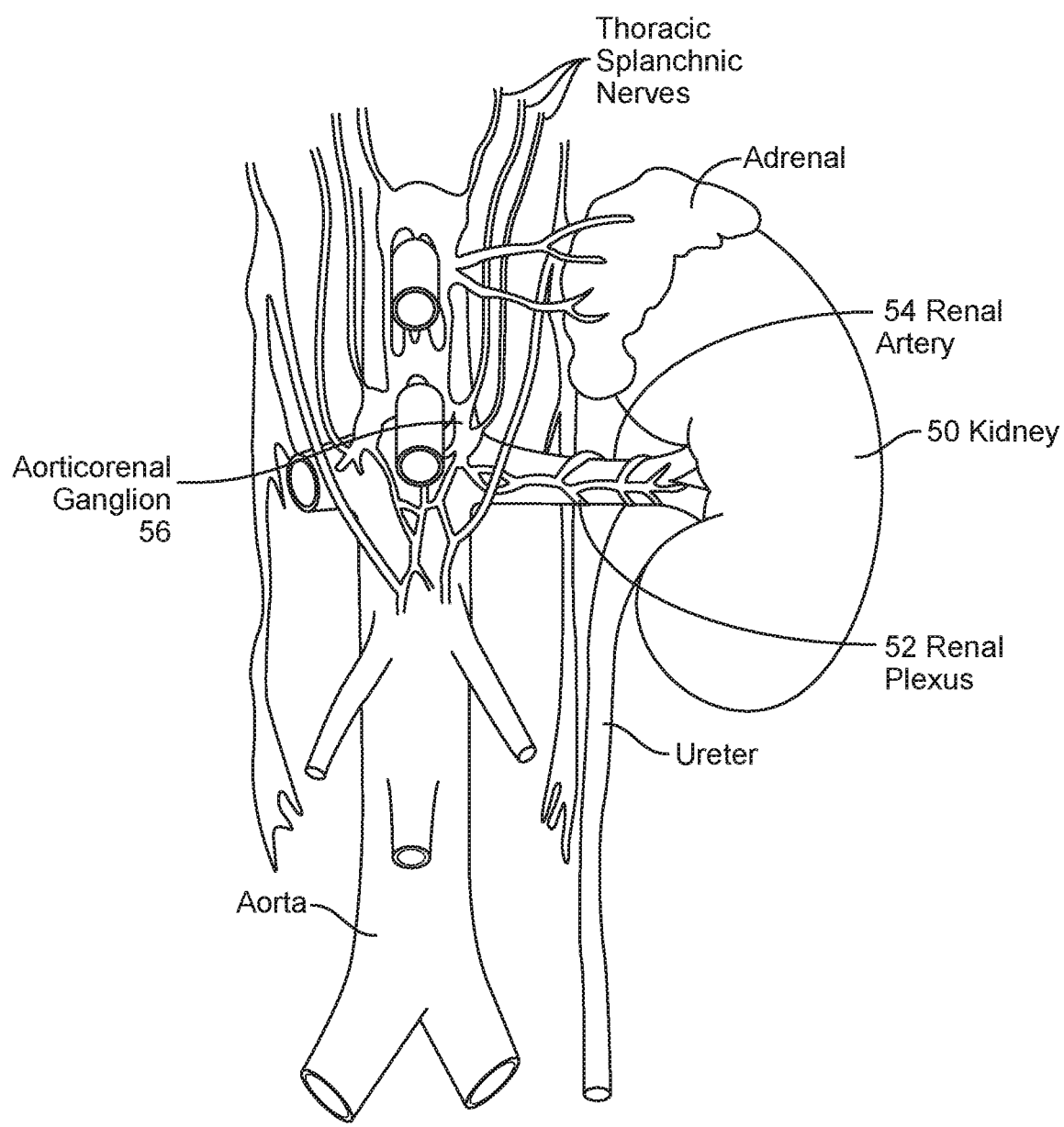
FIG. 2 is an enlarged anatomic view of nerves of a left kidney to form the renal plexus surrounding the left renal artery.

FIG. 2 is an enlarged anatomic view of nerves innervating a left kidney 50 of a patient. As FIG. 2 shows, the kidney 50 is innervated by a renal plexus 52, which is intimately associated with a renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50, innervating the kidneys while terminating in the blood vessels, the juxtaglomerular apparatus, and the renal tubules (not shown). Fibers contributing to the renal plexus 52 arise from the celiac ganglion (not shown), the superior mesenteric ganglion (not shown), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord (renal sympathetic nerves arise from T10-L2, FIG. 1). Referring to FIGS. 1 and 2 together, preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion (FIG. 1), the superior mesenteric ganglion (FIG. 1), and the aorticorenal ganglion 56 (FIG. 2). Postganglionic neuronal cell bodies exit the celiac ganglion, the superior mesenteric ganglion, and the aorticorenal ganglion 56 to the renal plexus 52 and are distributed to the renal vasculature.

It has previously been shown that stimulation of renal efferent nerves directly affects neural regulation components of renal function that are considerably stimulated in disease states characterized by heightened sympathetic tone such as, for example, increased blood pressure in hypertensive patients. As provided herein, renal neuromodulation is likely to be valuable in the treatment of a sleep disorder and/or symptoms associated with a sleep disorder. Renal neuromodulation is also likely to be valuable in the prevention of developing a sleep disorder in certain at-risk individuals (e.g., individuals having experienced adverse life events or circumstances and/or presenting one or more chronic stress indicators or biomarkers indicating a high likelihood of developing a sleep disorder).

Renal neuromodulation may also likely to be valuable in the treatment of diseases and conditions that are associated with sleep disorders and/or increased SNS tone such as, for example, cardiovascular disease, hypertension, increased blood pressure variability, systemic inflammation, endothelial dysfunction, vascular inflammation, vessel remodeling and/or hardening, atherosclerosis, and metabolic disorders among others. In particular, renal neuromodulation along the renal artery and/or within branches of the renal artery as described in U.S. patent application Ser. No. 14/839,893, filed Aug. 28, 2015 and incorporated herein by reference in its entirety, is expected to reduce renal sympathetic drive in the kidney, thereby reducing the negative impact of SNS activation on aspects of these and other conditions associated with physiological changes that have impact on psychological and cognitive health. As such, renal neuromodulation is also likely to be particularly valuable in patients having one or more clinical conditions characterized by increased overall and particularly renal sympathetic activity, such as cardiovascular disease, hypertension, increased blood pressure variability, low heart rate variability, systemic inflammation, chronic vascular inflammation, endothelial dysfunction, metabolic syndrome, insulin resistance, diabetes, anxiety disorder, and depression among others.

As the reduction of afferent neural signals contributes to the systemic reduction of sympathetic tone/drive, renal neuromodulation might also be useful in preventing a sleep disorder. For example, a reduction in central sympathetic drive may reduce and/or improve measurable physiological parameters typically associated with the development of a sleep disorder, prior to on-set of core sleep dysfunction-associated symptoms. Alternatively, a reduction in central sympathetic drive may, for example, reduce an elevated heart rate, improved blood pressure, improve heart rate variability, increase blood flow to the brain, reduce cerebrovascular inflammation, reduce systemic inflammation, and/or improve other chronic stress-related symptoms such as depression and symptoms associated with excessive anxiety (e.g., uncontrollable worrying or fear, panic attacks, etc.).

Other psychologically and/or neurologically related conditions, such as, e.g., depression and disabilities associated with excessive anxiety, as well as other conditions presented as comorbid with sleep disorders such as, for example, cardiovascular disease, stroke, hypertension, chronic kidney disease, high BMI (e.g., obesity), metabolic disorder (e.g., diabetes) and substance and/or alcohol abuse, may also be treatable or preventable in sleep disorder patients using renal neuromodulation. In some instances, therapeutically-effective renal neuromodulation may improve one or more measurable physiological parameters associated with a comorbid disease or condition in the patient without substantially improving the sleep disorder in the patient.

Intravascular devices that reduce sympathetic nerve activity by applying, for example, RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in patients with a sleep disorder and increased levels of peripheral inflammatory markers, such as IL-6 and CRP, in patients with a sleep disorder experiencing a host of inflammatory challenges.

Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radio frequency (RF) ablation) have been shown to be efficacious in reducing blood pressure, decreasing blood pressure variability, decreasing nocturnal blood pressure, reducing MSBP, improving arterial stiffness and reducing mediators of systemic inflammation in patients with treatment-resistant hypertension.

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of a renal blood vessel (e.g., renal artery, renal arterial branch, renal ostium, renal vein) and adjacent regions of the renal plexus RP, which lay intimately within or adjacent to the adventitia of the renal blood vessel. Some embodiments of the present technology, for example, include electrode-based or transducer-based approaches, which can be used for therapeutically-effective neuromodulation. For example, an energy delivery element (e.g., electrode) can be configured to deliver electrical and/or thermal energy at a treatment site.

By way of theory, targeting both general afferent and efferent renal sympathetic nerves (e.g., via a catheter-based approach, utilizing extracorporeal ultrasound) may cause beneficial effects extending well beyond affecting a severity of a sleep disorder or a risk associated with developing a sleep disorder, such as reducing a risk of developing hypertension, stroke, cardiovascular disease, obesity, metabolic disorder or other end organ damage. As discussed herein, a correlation between hyperactivity of the SNS and an increased risk of developing a sleep disorder and an increased risk in promoting more severe sleep dysfunction-associated symptoms has been implicated. There is now also evidence that a sleep disorder and related symptom severity is associated with chronic inflammatory responses and sympathetic activation appears to affect serum levels of peripheral inflammatory markers. Additionally, chronic stress, obesity and other cardiovascular maladies promote hyperactivity (e.g., overactivity) of the sympathetic nervous system throughout the body. For example, when experiencing stress, including chronic stress, hormonal and neural information (e.g., sensory afferent input) is received by the CNS, which in turn further elevates sympathetic tone via efferent signaling throughout the body. Some aspects of methods of treating patients having a sleep disorder or having one or more risk factors, including a high risk score, for the development of a sleep disorder, using sympathetic neuromodulation are at least in part derived from the recognition described herein that the kidneys may contribute to elevated central sympathetic drive.

Several aspects of the current technology are configured to reduce renal sympathetic nerve activity within or near the kidney(s) to reduce localized release of norepinephrine. Several properties of the renal vasculature may inform the design of treatment devices and associated methods for achieving target sympathetic neuromodulation, for example, via intravascular access, and impose specific design requirements for such devices. Specific design requirements for renal neuromodulation may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively modulating the renal nerves with the neuromodulatory apparatus.

Intravascular devices that reduce sympathetic nerve activity by applying, for example, RF energy to a treatment site in the renal artery have recently been shown to reduce renal sympathetic drive, renal norepinephrine spillover, and whole body norepinephrine spillover. Renal neuromodulation is expected to reduce renal sympathetic neural activity, and since the reduction of afferent neural signals contributes to the systemic reduction of sympathetic tone/drive, renal neuromodulation is a useful technique in addressing certain risk factors and symptoms associated with a sleep disorder that are attributable to systemic sympathetic hyperactivity. For example, as previously discussed, a reduction in central sympathetic drive may treat a sleep disorder including reducing a severity of one or more symptoms associated with a sleep disorder, reduce a likelihood of developing a sleep disorder, as well as improve other comorbid disease manifestations (e.g., hypertension, cardiovascular disease, stroke, metabolic disorders, insulin resistance, diabetes, systemic inflammation, depression, etc.) associated with sympathetic hyperactivity.

Accordingly, renal neuromodulation is expected to be useful in treating a sleep disorder, reducing a severity of one or more symptoms in patients afflicted with a sleep disorder, preventing and/or treating one or more comorbid conditions or diseases associated with a sleep disorder or preventing an incidence of developing a sleep disorder in patients presenting certain risk factors. The beneficial effect of renal neuromodulation with respect to a risk associated with development of a sleep disorder is expected to apply to patients who do not currently meet the diagnostic standard for a sleep disorder diagnosis (e.g., under DSM-5), for example, regardless of the baseline renal sympathetic neural activity or the baseline level of norepinephrine in plasma (e.g., whole body norepinephrine spillover). For example, renal neuromodulation in accordance with embodiments of the present technology can improve one or more measurable physiological parameters corresponding to a sleep disorder risk factor or status (e.g., level of severity of diagnosis) in the patient when baseline renal sympathetic neural activity is normal, below normal, or above normal (e.g., hyperactive or overactive). Likewise, renal neuromodulation in accordance with additional embodiments of the present technology can improve one or more measurable physiological parameters corresponding to a sleep disorder risk factor or a sleep disorder status (e.g., level of severity of diagnosis) in the patient when baseline central sympathetic drive, baseline norepinephrine spillover in plasma, and/or whole body norepinephrine spillover is normal, below normal, or above normal (e.g., hyperactive or overactive). Such an improvement in one or more measurable physiological parameters corresponding to a sleep disorder risk factor or a sleep disorder status (e.g., level of severity of diagnosis) in the patient can reduce a risk associated with developing a sleep disorder in that patient or can reduce symptom severity and/or effectively treat an afflicted patient diagnosed with a sleep disorder.

III. METHODS FOR TREATING SLEEP DISORDERS AND/OR REDUCING A RISK ASSOCIATED WITH DEVELOPING A SLEEP DISORDER AND RELATED CONDITIONS

Disclosed herein are several embodiments of methods directed to treating an incidence of a sleep disorder in a patient using catheter-based renal neuromodulation. Further embodiments disclosed herein are directed to preventing an incidence of a sleep disorder and/or other conditions associated with an increased risk of developing a sleep disorder in a patient using catheter-based renal neuromodulation. The methods disclosed herein may represent various advantages over a number of conventional approaches and techniques in that they allow for the potential targeting of elevated sympathetic drive, which may either be a cause of several neurological, immune vascular, or other physiological risk factors associated with a sleep disorder or a key mediator of the disorder manifestation. Also, the disclosed methods provide for localized treatment and limited duration treatment regimens (e.g., one-time treatment), thereby reducing patient long-term treatment compliance issues.

In certain embodiments, the methods provided herein comprise performing renal neuromodulation, thereby decreasing sympathetic renal nerve activity, for example, for the purposes of being able to provide one or more of a reduction in a number of sleep disorder risk factors, a reduction in severity of one or more sleep disorder risk factors, a reduction in a calculated sleep disorder risk score, a reversal in vascular damage facilitated by sympathetic activity, or a reduction in systemic inflammation. For example, renal neuromodulation is expected to reduce a level of central sympathetic activity that may contribute to one more underlying causes of sleep disorders.

Renal neuromodulation may be repeated one or more times at various intervals until a desired sympathetic nerve activity level or another therapeutic benchmark is reached. In one embodiment, for example, a decrease in sympathetic nerve activity may be observed via a marker of sympathetic nerve activity in patients, such as decreased levels of plasma norepinephrine (noradrenaline), changes in levels of systemic renin in plasma, changes in levels of angiotensin II in plasma, and/or changes in levels of systemic aldosterone in plasma. Other measures or markers of sympathetic nerve activity can include MSNA, norepinephrine spillover, and/or heart rate variability. In some instances, a decrease in SNS activity can be observed as a decrease in norepinephrine and metabolites thereof (e.g., vanillomandelic acid (VMA)) in urine. In another embodiment, other measurable physiological parameters or markers, such as improved baroreceptor sensitivity, improved heart rate responses to stimuli/stress, improved heart rate variability, improved skin conductance, improved blood pressure control (e.g., lower blood pressure), improved blood pressure variability (e.g., improved MSBP, improved nocturnal blood pressure "dipping"), lower levels of peripheral inflammatory biomarkers (e.g., IL-6, IL-8, TNF-α, CRP, etc.), improved levels of NPY, reduced cortisol levels, reduced CAR, reduced glucocorticoid resistance, improved brain neural activity (e.g., in the hippocampus and other brain regions), changes in aldosterone-to-renin ratio (ARR), changes in a salt suppression test, changes in blood plasma levels of potassium, improved blood glucose regulation, etc., can be used to assess efficacy of the thermal modulation treatment for patients diagnosed as having a sleep disorder or for patients having one or more risk factors for developing a sleep disorder, and/or having a calculated sleep disorder risk score above a threshold sleep disorder risk score. In certain embodiments, renal neuromodulation may be repeated one or more times at various intervals until a desired sympathetic nerve activity level or another therapeutic benchmark is reached for such patients.

In certain embodiments of the methods provided herein, renal neuromodulation is expected to result in a change in sympathetic nerve activity and/or in other measurable physiological parameters or markers, over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months, 12 months or 24 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

In one embodiment, measured norepinephrine content (e.g., assessed via tissue biopsy, assessed in real-time via intravascular blood collection techniques, assessed in real-time via urine, etc.) can be reduced (e.g., at least about 5%, 10%, 20% or by at least 40%) in the patient within, for example, about three months after at least partially inhibiting sympathetic neural activity in nerves proximate a renal blood vessel.

In one embodiment, renal neuromodulation may be performed on a patient having one or more risk factors or symptoms associated with a sleep disorder to improve the physiological state of at least one of the sleep disorder risk factors. In some embodiments, for example, renal neuromodulation may result in a reduction in a patient's heart rate under stress, may raise heart rate variability, lower a MSBP, lower a nocturnal blood pressure level, reduce systolic blood pressure, reduce blood pressure variability, increase baroreceptor sensitivity, lower skin conductance, reduce a serum level of an inflammatory biomarker, or reduce a level of insulin resistance. In a particular example, a patient having a sleep disorder and decreased heart rate variability (e.g., SDNN<50 ms) may have heart rate variability within a normal range (e.g., SDNN>50 ms) after a neuromodulation procedure. In a further example, a reduction in MSBP can be, for example, by at least about 5%, 10% or a greater amount as determined by average ambulatory blood pressure analysis before and after (e.g., 1, 3, 6, or 12 months after) a renal neuromodulation procedure. Likewise, and in yet a further example, a reduction in nocturnal blood pressure level can be, for example, by at least about 5%, 10%, or a greater amount as determined by average ambulatory blood pressure analysis before and after (e.g., 1, 3, 6, or 12 months after) a renal neuromodulation procedure.

In the case of systemic inflammation and/or a patient having elevated serum levels of inflammatory biomarkers, IL-6, IL-8, TNF-α and/or CRP, renal neuromodulation may improve (e.g., reduce a level of) markers of inflammation (e.g., IL-6, IL-8, TNF-α, CRP), and in some embodiments, provide a reduction in biomarker level, for example, by about 5%, 10%, 25%, 45% or a greater amount as determined by blood analysis before and after (e.g., 1, 3, 6, or 12 months after) a renal neuromodulation procedure. In an example where the patient has elevated cortisol levels, elevated CRH levels, and/or glucocorticoid resistance, renal neuromodulation may improve (e.g., reduce a level of) cortisol levels, CRH levels, and/or glucocorticoid resistance by about 5%, about 10%, about 20% or greater amount as determined by quantitative analysis (e.g., dexamethasone binding assay, dexamethasone suppression test, radioimmunoassay, CRH stimulation test, etc.). In other embodiments, and in particular afflicted patients, renal neuromodulation may increase arteriole blood flow, reduce a level of atherosclerosis, or reduce a degree of arterial stiffening in the patient by about 5%, 10% or a greater amount as determined by qualitative or quantitative analysis (e.g., computerized tomography (CT) scan, pulse wave velocity (PWV) analysis, angiography, etc.) before and after (e.g., 1, 3, 6, or 12 months after) a renal neuromodulation procedure.

In another embodiment, renal neuromodulation may be performed on a patient having a calculated sleep disorder risk score associated with a sleep disorder status in the patient that is above a threshold sleep disorder risk score. Renal neuromodulation is expected to therapeutically improve the patient's sleep disorder risk score and thereby reduce, diminish, reverse or eliminate the sleep disorder in the patient. In one embodiment, a threshold sleep disorder risk score may be a theoretical risk score (e.g., based on population studies) that represents a cut-off score for a sleep disorder diagnosis. In other embodiments, the threshold sleep disorder risk score may be a theoretical risk score that represents an upper limit of acceptable severity and/or acceptable risk of developing a sleep disorder.

In a particular example, a patient may be assessed for a number of factors that have been previously determined to validate a sleep disorder diagnosis and/or to carry risk for the development of a sleep disorder (e.g., number or severity of core sleep dysfunction-associated symptoms, genetic/epigenetic factors, number or duration of adverse life events or circumstances the patient has experienced, number of prior traumatic events the patient experienced, prior brain injury, presence of abuse or neglect during childhood, presence of personal or family history of sleep disorders, depression or mental illness, history of anxiety disorder, low heart rate variability, elevated cortisol levels, elevated CAR, low NPY levels, baroreceptor sensitivity, blood pressure, MSBP levels, nocturnal blood pressure levels, MSNA levels, body mass index, substance abuse/habits, etc.). Using a sleep disorder risk score calculator tool (e.g., based on epidemiological data), a patient's risk score can be assessed. For patients having a calculated sleep disorder risk score above the threshold sleep disorder risk score (e.g., signifying an undesirable level of symptom or disorder severity or probability of having a sleep disorder), a renal neuromodulation procedure is performed. Renal neuromodulation may improve (e.g., lower, reverse, reduce a rate of increase over time, etc.) the patient's sleep disorder risk score. For example, following a renal neuromodulation procedure, a patient's calculated sleep disorder risk score may reduce (e.g., improve) by about by about 5%, about 10%, about 15%, about 20%, about 25%, about 30%, about 40%, about 50%, about 75%, or a greater amount as determined by the sleep disorder risk score calculator tool. Such improvements in a patient's sleep disorder risk score may be detected, for example 1, 3, 6, 12, or 24 months after a renal neuromodulation procedure. In certain embodiments, a threshold risk score can be variable depending on a number of factors including gender, age, socioeconomic levels, geographical residence, etc. For example, a threshold risk score for a male patient can be greater than a threshold risk score for a female patient.

In addition to (or instead of) affecting one or more measurable risk factors associated with a sleep disorder or the development of a sleep disorder, renal neuromodulation may efficaciously treat one or more measurable physiological parameter(s) or sequela(e) corresponding to the progression or severity of a sleep disorder in the patient. For example, in some embodiments, renal neuromodulation may result in an improvement (e.g., prevent further decline, maintain, or improve) in a patient's cognitive abilities and/or emotional/social functioning abilities as assessed by one or more accepted diagnostic test methods (e.g., screening tools, questionnaires, etc.) for identifying sleep disorder risk, severity and diagnosis (e.g., PSQI, ESS, ISDI, MEQ, HADS, PHQ-ADS, a VAS, MSLT and/or a polysomnography, etc.). In a specific embodiment, a patient may improve a sleep quality screening test score, maintain a sleep quality screening test score, or decrease a rate of decline (e.g., rate of sleep disorder progression) in a test score over time following a renal neuromodulation procedure. Such improvements in a patient's cognitive abilities and/or emotional/social functioning abilities may be detected, for example 1, 3, 6, or 12 months after a renal neuromodulation procedure. In other embodiments, improvements are detected 2, 3, 4, 5 or 10 years after a renal neuromodulation procedure. In some embodiments, a sleep diagnostic test score can be improved by about 5%, about 10%, about 15%, about 20%, about 30%, about 40%, about 50%, or about 75%. In other embodiments, patients may report that daily activities are easier following a neuromodulation procedure.

In an example, renal neuromodulation may efficaciously treat one or more aspects of sleep disturbance associated with a sleep disorder in the patient. For example, a patient may have an improvement (e.g., a reduction) in the number, the type and/or the duration of sleep disturbances (e.g., number of nights of difficulty falling asleep, number of nights difficulty maintaining or staying asleep, duration of time it takes to fall asleep, duration of night awake, number of times patient wakes up during the night, etc.) following a renal neuromodulation procedure. Such improvements in a patient's sleep patterns and/or sleep quality may be detected, for example 1, 3, 6, or 12 months after a renal neuromodulation procedure. In other embodiments, improvements are detected 2 or 3 years after a renal neuromodulation procedure. In some embodiments, the patient's sleep quality (e.g., number of nights with sleep disturbance, time duration of sleep disturbance, etc.) can be improved by about 5%, about 10%, about 15%, about 20%, about 30%, about 40%, about 50%, or about 75% within 3 to 12 months or within 3 to 6 months following a renal neuromodulation procedure.

In a further example, renal neuromodulation may efficaciously treat additional aspects of sleep dysfunction-associated symptoms in the patient. For example, a patient may have an improvement (e.g., a reduction) in the number of instances, the type, and/or the severity of sleep-related symptoms, such as snoring loudly, having bad dreams, feeling too hot or cold, having difficulty breathing comfortably while sleeping, experiencing night pain, requiring medication to sleep, drinking alcohol to fall asleep, feeling fatigued or sleepy while driving, eating meals or engaging in social activities, sleepwalking, impaired concentration, excessive sleeping (e.g., hypersomnia), irritability, excessive anxiety and worry, depression-related symptoms (e.g., sadness, loss of hope, etc.) following a renal neuromodulation procedure. Such improvements in a patient's sleep-related symptoms may be detected, for example, 1, 3, 6, or 12 months after a renal neuromodulation procedure. In other embodiments, improvements are detected 2 or 3 years after a renal neuromodulation procedure. In some embodiments, the level of sleep-related symptoms (e.g., level of severity, number of sleep-related symptoms, the number of days the patient experiences sleep-related symptoms within a logged time period, etc.) can be improved by about 5%, about 10%, about 15%, about 20%, about 30%, about 40%, about 50%, or about 75% within, for example, 3 to 12 months or within 3 to 6 months following a renal neuromodulation procedure. In some embodiments, the patient can experience complete regression or full recovery from the sleep-related symptoms.

Renal neuromodulation may prevent or reduce an incidence of developing one or more comorbid conditions or diseases in a patient with a sleep disorder. For example a patient with a sleep disorder treated with renal neuromodulation may have a decreased likelihood of developing pre-hypertension, hypertension, cardiovascular disease, stroke risk, metabolic disorders, insulin resistance, diabetes, systemic inflammation, chronic kidney disease, peripheral artery disease, dementia, etc. In other embodiments, a patient with a sleep disorder treated with renal neuromodulation may have a decreased likelihood of developing depression, an anxiety disorder or mental disorder. In another embodiment, patients with a sleep disorder having one or more comorbid conditions or diseases may have an improvement in (e.g., reduction, maintain a level, slow a rate of progression of) in the one or more comorbid conditions or diseases and associated symptoms thereof. In a particular example, a pre-hypertensive patient (e.g., systolic BP of 120-139 mmHg/diastolic BP of 80-89 mmHg) may have blood pressure below the pre-hypertensive range after a renal neuromodulation procedure. Likewise, a hypertensive patient (e.g., systolic BP>140 mmHg/diastolic BP>90 mmHg) may have blood pressure below the hypertensive range after a renal neuromodulation procedure. Corresponding results may be obtained with angiotensin II levels, plasma aldosterone concentration, plasma renin activity, and/or aldosterone-to-renin ratio. For example, a reduction in an aldosterone-to-renin ratio can be, for example, by at least about 5%, 10% or a greater amount (e.g., about 50%, about 80%, about 90%) as determined by blood analysis and calculation before and after (e.g., 1, 3, 6, or 12 months after) a renal neuromodulation procedure.

Other measurable physiological parameters may also improve following renal neuromodulation. For example, a patient may have an improvement in (e.g., reduction, maintain a level of, slow a rate of progression of) atherosclerosis of extracranial and/or intracranial arteries, clinical measurements of aortic and large-artery, small-vessel disease or other alterations in small arteries providing physiological blood flow, neural activity (e.g., in the amygdala, ventromedial prefrontal cortex, dorsal anterior cingulate cortex, hippocampus and/or insular cortex or other regions involved in the limbic system), following a renal neuromodulation procedure as determined by qualitative or quantitative analysis (e.g., CT scan, PWV analysis, angiography, MM, PET scan, etc.) before and after (e.g., 1, 3, 6, or 12 months after; 2, 3, 4, 5 or 10 years after) a renal neuromodulation procedure.

As discussed previously, the development of a sleep disorder in certain individuals may be related to sympathetic overactivity either before (e.g., chronic or episodic), during (e.g., at the time of), or following an adverse life event or circumstance, and, correspondingly, the degree of sympathoexcitation in a patient may be related to one or more of the severity of the clinical presentation of a sleep disorder, the number of traumatic events experienced by the patient, whether the patient has had adversity during childhood, number and duration of adverse life events or circumstances (e.g., triggering psychological stress responses), personal or family history of sleep disorders, depression or mental illness, history of cardiovascular disease or stroke, among other psychological, physiological and genetic/epigenetic factors. The kidneys are positioned to be both a cause (via afferent nerve fibers) and a target (via efferent sympathetic nerves) of elevated central sympathetic drive. In some embodiments, renal neuromodulation can be used to reduce central sympathetic drive in a patient demonstrating one or more risk factors for a sleep disorder in a manner that treats the patient for a sleep disorder and/or to prevent an incidence of a sleep disorder in the patient in later life. In some embodiments, for example, MSNA can be reduced by at least about 10% in the patient within about three months after at least partially inhibiting sympathetic neural activity in nerves proximate a renal artery of the kidney. Similarly, in some instances whole body norepinephrine spillover to plasma can be reduced at least about 20%, about 30%, about 40%, about 45%, about 50% or a greater amount in the patient within about three months to about 12 months after at least partially inhibiting sympathetic neural activity in nerves proximate a renal artery of the kidney. Additionally, measured norepinephrine content (e.g., assessed via renal biopsy, assessed in real-time via intravascular blood collection techniques, assessed in real-time via urine, etc.) can be reduced (e.g., at least about 5%, 10%, or by at least 20%) in the patient within about three months after at least partially inhibiting sympathetic neural activity in nerves proximate a renal artery innervating the kidney.

In one prophetic example, a patient having one or more suspected risk factors for a sleep disorder and/or the development of a sleep disorder can be subjected to a baseline assessment indicating a first set of measurable parameters corresponding to the one or more risk factors. Such parameters can include, for example, levels of central sympathetic drive (e.g., MSNA, whole body norepinephrine spillover), measured norepinephrine content (e.g., assessed via tissue biopsy, plasma or urine), blood pressure, 24-hour blood pressure variability, heart rate variability, baroreceptor sensitivity, heart rate during stress/stimuli, skin conductance, glucocorticoid levels (e.g., in hair, urine, plasma, etc.), glucocorticoid resistance, CAR level, NPY level, CRH level, inflammatory biomarker levels (e.g., IL-6, IL-8, TNF-α, CRP, etc.), cholesterol levels, blood glucose levels, fasting blood insulin levels, measures of insulin sensitivity, body mass index, perceived cognitive functioning level (e.g., self-reporting, third-party reporting, etc.), one or more brain function test scores, and brain/body imaging for vascular remodeling (e.g., arteriole stiffness, arterial blood flow) and/or brain structural alterations (e.g., atrophy, neural activity, etc.). Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment; 2, 3, 4, 5 or 10 years following the treatment), the patient can be subjected to a follow-up assessment. The follow-up assessment can indicate a measurable improvement in one or more physiological parameters corresponding to the one or more suspected risk factors for the sleep disorder or the development of a sleep disorder.

The methods described herein address the sympathetic excess that is thought to be an underlying factor in sleep disorder progression or a central mechanism through which multiple sleep disorder risk factors are manifest in patients. Currently, there are no therapies prescribed to address the effects of sympathetic excess in patients suspected of having a sleep disorder or a risk of developing a sleep disorder. Certain proposed therapies, such as lifestyle alterations (e.g., exercise, diet, alcohol and other substance/drug avoidance, etc.), cognitive behavioral therapy, blood pressure maintenance (e.g., administration of anti-hypertensive therapies), anti-anxiety and/or anti-depression medications, sleep aides and medications, and reduction and/or maintenance of cholesterol have significant limitations including limited efficacy, undesirable side effects and may be subject to adverse or undesirable drug interactions when used in combination. Moreover, use of any drug regimens (e.g., sleep medications, anti-anxiety, antidepressant, anti-hypertensive, cholesterol-lowering, anti-inflammatory, etc.) can have many challenges, including drug contraindications and drug adherence (particularly prior to onset of symptoms). For example, many of these drug regimens may require the patient to remain compliant with the treatment regimen starting in early life (e.g., prior to on-set of a sleep disorder diagnosis) and continue compliance over time. In contrast, neuromodulation can be a one-time or otherwise limited treatment that would be expected to have durable benefits to treat sleep disorders, reduce severity of a sleep disorder and/or inhibit the long-term potential of developing a sleep disorder and thereby achieve a favorable patient outcome.

In some embodiments, patients demonstrating one or more risk factors associated with a sleep disorder or the development of a sleep disorder and/or have one or more physiological indicators of sympathetic excess (e.g., combined with additional risk factors) can be treated with renal neuromodulation alone. However, in other embodiments, combinations of therapies can be tailored based on specific conditions and sleep disorder risk factors in a particular patient. For example, certain patients can be treated with combinations of therapies such as one or more conventional therapies for treating an anxiety disorder or depression, for treating sleep disorders, and/or reducing blood pressure (e.g., anti-hypertensive drug(s)) and treated with one or more neuromodulation treatments. In another example, renal neuromodulation can be combined with cholesterol lowering agents (e.g., statins), anti-inflammatory therapy (e.g., drug(s)), as well as weight loss and lifestyle change recommendations/programs. In certain embodiments, a patient being treated with one or more pharmaceutical drugs for anxiety and/or conditions associated with a sleep disorder can be treated with renal neuromodulation to reduce at least one of a number of or a measured dosage of the pharmaceutical drugs administered to the patient.

Treatment of sleep disorder risk factors or symptoms and conditions associated with a sleep disorder may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

IV. SELECTED EXAMPLES OF NEUROMODULATION MODALITIES

As noted previously, complete or partial neuromodulation of a target renal sympathetic nerve in accordance with embodiments of the present technology can be electrically-induced, thermally-induced, chemically-induced, or induced in another suitable manner or combination of manners at one or more suitable locations along one or more renal blood vessels during a treatment procedure. For example, neuromodulation may be achieved using various modalities, including for example monopolar or bipolar RF energy, pulsed RF energy, microwave energy, laser light or optical energy, magnetic energy, ultrasound energy (e.g., intravascularly delivered ultrasound, extracorporeal ultrasound, high-intensity focused ultrasound (HIFU)), direct heat energy, radiation (e.g., infrared, visible, gamma), or cryotherapeutic energy, chemicals (e.g., drugs or other agents), or combinations thereof. Where a system uses a monopolar configuration, a return electrode or ground patch fixed externally on the subject can be used. In certain embodiments, neuromodulation may utilize one or more devices including, for example, catheter devices such as the Symplicity Spyral™ catheter (Medtronic, Inc.). Other suitable thermal devices are described in U.S. Pat. Nos. 7,653,438, 8,347,891, and U.S. patent application Ser. No. 13/279,205, filed Oct. 21, 2011. Other suitable devices and technologies are described in U.S. patent application Ser. No. 13/279,330, filed Oct. 23, 2011, International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. Other examples of suitable direct heat devices are described in International Patent Application No. PCT/US2014/023738 filed Mar. 11, 2014, and U.S. patent application Ser. No. 14,203,933, filed Mar. 11, 2014. All of the foregoing patent references are incorporated herein by reference in their entireties.

In those embodiments of the methods disclosed herein that utilize partial ablation, the level of energy delivered to the target artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities. In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial neuromodulation of a renal sympathetic nerve can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic nerve can slow or potentially block conduction of neural signals to produce a prolonged or permanent reduction in sympathetic activity. A variety of suitable types of energy, such as those mentioned above, can be used to stimulate and/or heat tissue at a treatment location. In some embodiments, neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective neuromodulation of a target sympathetic nerve. For example, cryotherapeutic treatment can include cooling tissue at a treatment location in a manner that modulates neural function. For example, sufficiently cooling at least a portion of a target sympathetic nerve can slow or potentially block conduction of neural signals to produce a prolonged or permanent reduction in sympathetic activity associated with the target sympathetic nerve. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion.

Neuromodulation using a cryotherapeutic treatment in accordance with embodiments of the present technology can include cooling a structure proximate an inner surface of a vessel or chamber wall such that tissue is effectively cooled to a depth where sympathetic nerves reside. For example, a cooling assembly of a cryotherapeutic device can be cooled to the extent that it causes therapeutically-effective, cryogenic neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause organs and tissues to rise and fall and thereby move the arteries and other structures associated with these organs and tissues. In addition, blood flow is pulsatile and can cause structures associated with the kidneys to pulse. Cryogenic adhesion also can facilitate intravascular or intraluminal positioning, particularly in relatively-small structures (e.g., renal branch arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In certain embodiments, monitoring, assessing and/or determining neuromodulation efficacy can be accomplished by detecting changes in the level of one or more surrogate biomarkers (e.g., a biomarker that directly or indirectly correlates with sympathetic nerve activity in the patient, a biomarker that directly or indirectly correlates with hypertension, arterial stiffness and/or an inflammatory response in the patient) in serum, plasma and/or urine in response to neuromodulation. Systems and method for monitoring the efficacy of neuromodulation by measuring the levels of one or more biomarkers associated with neuromodulation including, for example, proteins or non-protein molecules that exhibit an increase or decrease in level or activity in response to neuromodulation are described in, e.g., International Patent Application No. PCT/US2013/030041, filed Mar. 8, 2013, and International Patent Application No. PCT/US2015/047568, filed Aug. 28, 2015, the disclosures of which are incorporated herein by reference in their entireties. In other embodiments, measured levels of protein or non-protein molecules (e.g., associated with norepinephrine spillover, associated with inflammatory responses, etc.) that exhibit an increase or decrease in level or activity in response to targeted neuromodulation can be assessed pre- and post-neuromodulation in tissue biopsies.

V. SELECTED EMBODIMENTS OF RENAL NEUROMODULATION SYSTEMS AND DEVICES

Figure 3:
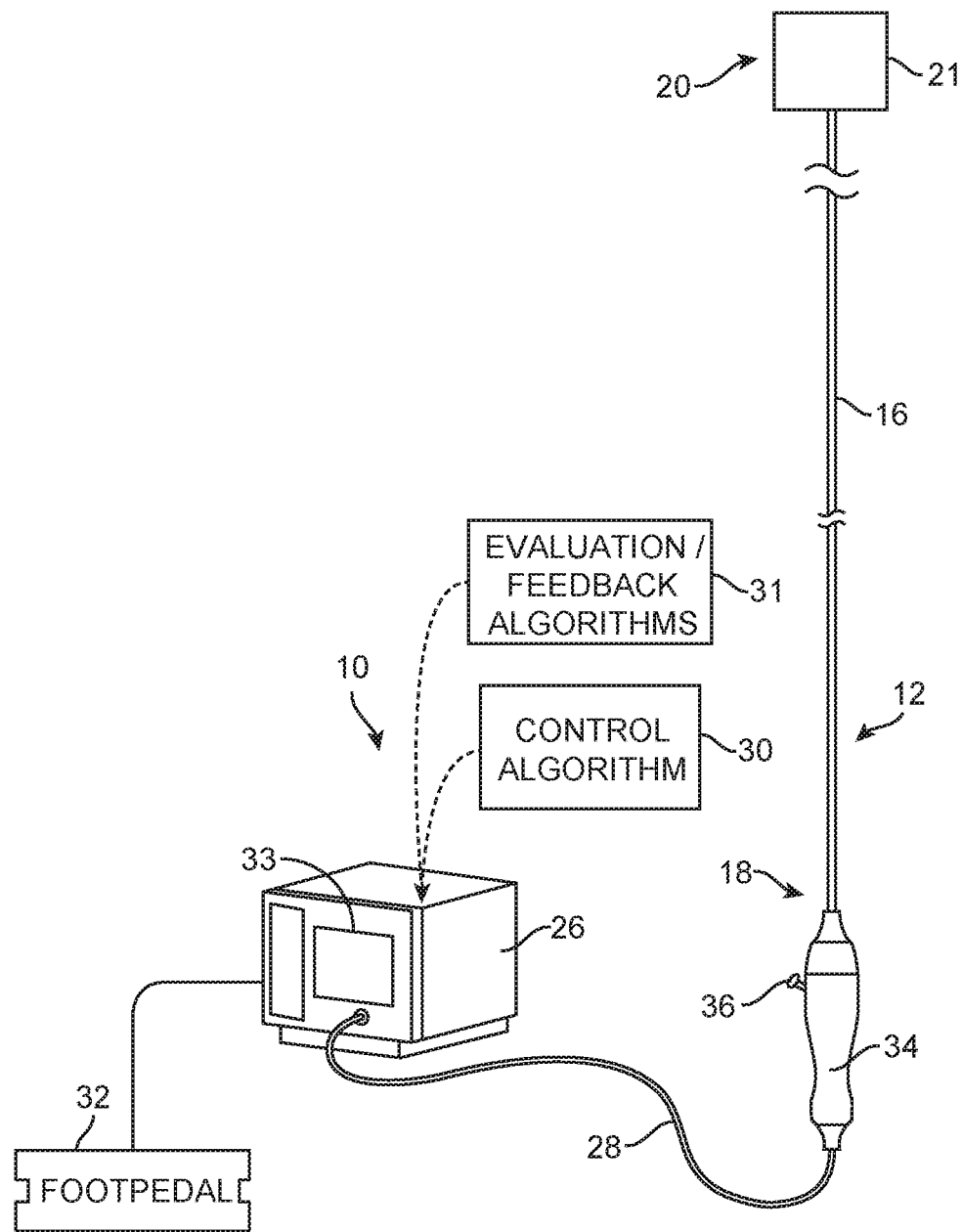
FIG. 3 illustrates an intravascular neuromodulation system configured in accordance with an embodiment of the present technology.

FIG. 3 illustrates a renal neuromodulation system 10 configured in accordance with an embodiment of the present technology. The system 10, for example, may be used to perform therapeutically-effective renal neuromodulation on a patient (a) to reduce the risk of occurrence of a sleep disorder, (b) to reduce a calculated sleep disorder risk score corresponding to a sleep disorder status, (c) to reduce a severity of neurological symptoms relating to a sleep disorder, and/or (d) to treat and/or prevent development of one or more comorbid conditions/diseases associated with a sleep disorder (e.g., hypertension, cardiovascular disease, stroke risk, metabolic disorders, insulin resistance, diabetes, systemic inflammation, dementia, chronic kidney disease, etc.). In one embodiment, the patient may be diagnosed with increased overall sympathetic activity, and, in particular, conditions associated with central sympathetic overstimulation and increased risk of developing a sleep disorder, such as hypertension, blood pressure variability, systemic inflammation, anxiety, chronic stress, depression, cardiovascular disease, history of stroke or TIA, obesity, metabolic syndrome, insulin resistance and diabetes, among others.

The system 10 includes an intravascular treatment device 12 operably coupled to an energy source or console 26 (e.g., a RF energy generator, a cryotherapy console). In the embodiment shown in FIG. 3, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can be configured to ablate nerve tissue and/or for monitoring one or more physiological parameters within the vasculature. Accordingly, a neuromodulation assembly 21 suitable for ablation may include one or more electrodes, transducers, energy-delivery elements or cryotherapeutic cooling assemblies. Neuromodulation assemblies 21 suitable for monitoring may also include a nerve monitoring device and/or blood collection/analysis device. In some embodiments, the neuromodulation assembly 21 can be configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In further embodiments, the neuromodulation assembly 21 can include one or more electrodes configured to deliver ablation energy and/or stimulation energy. In some arrangements, the neuromodulation assembly 21 can include one or more sensor(s) for detecting impedance or nerve monitoring signals. In any of the foregoing embodiments, the neuromodulation assembly 21 may comprise an irrigated electrode.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The console 26 can be configured to deliver the treatment energy via an automated control algorithm 30 and/or under the control of the clinician. In addition, the console 26 may include one or more evaluation and/or feedback algorithms 31 to provide feedback to the clinician before, during, and/or after therapy.

The console 26 can further include a device or monitor that may include processing circuitry, such as a microprocessor, and a display 33. The processing circuitry may be configured to execute stored instructions relating to the control algorithm 30. The console 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or balloon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VI. SELECTED EXAMPLES OF TREATMENT PROCEDURES FOR RENAL NEUROMODULATION

A. Achieving Intravascular Access to the Renal Artery

Figures 4A, 4B:
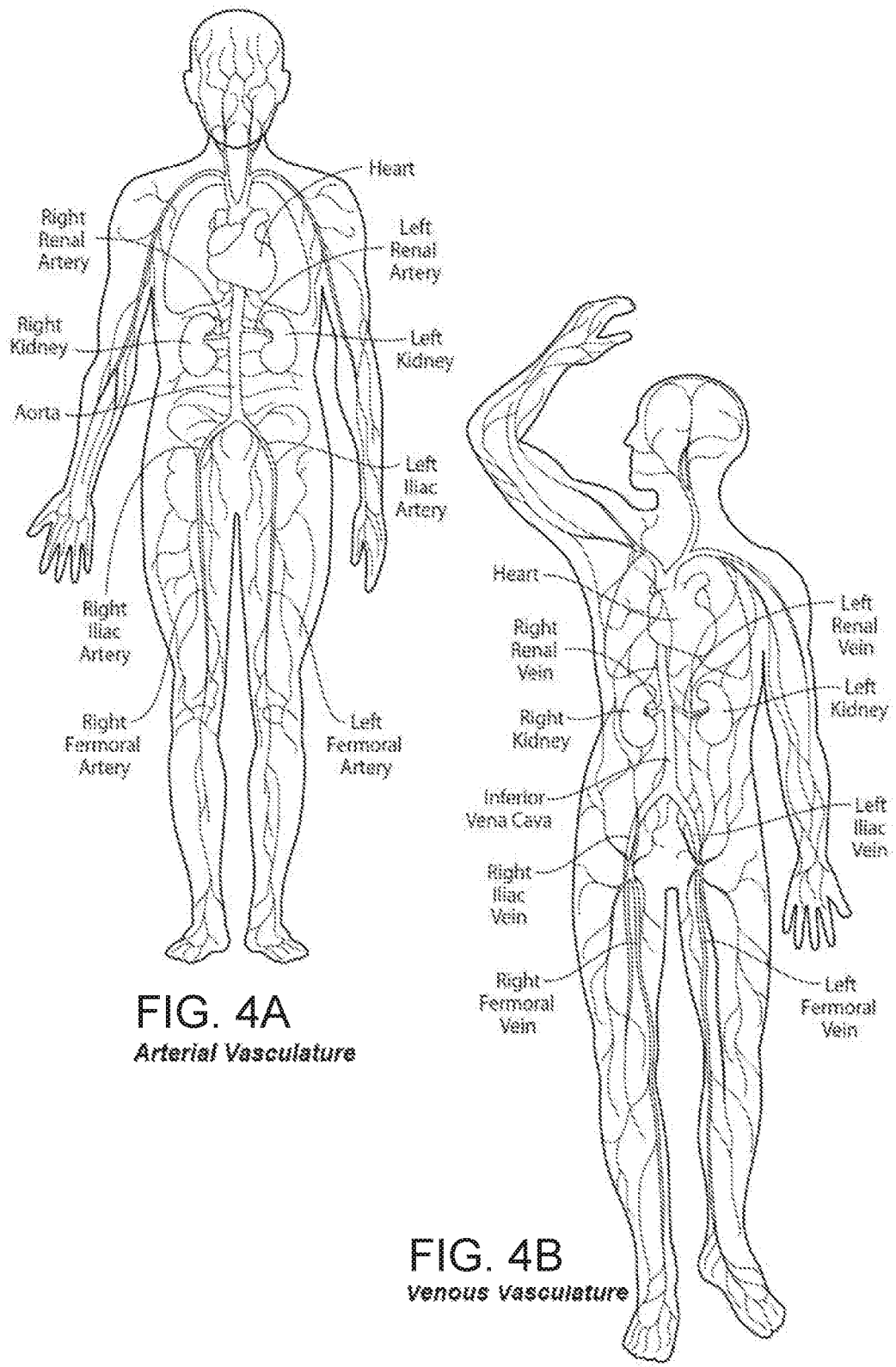
FIGS. 4A and 4B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

B. Properties and Characteristics of the Renal Vasculature

Properties and characteristics of the renal vasculature impose challenges to both access and treatment methods, and to system/device designs. Since neuromodulation of a left and/or right renal plexus RP may be achieved in accordance with embodiments of the present technology through intravascular access, various aspects of the design of apparatus, systems, and methods for achieving such renal neuromodulation are disclosed herein. Aspects of the technology disclosed herein address additional challenges associated with variation of physiological conditions and architecture across the patient population and/or within a specific patient across time, as well as in response to disease states, such as hypertension, atherosclerosis, vascular disease, chronic inflammatory condition, insulin resistance, diabetes, metabolic syndrome, etc. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery. For example, spiral or helical CT technology can be used to produce 3D images of the vascular features for individual patients, and intravascular path choice as well as device size/diameter, length, flexibility, etc. can be selected based upon the patient's specific vascular features.

In addition to complicating renal arterial access, specifics of the renal anatomy also complicate establishment of stable contact between neuromodulatory apparatus and a luminal surface or wall of a renal blood vessel. When the neuromodulatory apparatus includes an energy delivery element, such as an electrode, transducer, or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse). To address these challenges, the treatment device or applicator may be designed with relative sizing and flexibility considerations. For example, the renal artery may have an internal diameter in a range of about 2-10 mm and the treatment device can be delivered using a 3, 4, 5, 6, 7 French, or in some cases, an 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a renal artery and facilitating stable contact between neuromodulatory apparatus and a luminal surface of the artery, nerves in and around the adventitia of the artery can be modulated via the neuromodulatory apparatus. In further embodiments, energy can be applied via the neuromodulatory apparatus to renal perivascular adipose tissue positioned adjacent to the targeted renal artery. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant (e.g., 1-3 mm) from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery. Accordingly, sensory feedback, such as impedance and temperature, can be used to assess whether a desired energy distribution is administered at the treatment site and can, in some instances, be used to change an energy delivery algorithm in real-time to adjust for varying fluctuations in the properties and conditions affecting heat transfer dynamics at the treatment site.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of creating a circumferential lesion or ablation may outweigh the potential of renal artery stenosis or the risk may be mitigated with certain embodiments or in certain patients and creating a circumferential lesion or ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

C. Neuromodulation of Renal Sympathetic Nerve at Treatment Site

Figure 5:
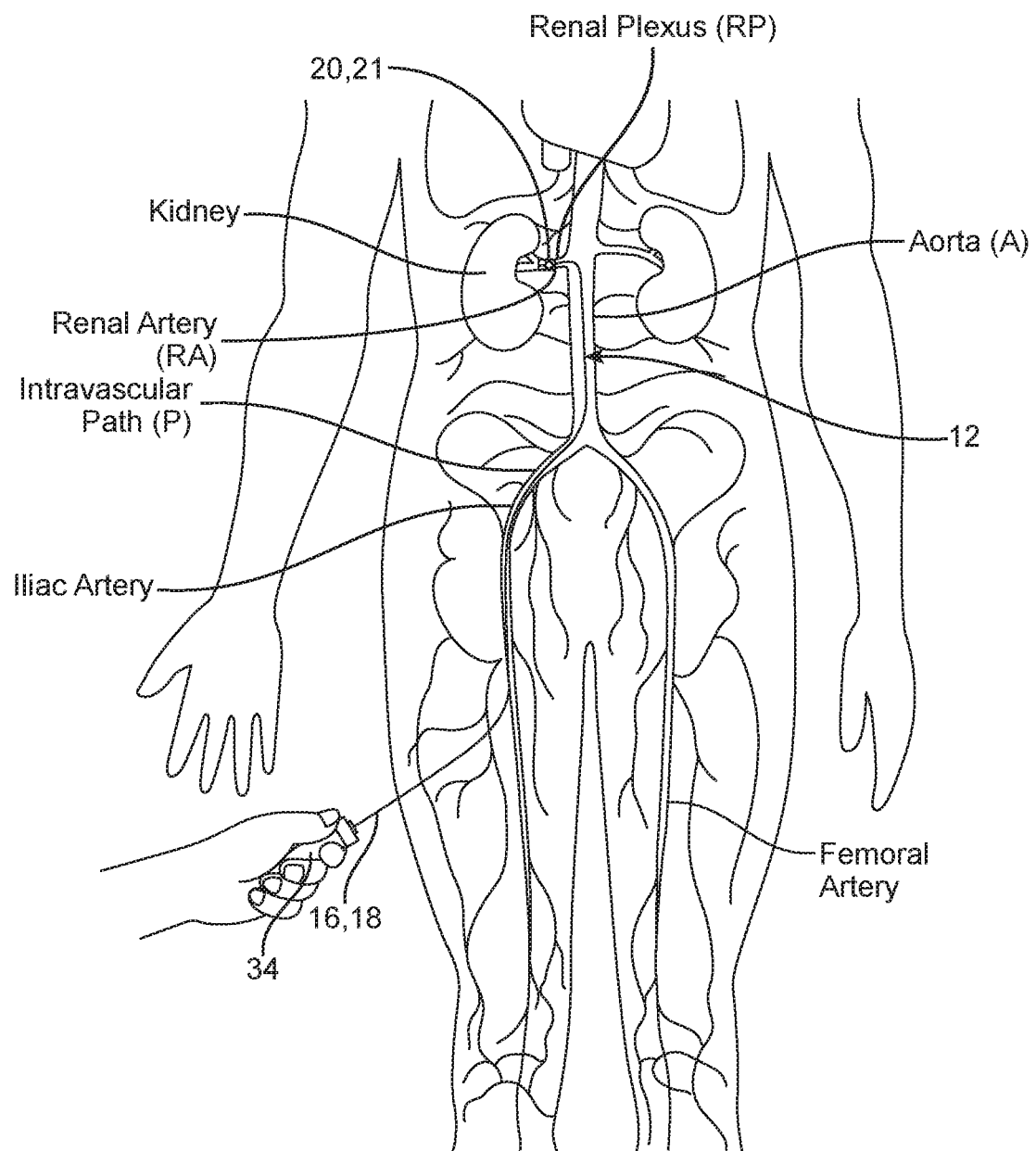
FIG. 5 illustrates modulating renal nerves with a neuromodulation system configured in accordance with an embodiment of the present technology.

FIG. 5 illustrates modulating renal nerves with an embodiment of the system 10 (FIG. 3). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., CT, fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. For example, the application of energy can be applied to renal neural tissue or to renal perivascular adipose tissue that within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP. In targeting the renal perivascular adipose tissue, the effects of the energy delivery may achieve thermal ablation or non-ablative thermal alteration or damage to such cells. While delivery of energy to alter or damage renal perivascular adipose tissue has been discussed, it is also anticipated that other types of cell-altering or damaging therapies (e.g., delivery of chemical agents) can be used.

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured form a partially-circumferential lesion or a fully-circumferential lesion at a single longitudinal segment or zone of the vessel. During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

Furthermore, a treatment procedure can include treatment at any suitable number of treatment locations, e.g., a single treatment location, two treatment locations, or more than two treatment locations. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16 fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

Figure 6:
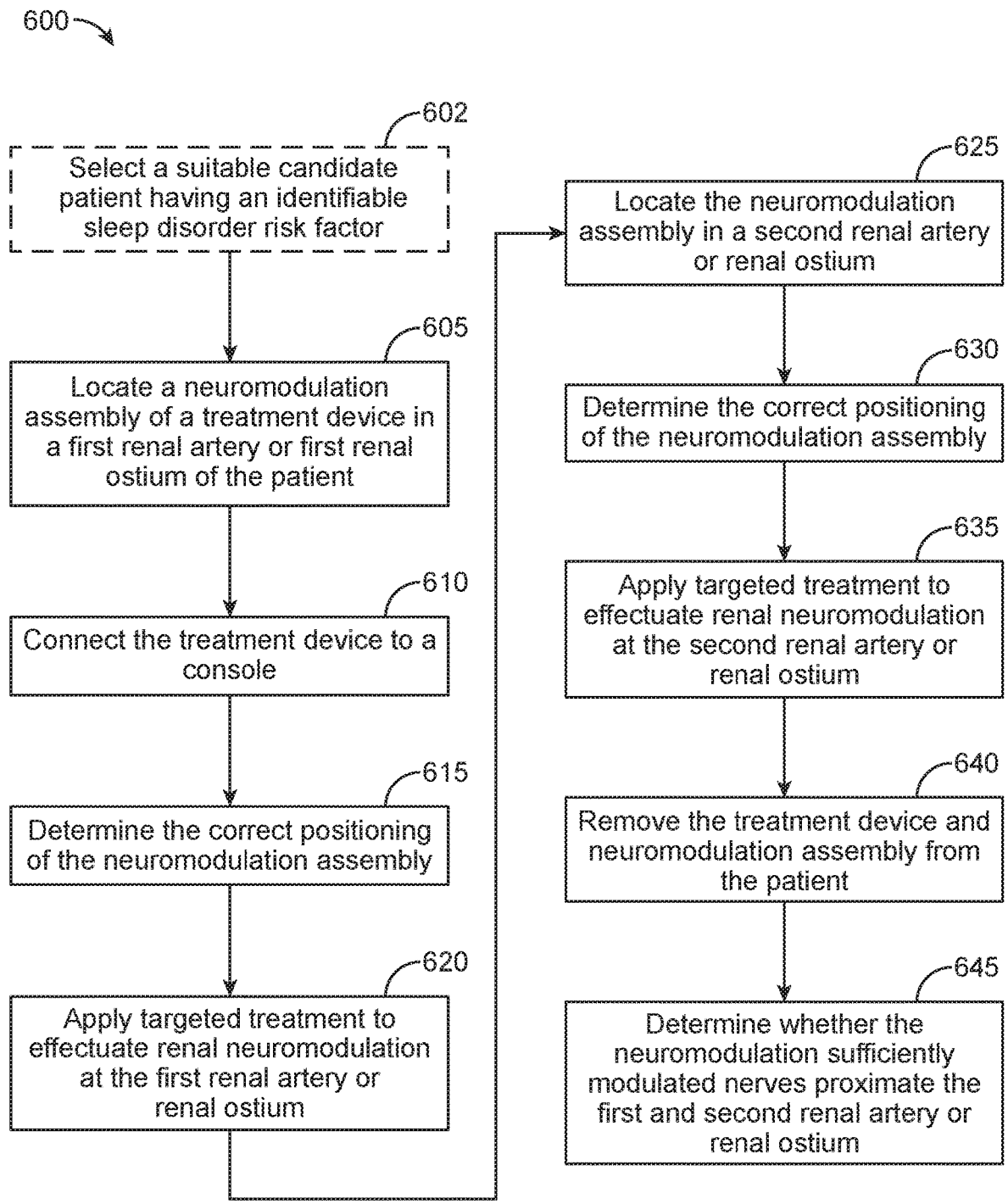
FIG. 6 is a block diagram illustrating a method of modulating renal nerves in accordance with an embodiment of the present technology.

FIG. 6 is a block diagram illustrating a method 600 of modulating renal nerves using the system 10 described above with reference to FIGS. 3 and 5. With reference to FIGS. 3, 5 and 6 together, the method 600 can optionally include selecting a suitable candidate patient having an identifiable sleep disorder risk factor for performing renal neuromodulation (block 602). For example, a suitable patient can include a patient having a sleep disorder risk score corresponding to a sleep disorder status in the patient that is above a threshold level, a patient having one or more measurable risk factors for developing a sleep disorder, a patient having one or more identifiable sleep dysfunction-associated symptoms, a patient diagnosed with a sleep disorder, an at-risk patient having a history of a sleep or other mental disorder (e.g., depression, anxiety disorder) and/or a genetic predisposition for developing a sleep disorder, and/or a patient with a history of cardiovascular disease or stroke and having one or more identifiable risk factors for developing a sleep disorder.

Modulating SNS nerves innervating the kidneys is expected to lower renal nerve activity and/or central SNS nerve activity, thereby inhibiting, preventing, slowing, disrupting or reversing physiological pathways associated with sleep disorders and/or lowering a risk associated with developing a sleep disorder in the patient either before or after on-set of one or more sleep dysfunction-associated symptoms. In particular, targeting the renal nerve for neuromodulation is anticipated to reduce renal norepinephrine spillover, whole body norepinephrine spillover, and reduce central sympathetic drive (e.g., reduce a level of efferent SNS nerve firing) in the patient, thereby inhibiting, preventing, slowing, disrupting or reversing a sleep disorder and/or symptoms associated with a sleep disorder and/or conditions proposed to increase a patient's risk of developing a sleep disorder. Further, damaging renal perivascular adipose tissue is anticipated to reduce renal norepinephrine spillover (e.g., released) from these cells. Without being bound by theory, renal neuromodulation is anticipated to address the hyperactivity of the SNS and/or the elevated SNS tone present in patients with a sleep disorder and/or patients having one or more risk factors for developing a sleep disorder. In other instances, and without being bound by theory, an overactive or hyperactive SNS is believed to be an underlying contributing cause of sleep disorders and renal neuromodulation is anticipated to prevent or prohibit the development of a hyperactive or overactive SNS in a patient prior to or subsequent to experiencing an adverse life event or circumstance that precipitates, for example, excessive or chronic psychological stress. In such instances, sleep disorders and/or sleep dysfunction-associated symptoms can be attenuated and/or avoided despite experiencing the stress-inducing, adverse life event or circumstance.

The method 600 can include intravascularly locating the neuromodulation assembly 21 in a delivery state (e.g., low-profile configuration) to a first target site in or near a first renal blood vessel (e.g., first renal artery) or first renal ostium (block 605). The treatment device 12 and/or portions thereof (e.g., the neuromodulation assembly 21) can be inserted into a guide catheter or sheath to facilitate intravascular delivery of the neuromodulation assembly 21. In certain embodiments, for example, the treatment device 12 can be configured to fit within an 8 Fr guide catheter or smaller (e.g., 7 Fr, 6 Fr, etc.) to access small peripheral vessels. A guide wire (not shown) can be used to manipulate and enhance control of the shaft 16 and the neuromodulation assembly 21 (e.g., in an OTW or a RX configuration). In some embodiments, radiopaque markers and/or markings on the treatment device 12 and/or the guide wire can facilitate placement of the neuromodulation assembly 21 at the first target site (e.g., a first renal artery or first renal ostium of the patient). In some embodiments, a contrast material can be delivered distally beyond the neuromodulation assembly 21, and fluoroscopy and/or other suitable imaging techniques can be used to aid in placement of the neuromodulation assembly 21 at the first target site.

The method 600 can further include connecting the treatment device 12 to the console 26 (block 610), and determining whether the neuromodulation assembly 21 is in the correct position at the target site and/or whether the neuromodulation assembly (e.g., electrodes or cryotherapy balloon) is functioning properly (block 615). Once the neuromodulation assembly 21 is properly located at the first target site and no malfunctions are detected, the console 26 can be manipulated to initiate application of an energy field to the target site to cause electrically-induced and/or thermally-induced partial or full denervation of the kidney (e.g., using electrodes or cryotherapeutic devices). Accordingly, heating and/or cooling of the neuromodulation assembly 21 causes modulation of renal nerves at the first target site to cause partial or full denervation of the kidney associated with the first target site (block 620).

In one example, the treatment device 12 can be an RF energy emitting device and RF energy can be delivered through energy delivery elements or electrodes to one or more locations along the inner wall of the first renal blood vessel or first renal ostium for predetermined periods of time (e.g., 120 seconds). In some embodiments, multiple treatments (e.g., 4-6) may be administered in both the left and right renal blood vessels (e.g., renal arteries) to achieve a desired coverage and/or desired inhibition of sympathetic neural activity in the body.

In some embodiments, a treatment procedure can include applying a suitable treatment modality at a treatment location in a testing step (not shown) followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

A technical objective of a treatment may be, for example, to heat tissue to a desired depth (e.g., at least about 3 mm) to a temperature that would lesion a nerve (e.g., about 65° C.). A clinical objective of the procedure typically is to treat (e.g., lesion) a sufficient number of renal nerves (either efferent or afferent nerves) to cause a reduction in sympathetic tone or drive to the kidneys. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.

In a specific example of using RF energy for renal nerve modulation, a clinician can commence treatment which causes the control algorithm 30 (FIG. 3) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In another specific example, the treatment device 12 can be a cryogenic device and cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the neuromodulation assembly 21). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 21 can then be located at a second target site in or near a second renal blood vessel (e.g., second renal artery) or second renal ostium (block 625), and correct positioning of the assembly 21 can be determined (block 630). In selected embodiments, a contrast material can be delivered distally beyond the neuromodulation assembly 21 and fluoroscopy and/or other suitable imaging techniques can be used to locate the second renal artery. The method 600 continues by applying targeted heat or cold to effectuate renal neuromodulation at the second target site to cause partial or full denervation of the kidney associated with the second target site (block 635).

After providing the therapeutically-effective neuromodulation energy (e.g., cryogenic cooling, RF energy, ultrasound energy, etc.), the method 600 may also include removing the treatment device 12 (e.g., catheter) and the neuromodulation assembly 21 from the patient (block 640). In some embodiments, the neuromodulation assembly 21 can be an implantable device (not shown) and a treatment procedure can include implanting the neuromodulation assembly 21 at a suitable treatment location within the patient. Other treatment procedures for modulation of target sympathetic nerves in accordance with embodiments of the present technology are also possible.

The method 600 may also include determining whether the neuromodulation sufficiently modulated nerves or other neural structures proximate the first and second target sites (block 645). For example, the process of determining whether the neuromodulation therapeutically treated the nerves can include determining whether nerves were sufficiently modulated or otherwise disrupted to reduce, suppress, inhibit, block or otherwise affect the afferent and/or efferent renal signals (e.g., by evaluation of suitable biomarkers, stimulation and recording of nerve signals, etc.). Examples of suitable biomarkers and their detection are described in International Patent Application No. PCT/US2013/030041, filed Mar. 8, 2013, and International Patent Application No. PCT/US2015/047568, filed Aug. 28, 2015, the disclosures of which are incorporated herein by reference in their entireties. Other suitable devices and technologies, such as endovascular intraoperative renal nerve monitoring devices are described in International Patent Application No. PCT/US12/63759, filed Jan. 29, 2013, and incorporated herein by reference in its entirety.

In a further embodiment, patient assessment could include determining whether the neuromodulation therapeutically treated the patient for one or more symptoms associated with a sleep disorder, e.g., core sleep disorder symptoms (e.g., difficulty in falling asleep, waking in the middle of the night or early morning, waking to use the bathroom, snoring and/or coughing, unable to breath comfortably, too cold or hot, experiencing bad dreams, experiencing pain, needing medication to fall asleep, feeling sad, feeling nervous or anxious, experiencing restless legs before or during sleep, difficulty staying awake during the day, experiencing difficulty in maintaining enthusiasm in activities or hobbies, etc.), feelings of anxiety or depression, systemic inflammation, and undesirable elevations in heart rate, blood pressure, and skin conductance, among others. Assessment of certain suitable biomarkers and/or nerve signals may be made immediately or shortly after neuromodulation (e.g., about 15 minutes, about 24 hours, or about 7 days post-neuromodulation). In further embodiments, patient assessment could be performed at time intervals (e.g., about 1 month, 3 months, 6 months, 12 months) following neuromodulation treatment. For example, the patient can be assessed for measurements of blood pressure, blood pressure variability, nocturnal blood pressure "dipping," MSBP level, skin conductance, resting heart rate, measures of sympathetic activity (e.g., MSNA, renal and/or total body norepinephrine spillover, plasma norepinephrine levels, and heart rate variability), peripheral inflammatory markers (e.g., IL-6, CRP, etc.), NPY level, measures of HPA axis function (e.g., glucocorticoid levels (e.g., in hair, urine, plasma, etc.), glucocorticoid resistance, CAR level, CRH level, etc.), sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio), and/or a post-neuromodulation sleep disorder risk score (e.g., via a sleep quality screening tool for determining a severity of a sleep disorder).

In other embodiments, various steps in the method 600 can be modified, omitted, and/or additional steps may be added. In further embodiments, the method 600 can have a delay between applying therapeutically-effective neuromodulation energy to a first target site at or near a first renal artery or first renal ostium and applying therapeutically-effective neuromodulation energy to a second target site at or near a second renal artery or second renal ostium. For example, neuromodulation of the first renal artery can take place at a first treatment session, and neuromodulation of the second renal artery can take place at a second treatment session at a later time.

Figure 7:
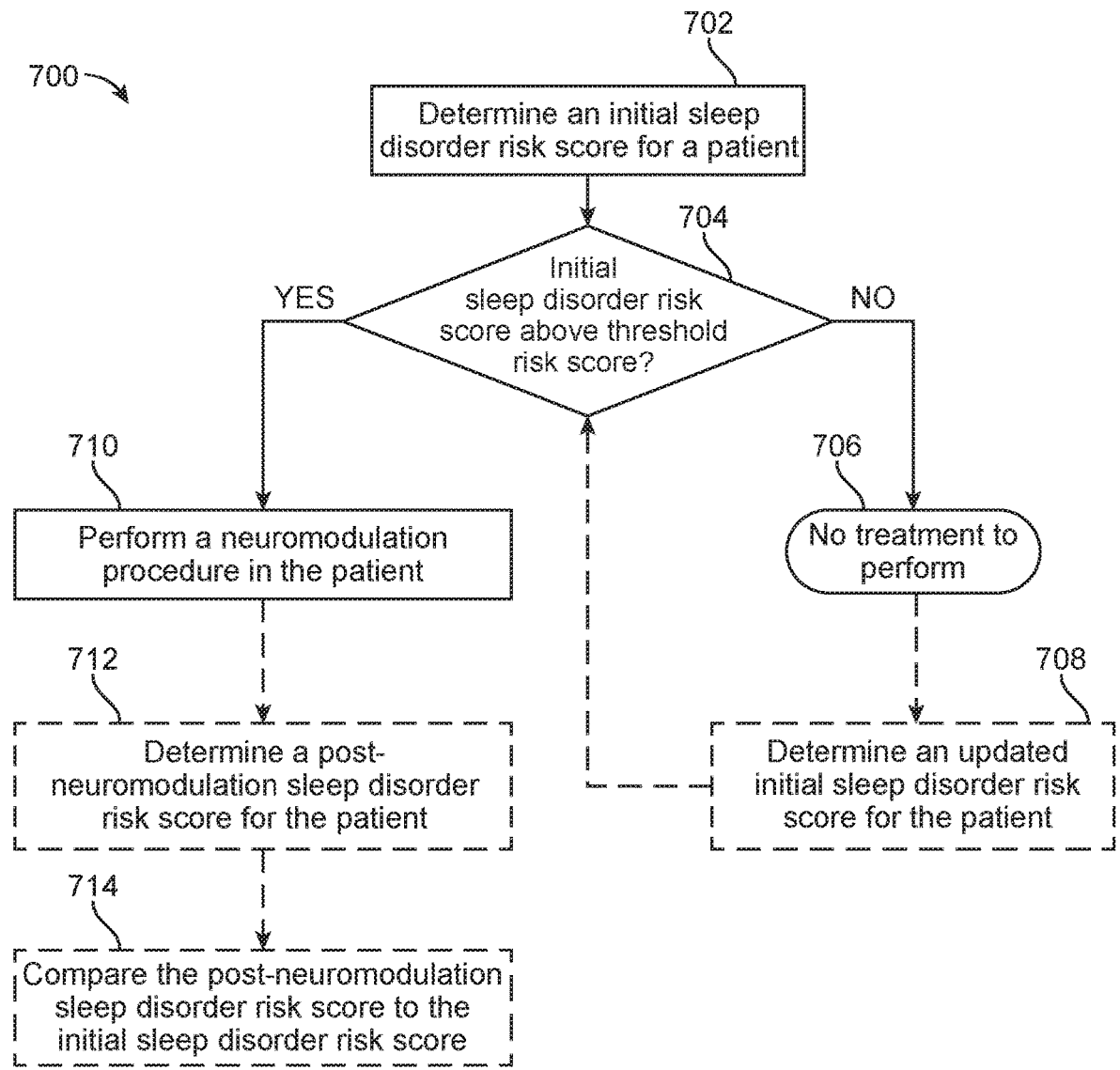
FIG. 7 is a block diagram illustrating a method for improving a sleep disorder risk score for a patient in accordance with an embodiment of the present technology.

FIG. 7 is a block diagram illustrating a method 900 for improving a sleep disorder risk score for a patient in accordance with aspects of the present technology. In a first step, the method 700 can include determining an initial sleep disorder risk score for a patient (block 702). For example, one or more suitable sleep disorder risk score calculating techniques or tools can be used to establish a sleep disorder risk score corresponding to a sleep disorder status in the patient as described above. At decision block 704, the initial sleep disorder risk score can be evaluated against a threshold risk score or value. If the initial sleep disorder risk score is not above the threshold risk score, there is no need to reduce the sleep disorder risk score for the patient at the current time and no treatment is selected to perform (block 706). In such a patient, a clinician may recommend monitoring the patient's sleep disorder risk score over time. For example, a clinician can optionally determine an updated initial sleep disorder risk score for the patient after a determined time lapse (e.g., 1 month, 2 months, 3 months, 6 months, 12 months, etc.) (block 708). Following each sleep disorder risk score evaluation (block 708), the patient's sleep disorder risk score is evaluated against the threshold risk score or value (decision block 704).

If the patient's sleep disorder risk score from method step 702, or from the optional method step 708, is higher than the threshold risk score, the method 700 can include performing a neuromodulation procedure in the patient (block 710). In one example, the patient can be a suitable candidate patient as identified in method step 602 of method 600 described above, and the neuromodulation procedure can be performed as described in continuing steps of method 600. In other embodiments, a clinician can perform an alternative neuromodulation procedure at method step 710. For example, neuromodulation of other target (e.g., non-renal) sympathetic nerves or neuromodulation in a single renal blood vessel (e.g., renal artery) may be performed on the patient.

The method 700 is expected to improve the patient's sleep disorder risk score or reduce a probability of the patient developing a sleep disorder. Optionally, the clinician can further determine a post-neuromodulation sleep disorder risk score for the patient (block 712). For example, the patient can be evaluated using the sleep disorder risk score tool to assess the patient's post-neuromodulation sleep disorder status or, alternatively, risk of developing a sleep disorder. If the post-neuromodulation sleep disorder risk score is determined for the patient in step 712, the method includes comparing the post-neuromodulation sleep disorder risk score to the initial sleep disorder risk score (block 714). In determining if the method 700 is successful, the post-neuromodulation sleep disorder risk score is lower than the patient's initial sleep disorder risk score as determined in step 702 (or updated initial sleep disorder risk score as determined in step 708). In some examples, the post-neuromodulation sleep disorder risk score is lower than the initial sleep disorder risk score by about 5%, about 10%, about 20% or about 30%. In other embodiments, the post-neuromodulation sleep disorder risk score is lower than the initial sleep disorder risk score by more than 30%. In certain embodiments, the post-neuromodulation sleep disorder risk score can be lower than the threshold risk score.

VII. EXPERIMENTAL EXAMPLES

Example 1

This section describes an example of the outcome of renal neuromodulation on human patients. A total of 45 patients (mean age of 58±9 years) diagnosed with essential hypertension were treated with percutaneous, catheter based renal nerve ablation. Treatment included RF energy delivery to the renal artery using a single-electrode Symplicity Flex™ catheter commercially available from Medtronic, Inc., of 710 Medtronic Parkway, Minneapolis, Minn. 55432-5604. In this human trial, a radiotracer dilution method was used to assess overflow of norepinephrine from the kidneys into circulation before and 15-30 days after the procedure in 10 patients. Bilateral renal-nerve ablation resulted in a marked reduction in mean norepinephrine spillover from both kidneys: 47% (95% confidence interval) one month after treatment.

In a similar human trial where bilateral renal nerve ablation was performed in 70 patients, whole-body norepinephrine levels (i.e., a measure of "total" sympathetic activity), fell by nearly 50% after renal nerve ablation and measurement of muscle sympathetic nerve activity showed a drop of 66% over 6 months, further supporting the conclusion that total sympathetic dive was reduced by the renal denervation procedure in this patient group.

Example 2

Example 2 describes the outcome of catheter-based renal neuromodulation on human patients diagnosed with hypertension. Patients selected having a baseline systolic blood pressure of 160 mm Hg or more (≥150 mm Hg for patients with type 2 diabetes) and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, p<0.0001), whereas they did not differ from baseline in the control group (change of 1/0 mm Hg, baseline of 178/97 mm Hg, p=0.77 systolic and p=0.83 diastolic). Between-group differences in blood pressure at 6 months were 33/11 mm Hg (p<0.0001). At 6 months, 41 (84%) of 49 patients who underwent renal neuromodulation had a reduction in systolic blood pressure of 10 mm Hg or more, compared with 18 (35%) of 51 control patients (p<0.0001).

Example 3

Example 3 describes the outcome of catheter-based renal neuromodulation on animal subjects in an additional experiment. In this example (and referring to FIGS. 8A and 8B), studies using the pig model were performed using a multi-electrode Symplicity Spyral™ catheter or a single-electrode Symplicity Flex™ catheter along with a Symplicity G3™ generator. The catheters and generator were commercially available from Medtronic, Inc. The catheters were used in these cohorts of animals (n=66) to create multiple RF ablations in the renal vasculature. Cortical axon density in the renal cortex (FIG. 8A) and renal cortical norepinephrine (NE) concentration (FIG. 8B) were used as markers to measure procedural efficacy.

As shown in FIG. 8A, cortical axon area (per $mm^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

Figure 8B:
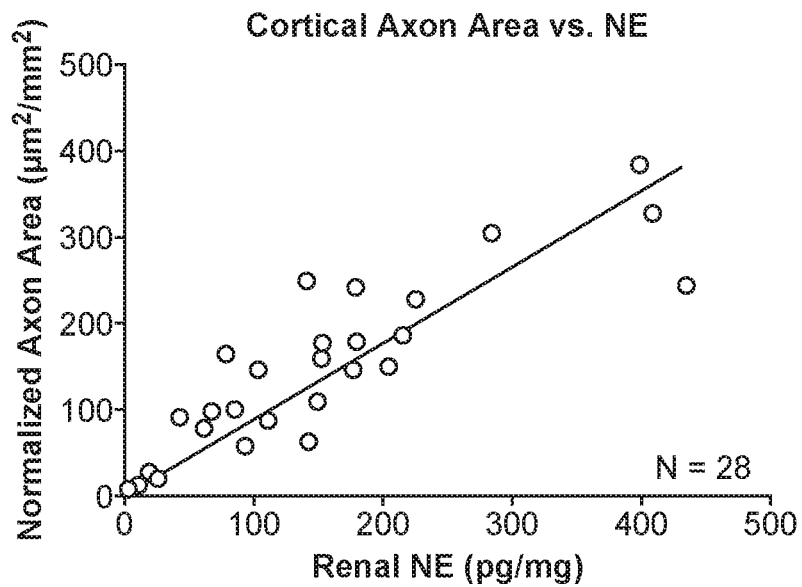
FIG. 8B is a series of graphs illustrating the response correlation between normalized cortical axon area vs. norepinephrine concentration and norepinephrine concentration vs. extent of nerve ablation along the artery of the animal subjects of FIG. 8A.
Figure 8B:
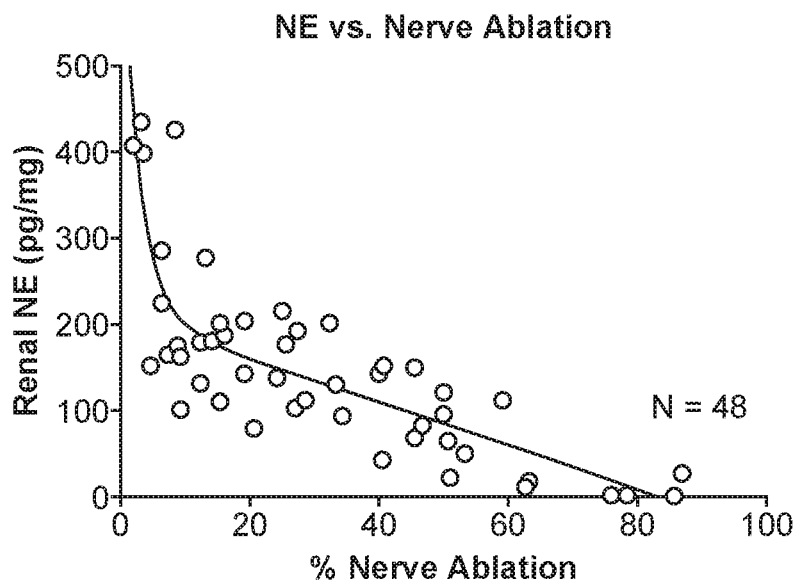

FIG. 8B includes (a) a graph of normalized cortical axon area vs. renal NE concentration, and (b) a graph of renal NE concentration vs. extent (%) of nerve ablation. Referring to the table of FIG. 10A and the two graphs of FIG. 8B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level compared with the pigs in the control group. This is further shown by the first graph of FIG. 8B, which demonstrates that a decrease in cortical axon area correlates with a decrease in NE levels. Referring to the second graph of FIG. 8B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability, and further suggest that neuromodulation of SNS fibers innervating a target tissue and/or organ (such as the kidney) result in a significant decrease in local NE concentration.

Example 4

Example 4 describes an example of the outcome of renal neuromodulation on human patients. Markers of cardiovascular inflammation and remodeling were assessed (Dörr, O., et al., *Clin Res Cardiol*, 2015, 104: 175-184). A total of 60 patients (mean age of 67.9±9.6 years) diagnosed with resistant arterial hypertension were treated with percutaneous, catheter-based renal sympathetic denervation. Treatment included RF energy delivery to the renal artery using a Symplicity™ catheter system commercially available from Medtronic, Inc. In this human trial, a therapeutic response was defined as a systolic blood pressure (BP) reduction of >10 mmHg in the office blood pressure measurement 6 months after renal denervation. Of the 60 patients, 49 patients (82%) were classified as responders with a mean systolic BP reduction of >10 mmHg. Venous blood samples for determination of biomarkers of inflammation (e.g., IL-6, high-sensitive C-reactive protein (hsCRP)) and markers of vascular remodeling (matrix metalloproteinases (MMP-2 and MMP-9), tissue inhibitors of matrix metalloproteinases (TIMP-1)) were collected at baseline (prior to renal denervation) and 6 months after renal denervation for all patients.

Collected data from all patients demonstrated that bilateral renal nerve denervation resulted in a significant reduction in mean office systolic BP of 26.4 mmHg (169.3±11.3 mmHg at baseline vs. 142.9±13.8 mmHg at follow-up; p<0.001). The procedure further resulted in a significant reduction in the serum levels of hsCRP (3.6 mg/dL at baseline vs. 1.7 mg/dL at follow-up, p<0.001), and a significant reduction in the pro-inflammatory cytokine IL-6 (4.04 pg/mL at baseline vs. 2.2 pg/mL at follow-up, p<0.001) six months after treatment. Additionally, the procedure resulted in a significant increase in the serum levels of MMP-9 (425.2 ng/mL at base line vs. 574.1 ng/mL at follow-up, p=0.02), and in serum levels of MMP-2 (192.3 ng/mL at baseline vs. 231.3 ng/mL at follow-up, p<0.001). There were no significant changes in TIMP-1-6 months after renal denervation. Notably, of non-responders (e.g., patients with a BP reduction of <10 mmHg), serum levels of hsCRP still decreased (3.2 mg/dL at baseline vs. 2.4 mg/dL at follow-up, p=0.09), and serum levels of IL-6 still decreased (3.1 pg/mL at baseline vs. 2.7 pg/mL at follow-up, p=0.16), although there was a significantly greater beneficial effect of renal denervation on biomarker levels in BP responders when compared with non-responders.

These findings suggest that catheter-based renal neuromodulation exhibits a positive vascular and systemic effect on mediators of inflammation, IL-6 and hsCRP, and inhibitors (MMP-9 and MMP-2) of deleterious cardiovascular remodeling. Low serum levels of MMP-9 and MMP-2 have been found to be essential to damaging vascular remodeling found in essential hypertension and progression of end-organ damage These findings suggest that levels of MMP-9 and MMP-2, which are involved in ECM turnover in different tissues, including the arterial wall, can be elevated post-renal neuromodulation, and, without being bound by theory, are postulated to be beneficial in reversal of damage to the vessels caused by inflammation, cardiovascular disease and/or hypertension. As elevated inflammatory biomarkers, such as IL-6 and CRP, have been proposed as predictors and possible contributors of sleep disorder etiology and/or incidence of a sleep disorder, these results demonstrate that renal neuromodulation may be useful to reduce a severity of a sleep disorder, reverse a sleep disorder diagnosis, or reduce a risk associated with the development of a sleep disorder in susceptible or at risk patients. In addition to lowering systolic BP in (responsive) hypertensive patients, these findings suggest that renal denervation has a positive effect on biomarkers of inflammation (e.g., IL-6, hsCRP) and cardiovascular remodeling (e.g., MMP-2, MMP-9) separate from and in addition to the effect on blood pressure.

Example 5

Example 5 describes an example of the effects of renal neuromodulation on nocturnal blood pressure using ambulatory 24-hour blood pressure (BP) monitoring in human patients. Elevated blood pressure during the nighttime as well as early morning hours (e.g., elevated morning surge in BP; "MSBP") is associated with an increased risk of cardiovascular events and strokes, and MSBP is associated with sleep disorders independent from "non-dipping" nocturnal blood pressure, with higher morning surges associated with higher levels of sleep disturbance symptoms, including poorer overall sleep quality (FitzGerald, L., et al., *J Hum Hypertens,* 2012, 26: 228-235; Kario, K., et al., *Hypertension,* 2015, 66:1130-1137; Kario, K. and Hamasaki, H., *J Clin Hypertens,* 2015, 17: 682-685). In this example, a total of 576 patients diagnosed with resistant arterial hypertension (e.g., baseline office systolic BP≥160 mm Hg and 24-hour ambulatory systolic BP≥135 mm Hg) were either treated ("RDN treated"; n=382) with bilateral percutaneous, catheter-based renal sympathetic denervation (mean age of 58±11 years) or blindly treated ("blind control"; n=159) with a sham procedure (e.g., renal angiogram) or not treated ("control"; n=19) (Kario, K., et al., *Hypertension,* 2015, 66:1130-1137). Treatment included RF energy delivery to the renal artery using a Symplicity™ catheter system (Medtronic, Inc.). The renal neuromodulation ("RDN") treated group received up to six ablations rotated in 45 degree increments and approximately 5 mm apart for 2 minutes each in both renal arteries. Treatments were delivered from the first distal main renal artery bifurcation to the ostium proximally and were spaced longitudinally and rotationally under fluoroscopic guidance. BP variability, morning ambulatory, nighttime ambulatory and daytime ambulatory systolic BP was measured by 24-hour ambulatory BP monitoring before renal denervation and at 6 months after renal denervation.

In patients with resistant hypertension, renal denervation resulted in significant reduction in ambulatory nighttime and morning BP. For example, mean ambulatory nighttime BP measurements in the RDN treated group were reduced by 6.3±18.2 mm Hg (p<0.001; baseline of 151.5±18.3 mm Hg, p=0.24), whereas they were not significantly reduced (−1.7±19.2 mm Hg; p=0.233) from baseline (149.5±20.1 mm Hg, p=0.24) in the blind control+control group 6 months post-neuromodulation. Further, mean ambulatory morning BP measurements in the RDN treated group were reduced by 7.3±19.6 mm Hg (p<0.001; baseline of 161.2±17.2 mm Hg, p=0.24), whereas they were not significantly reduced (−3.2±21.0 mm Hg; p=0.046) from baseline (160.3±19.2 mm Hg, p=0.579) in the blind control+control group 6 months post-neuromodulation. These findings suggest that patients presenting with a sleep disorder and treated with renal neuromodulation will have decreased ambulatory nighttime systolic BP and decreased MSBP which will reduce the patient's likelihood (e.g., lower level of risk) of developing, progressing or worsening cardiovascular disease. These findings further suggest that patients with a sleep disorder and treated with renal neuromodulation will improve one or more symptoms relating to the sleep disorder.

Example 6

Example 6 describes a method for treating human patients diagnosed with a sleep disorder with renal neuromodulation and anticipated outcomes of such treatment. In this example, human patients diagnosed with a sleep disorder will be treated with renal denervation and a method of treatment includes modulating nerve tissue surrounding the main renal artery (e.g., locations along the main renal vessel, locations at or near the bifurcation, etc.) and/or modulating nerve tissue surrounding one or more primary branch trunks (e.g., proximal portion of one or more primary branch vessels distal to the bifurcation).

For patients undergoing distal main renal artery treatment, modulating nerve tissue includes forming a plurality of spaced-apart lesions at the distal segment of the renal artery and within a distance of approximately 6 mm proximal to the branch point within the renal artery using the Symplicity Spyral™ catheter, commercially available from Medtronic, Inc. For example, a first (e.g., most distal) lesion can be formed about 5-6 mm proximal from the bifurcation. Other multi-electrode, spiral/helical-shaped catheters for forming multiple lesions along the length of the vessel are also contemplated for these methods. For patients undergoing main artery treatment at a central segment of the main renal artery, the Symplicity Spyral™ catheter can be used to form a plurality of spaced-apart lesions (e.g., about 2 lesions to about 4 lesions) in a spiral/helical pattern along the central segment of the main renal artery. The catheter may also be moved proximally and/or distally to form multiple sets of lesions during a procedure.

For patients undergoing renal branch treatment, modulating nerve tissue includes forming up to about four lesions (e.g., about 2 lesions to about 4 lesions) in one or more primary branch trunks (e.g., from about 1 mm to about 6 mm distal to the primary bifurcation, in regions greater than 2 mm distal to the primary bifurcation). Modulation of nerve tissue at branch trunk treatment sites and/or different combinations of treatment sites within the renal vasculature (e.g., locations along the main renal vessel, locations at or near the bifurcation, etc.) can also be performed using the multi-electrode Symplicity Spyral™ catheter. Other multi-electrode, spiral/helical-shaped catheters having a tighter spiral/helix (e.g., smaller pitch) for forming multiple lesions close in proximity along the length of the vessel are contemplated for these methods.

In a particular example, a method for efficaciously neuromodulating renal nerve tissue in a human patient can include advancing a multi-electrode Symplicity Spyral™ catheter to a first renal artery branch vessel approximately 6 mm distal to the bifurcation. Following retraction of a guidewire and/or straightening sheath, the Symplicity Spyral™ catheter can transform to a spiral/helically-shaped configuration that accommodates the inner diameter of a typical renal artery and/or the branches of the renal artery (e.g., about 2-10 mm), placing the electrodes (e.g., 4 electrodes) in contact with the vessel wall. A first (e.g., most distal) lesion can be formed about 5-6 mm distal to the bifurcation. Following treatment at the first renal artery branch, the catheter can be withdrawn into the main renal vessel and then advanced under fluoroscopy into a second renal artery branch and the treatment procedure can be repeated. Some methods can include treating two branch vessels at the proximal trunk segment of the branch vessel. Other methods can include treating greater than two or all of the primary branch vessels branching from the main renal vessel (e.g., distal to a primary bifurcation). As described above, these methods may also include combining neuromodulation of renal nerve tissue surrounding one or more primary branch trunks with neuromodulation of renal nerve tissue at additional treatment locations (e.g., locations along the main renal vessel, locations at or near the bifurcation, etc.). Other methods can include advancing a multi-electrode Symplicity Spyral™ catheter to a first renal artery branch vessel approximately 10 mm distal to the bifurcation, with a first (e.g., most distal) lesion formed about 9-10 mm distal to the bifurcation.

Physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient diagnosed with a sleep disorder or having an increased risk of developing a sleep disorder (e.g., a predisposition, having one or more biomarkers suggesting an increased likelihood, genetic/epigenetic factors, etc.) or having one or more measurable risk factors predictive for the development of a sleep disorder, with renal neuromodulation, at one or more of the described treatment locations, will inhibit sympathetic neural activity in the renal nerve in a manner that reduces a central sympathetic drive (e.g., as correlated with whole body norepinephrine spillover and/or renal norepinephrine spillover) by greater than about 20%, about 30%, about 40%, about 50% or greater than about 60% in about 1 month, in about 3 months, in about 6 months or in about 12 months, or in another embodiment, in about 3 months to about 12 months, after renal neuromodulation treatment. Reduction in central sympathetic drive is anticipated to result in a therapeutically beneficial improvement in one or more measurable physiological parameters corresponding to an incidence of a sleep disorder, and/or a severity of a sleep disorder in the patient.

Example 7

Example 7 describes a method for determining human patients who have a calculated risk score for determining a sleep disorder status (e.g., diagnosis) at or above a threshold sleep disorder risk score and treating such patients with targeted sympathetic neuromodulation of renal SNS neural fibers innervating the kidney. In this example, human patients having a calculated sleep disorder risk score meeting or exceeding a threshold sleep disorder risk score will be treated with renal neuromodulation to improve the patient's sleep disorder risk score and/or lower the patient's sleep disorder risk score (e.g., in a manner that improves the patient's sleep disorder status, reverses the patient's sleep disorder diagnosis, and/or improves one or more symptoms or contributing factors associated with the sleep disorder in the patient).

Patients presenting one or more risk factors or indicators predictive for or indicative of a sleep disorder will be assessed for other possible risk factors and a sleep disorder risk score will be calculated. In this example, a patient will fill out a questionnaire or otherwise have an attending physician assess risk factors. A sleep disorder risk score calculator based on risk factor data to determine a probability or likelihood of sleep disorder status (e.g., diagnosis) in an individual is shown in FIG. 9. The sleep disorder risk score calculator shown in FIG. 9 is derived from data provided in the PSQI study to develop a model of a technique to assess duration and/or frequency of sleep dysfunction-associated symptoms and screen the patient for risk factors and indicators of a sleep disorder to determine a likelihood and/or severity of a sleep disorder diagnosis (Buysse, D. J., et al., *Psychiatry Res*, 1989, 28: 193-213).

Referring to the sleep disorder risk score calculator shown in FIG. 9, a patient will be queried and assessed for core sleep disorder symptoms (e.g., difficulty in falling asleep, waking in the middle of the night or early morning, waking to use the bathroom, snoring and/or coughing, unable to breath comfortably, too cold or hot, experiencing bad dreams, experiencing pain, needing medication to fall asleep, difficulty staying awake during the day, experiencing difficulty in maintaining enthusiasm in activities or hobbies, etc.). In addition to these twelve clinical measures, the patient may also be examined and/or tested by a physician for determination of other physiological variables pertaining to the SNS such as, for example, heart rate variability, heart rate reactions to stress, whole body MSNA levels (FIG. 9), and systolic blood pressure (e.g., daytime, nocturnal and morning surge) (not shown in FIG. 9). In this example, the input to the calculator will yield both a patient-specific sleep disorder risk score as well as an indication as to whether RDN treatment is recommended. In this example, the threshold sleep disorder risk score is 11. An indication of RDN recommendation may be based on whether the patient's sleep disorder risk score is at or above the threshold sleep disorder risk score, either alone or in combination with one or more physician-administered tests assessing SNS activity or systolic blood pressure level.

As illustrated in FIG. 9, a hypothetical patient reports experiencing 1 sleep disorder inventory symptom three or more times a week, 4 sleep disorder inventory symptoms once or twice a week, 4 sleep disorder inventory symptoms less than once a week, and indicated that 4 sleep disorder inventory symptoms were not experienced (e.g., over the past month). The hypothetical patient further rated their sleep quality as fairly bad over the past month. A physician-administered SNS test assessing heart rate variability indicated the patient's SDNN intervals were less than the 50 ms threshold, and a test for baroreflex indicated that the baroreceptor sensitivity was less than 1.74 ms/mmHg; however the patient did not exceed threshold levels in heart rate reactions to stress, and whole body MSNA levels. The hypothetical patient's sleep disorder risk score of 17 exceeds the threshold level determination (e.g., greater than 10) for a sleep disorder diagnosis. In this example, the sleep disorder risk score together with meeting at least one SNS threshold, qualifies the hypothetical patient as a candidate for receiving RDN treatment. In another example, the hypothetical patient is a candidate for receiving RDN treatment with or without the additional SNS tests (or ascertaining a systolic blood pressure for the patient). Following bilateral renal neuromodulation treatment, the hypothetical patient may have improvement in one or more measurable risk factors (e.g., heart rate variability, severity or frequency of sleep disturbances, nocturnal and/or morning surge blood pressure, etc.), and/or reported risk factors pertaining to core sleep-disorder symptoms (e.g., difficulty in falling asleep, waking in the middle of the night or early morning, waking to use the bathroom, snoring and/or coughing, unable to breath comfortably, too cold or hot, experiencing bad dreams, experiencing pain, needing medication to fall asleep, feeling sad, feeling nervous or anxious, experiencing restless legs before or during sleep, difficulty staying awake during the day, experiencing difficulty in maintaining enthusiasm in activities or hobbies, etc.), that improves the patient's sleep disorder risk score, and in some cases, to levels below the threshold sleep disorder risk score level(s).

VIII. FURTHER EXAMPLES

1. In a normotensive patient diagnosed with a sleep disorder, a method comprising:
   intravascularly positioning a neuromodulation assembly within a renal blood vessel of the patient and adjacent to a renal nerve of the patient; and
   at least partially inhibiting sympathetic neural activity in the renal nerve of the patient via the neuromodulation assembly,
   wherein at least partially inhibiting sympathetic neural activity results in a therapeutically beneficial improvement in a measurable parameter associated with the sleep disorder of the patient.

2. The method of example 1 wherein at least partially inhibiting sympathetic neural activity in the patient in a manner that results in a therapeutically beneficial improvement in a measurable parameter associated with the sleep disorder comprises one or more of improving a sleep pattern of the patient, improving a sleep quality of the patient, and reducing a level of insomnia in the patient.

3. The method of example 1 or example 2 wherein the patient is diagnosed with one or more of insomnia, hypersomnia, circadian rhythm disorder, movement disorder, and parasomnia.

4. The method of any one of examples 1-3 wherein reducing sympathetic neural activity in the patient in a manner that results in a therapeutically beneficial improvement in a measurable parameter associated with the sleep disorder comprises reducing a morning surge blood pressure and/or a nocturnal blood pressure in the patient.

5. The method of one of examples 1-4 wherein reducing sympathetic neural activity in the patient in a manner that results in a therapeutically beneficial improvement in a measurable parameter associated with the sleep disorder comprises improving one or more of a difficulty in getting to sleep, the number of times the patient wakes up during the night or early morning, the amount of snoring, the number of bad dreams or night terrors, the number of times a patient takes medication to fall asleep, or the level of fatigue during waking hours as measured on a sleep quality screening tool.

6. The method of any one of examples 1-5 wherein reducing sympathetic neural activity in the patient further comprises improving one or more sleep dysfunction-associated symptoms in the patient as reported on a sleep quality screening tool.

7. The method of example 6 wherein improving one or more sleep dysfunction-associated symptoms in the patient includes reducing a level of sleep dysfunction-associated symptoms and/or a number of sleep dysfunction-associated symptoms.

8. The method of example 6 or example 7 wherein improving one or more sleep dysfunction-associated symptoms in the patient includes reducing a level of sleep dysfunction-associated symptoms in the patient by at least about 5%, at least about 10%, at least about 20% or at least about 40%.

9. The method of example 6 or example 7 wherein improving one or more sleep dysfunction-associated symptoms in the patient includes reducing a number of sleep dysfunction-associated symptoms in the patient by at least about 5%, at least about 10%, at least about 20% or at least about 40% within about three months to about 12 months after at least partially inhibiting sympathetic neural activity in the patient by delivering energy to the renal nerve.

10. The method of any one of examples 1-9 wherein the patient is further diagnosed with depression or an anxiety disorder.

11. The method of any one of examples 1-10 wherein the patient is between the ages of 18 and 45, between the ages of 18 and 30, between the ages of 20 and 40, or between the ages of 20 and 35.

12. The method of any one of examples 1-10 wherein the patient is between the ages of 35 and 65, between the ages of 45 and 65, between the ages of 50 and 70, or the patient is at least 35 years old.

13. The method of any one of examples 1-12 wherein at least partially inhibiting sympathetic neural activity in the patient further comprises reducing an incidence of stroke, cardiovascular disease, hypertension, a metabolic disorder, obesity, dementia, chronic kidney disease, osteoporosis or infertility in the patient.

14. The method of any one of examples 1-12 wherein the patient has a history of cardiovascular disease or stroke, and wherein at least partially inhibiting sympathetic neural activity in the patient further comprises reducing an incidence of a future cardiovascular event or stroke.

15. The method of example 1 wherein at least partially inhibiting sympathetic neural activity in the patient in a manner that results in a therapeutically beneficial improvement in a measurable parameter associated with the sleep disorder comprises improving a patient's sleep disorder risk score on a sleep quality screening tool.

16. The method of any one of examples 1-15 wherein at least partially inhibiting sympathetic neural activity in the patient in a manner that results in a therapeutically beneficial improvement in a measurable parameter associated with the sleep disorder includes one or more of:
   increasing a heart rate variability of the patient;
   increasing baroreceptor sensitivity in the patient;
   reducing a morning surge blood pressure in the patient;
   reducing a plasma cortisol level in the patient;
   reducing a level of glucocorticoid resistance in the patient; and
   reducing a level of an inflammatory biomarker in the patient.

17. The method of example 16 wherein the inflammatory biomarker is at least one of interleukin-6, interleukin-8, tumor necrosis factor-alpha, and C-reactive protein.

18. The method of any one of examples 1-17 wherein the patient is diagnosed with a non-apnea sleep disorder.

19. The method of any one of examples 1-18 wherein reducing sympathetic neural activity in the renal nerve further reduces at least one of whole body norepinephrine spillover in the patient or muscle sympathetic nerve activity (MSNA) in the patient.

20. The method of example 19 wherein the whole body norepinephrine spillover is reduced by at least about 20% in about one month or reduced by greater than about 40% in about three months to about 12 months after reducing sympathetic neural activity in the renal nerve.

21. The method of example 1, further comprising delivering energy to renal perivascular adipose tissue adjacent to the renal blood vessel of the patient via the neuromodulation assembly to reduce norepinephrine spillover to plasma.

22. The method of any one of examples 1-21 wherein the patient is currently administered one or more pharmaceutical drugs for the sleep disorder, and wherein at least partially inhibiting sympathetic neural activity in the patient in a manner that results in a therapeutically beneficial improvement in a measurable parameter associated with the sleep disorder comprises reducing at least one of a number of or a measured dosage of pharmaceutical drugs administered to the patient for the sleep disorder.

23. The method of example 22 wherein the pharmaceutical drugs include one or more of an anti-anxiety drug, antidepressant, an anti-psychotic drug, an insomnia drug or an anti-inflammatory drug.

24. In a human patient, a method of reducing a risk of the patient developing a sleep disorder, the method comprising:
   intravascularly positioning a catheter carrying a neuromodulation assembly adjacent to a renal sympathetic nerve of the patient;
   delivering energy to the renal sympathetic nerve via the neuromodulation assembly to attenuate neural traffic along the renal sympathetic nerve; and
   removing the catheter and neuromodulation assembly from the patient after treatment,
   wherein attenuating neural traffic along the renal sympathetic nerve reduces a risk of the patient developing the sleep disorder.

25. The method of example 24 wherein the risk of developing the sleep disorder is calculated using a sleep quality screening tool, and wherein a post-neuromodulation sleep disorder risk score for the patient, as calculated by the sleep quality screening tool, is lower than an initial sleep disorder risk score.

26. The method of example 24 or example 25 wherein attenuating neural traffic along the renal sympathetic nerve further results in one or more of:
   increasing heart rate variability in the patient;
   increasing baroreceptor sensitivity in the patient;
   reducing a level of glucocorticoid resistance in the patient;
   reducing a cortisol level in the patient;
   reducing a systolic blood pressure of the patient;
   reducing a morning surge blood pressure in the patient;
   reducing a nocturnal blood pressure in the patient;
   reducing muscle sympathetic nerve activity (MSNA) in the patient;
   reducing a plasma or urine norepinephrine level in the patient; and
   reducing a level of an inflammatory biomarker in the patient.

27. The method of example 26 wherein the inflammatory biomarker is at least one of interleukin-6, interleukin-8, tumor necrosis factor-alpha, and C-reactive protein.

28. The method of any one of examples 24-27 wherein the patient has a personal or family history of sleep disorders, anxiety disorders and/or depression, and wherein attenuating neural traffic along the renal sympathetic nerve reduces an incidence of a future sleep disorder in the patient.

29. The method of any one of examples 24-28 wherein the patient is currently experiencing an adverse life circumstance and is diagnosed with one or more of low heart rate variability, elevated plasma or urine catecholamine levels, elevated systolic blood pressure, elevated morning surge in blood pressure, non-dipping nocturnal blood pressure, low neuropeptide Y level, elevated plasma cortisol level, glucocorticoid resistance, elevated cortisol awakening rise (CAR), reduced baroreceptor sensitivity, and elevated level of an inflammatory biomarker.

30. The method of any one of examples 24-29 wherein the patient has a polymorphism in at least one of the genes encoding for FK506-binding protein 5 (FKBP5 gene), glucocorticoid receptor (NR3C1 gene), cortisol releasing hormone receptor-1 (CRHR1 gene), and tumor necrosis factor (TNF)-alpha, that provide an increased likelihood of developing the sleep disorder.

31. The method of any one of examples 24-30 wherein the patient is diagnosed with cardiovascular disease.

32. The method of any one of examples 24-31 wherein the patient has a history of stroke.

33. The method of any of examples 24-32 wherein the patient has one or more sleep disorder risk factors selected from the group consisting of increased substance abuse, hypertension, elevated norepinephrine whole body spillover, exposure to multiple traumatic events, prior traumatic brain injury, family history of mental disorder, and adverse childhood experience.

34. The method of any one of examples 24-33 wherein attenuating neural traffic along the renal sympathetic nerve comprises at least partially ablating the renal sympathetic nerve.

35. The method of any one of examples 24-33 wherein attenuating neural traffic along the renal sympathetic nerve comprises at least partially disrupting communication along the renal sympathetic nerve.

36. The method of any one of examples 24-33 wherein attenuating neural traffic along the renal sympathetic nerve comprises irreversibly disrupting communication along the renal sympathetic nerve.

37. The method of any one of examples 24-33 wherein attenuating neural traffic along the renal sympathetic nerve comprises delivering an energy field to the renal sympathetic nerve via the neuromodulation assembly.

38. The method of example 37 wherein delivering an energy field to the renal sympathetic nerve comprises delivering at least one of radio frequency energy, ultrasound energy, high intensity ultrasound energy, laser energy, and microwave energy via the neuromodulation assembly.

39. The method of any one of examples 24-38 wherein the patient is diagnosed with prehypertension or hypertension, and wherein attenuating neural traffic along the renal sympathetic nerve further reduces whole body norepinephrine spillover in the patient in a manner that reduces the risk of the patient developing the sleep disorder.

40. A method for improving a patient's risk score corresponding to a sleep disorder status of the patient, the method comprising:
   intravascularly positioning a catheter carrying a neuromodulation assembly within a renal blood vessel and adjacent to a renal sympathetic nerve in the patient;
   delivering energy to the renal sympathetic nerve via the neuromodulation assembly to attenuate neural traffic along the renal sympathetic nerve; and removing the catheter and neuromodulation assembly from the patient after treatment, wherein attenuating neural traffic along the renal sympathetic nerve results in improving the patient's risk score corresponding to the sleep disorder status of the patient.

41. The method of example 40 wherein improving the patient's risk score corresponding to the sleep disorder status of the patient includes one or more of improving sleep dysfunction-associated symptoms, improving the patient's sleep quality, reducing a level of systemic inflammation in the patient, and improving a patient's body mass index.

42. The method of example 40 or example 41 wherein the patient is diagnosed with pre-hypertension or hypertension, and wherein improving the patient's risk score corresponding to the sleep disorder status of the patient includes reducing the patient's blood pressure.

43. The method of any one of examples 40-42 wherein a patient's risk score corresponding to the sleep disorder status of the patient is reduced by at least about 10%, at least about 15%, at least about 20%, at least about 30% or at least about 40%.

44. The method of any one of examples 40-43 wherein the patient's risk score is calculated using a sleep quality screening tool, and wherein a post-neuromodulation sleep disorder risk score, as calculated by the sleep quality screening tool, is lower than an initial sleep disorder risk score.

45. The method of example 44, wherein the sleep quality screening tool includes a polysomnography for assessing a sleep disorder severity.

46. A method for improving a sleep disorder risk score for a human patient diagnosed with a sleep disorder, the method comprising performing a renal neuromodulation procedure in the patient diagnosed with the sleep disorder, wherein a post-neuromodulation risk score is lower than an initial risk score of the patient diagnosed with the sleep disorder.

47. The method of example 46 wherein the post-neuromodulation risk score is lower than the initial risk score by about 5%, about 10%, about 20% or about 30%.

48. The method of example 46 or example 47 wherein the initial risk score indicates the patient is at risk of having the sleep disorder if the initial risk score is greater than a threshold risk score.

49. The method of any one of examples 46-48 wherein the initial risk score and the post-neuromodulation risk score are determined using a sleep quality screening tool for determining a severity of the sleep disorder of the patient.

50. The method of any one of examples 46-49 wherein the initial risk score and the post-neuromodulation risk score are based upon one or more factors comprising a psychological evaluation, type and/or severity of sleep dysfunction-associated symptoms, duration of sleep dysfunction-associated symptoms experienced by the patient, number of instances of trauma exposure, and symptoms associated with a mood disorder.

51. A method for managing a non-apnea sleep disorder in a human patient, the method comprising:
　　translumially positioning an energy delivery element of a catheter within a renal blood vessel of the patient and adjacent to renal sympathetic neural fibers in the patient; and
　　at least partially ablating the renal sympathetic neural fibers via the energy delivery element,
　　wherein at least partially ablating the renal sympathetic neural fibers results in a therapeutically beneficial improvement in a measurable parameter associated with the sleep disorder of the patient.

52. The method of example 51 wherein at least partially ablating the renal sympathetic neural fibers in the patient in a manner that results in a therapeutically beneficial improvement in a measurable parameter associated with the sleep disorder comprises improving one or both of a sleep pattern or a sleep quality.

53. The method of example 51 or 52 wherein at least partially ablating the renal sympathetic neural fibers in the patient in a manner that results in a therapeutically beneficial improvement in a measurable parameter associated with the sleep disorder comprises at least one of reducing a nocturnal blood pressure and reducing a morning surge in blood pressure in the patient.

54. The method of any one of examples 51-53 wherein at least partially ablating the renal sympathetic neural fibers in the patient in a manner that results in a therapeutically beneficial improvement in a measurable parameter associated with the sleep disorder comprises improving one or more sleep dysfunction-associated symptoms in the patient.

55. The method of any one of examples 51-54 wherein at least partially ablating the renal sympathetic neural fibers further results in reducing an incidence of one or more of hypertension, cardiovascular disease, obesity, diabetes, insulin resistance, systemic inflammation, kidney disease, stroke, dementia, osteoporosis and infertility in the patient.

56. The method of any one of examples 51-55 wherein at least partially ablating the renal sympathetic neural fibers further results in a therapeutically beneficial improvement in a measurable physiological parameter associated with a comorbid condition in the patient.

57. The method of example 56 wherein the comorbid condition is one or more of depression, anxiety disorder, cancer, cardiovascular disease, obesity, metabolic disorder, systemic inflammation, dementia and infertility.

58. The method of any one of examples 51-57, further comprising administering one or more pharmaceutical drugs to the patient, wherein the pharmaceutical drugs are selected from the group consisting of anti-insomnia drugs, anti-anxiety drugs, antidepressants, anti-hypertension drugs and anti-inflammatory drugs.

59. The method of any one of examples 51-58 wherein at least partially ablating the renal sympathetic neural fibers of the patient via the energy delivery element comprises delivering a thermal electric field to the sympathetic neural fibers via at least one electrode.

60. A method for treating a patient that can answer affirmatively, if asked, to at least two of the following statements:
　　in the past three months and at least most of the time—
　　　　a) you cannot get to sleep within 30 minutes,
　　　　b) you wake up in the middle of the night or early morning,
　　　　c) you cannot breathe comfortably while sleeping,
　　　　d) you snore or cough loudly while sleeping,
　　　　e) you have bad dreams,
　　　　f) you experience restless legs before or during sleep,
　　　　g) you have difficulty staying awake during the day,
　　the method comprising:
　　　　intravascularly positioning a neuromodulation assembly within a renal blood vessel of the patient and adjacent to a renal nerve of the patient; and
　　　　at least partially inhibiting sympathetic neural activity in the renal nerve of the patient via the neuromodulation assembly, wherein at least partially inhibiting sympathetic neural activity results in a therapeutically beneficial improvement in the patient's response to one or more of statements a-g.

IX. CONCLUSION

The above detailed descriptions of embodiments of the technology and methodology are not intended to be exhaustive or to limit the technology to the precise forms disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. In a human patient, a method of reducing a risk of the patient developing a sleep disorder, the method comprising:
    determining an initial risk score of the human patient developing the sleep disorder, wherein the sleep disorder comprises one or more of insomnia, hypersomnia, a circadian rhythm disorder, a movement disorder, parasomnia, or a non-apnea sleep disorder;
    intravascularly positioning a catheter carrying a neuromodulation assembly adjacent to a renal sympathetic nerve of the patient;
    delivering energy to the renal sympathetic nerve via the neuromodulation assembly to attenuate neural traffic along the renal sympathetic nerve;
    removing the catheter and the neuromodulation assembly from the patient after treatment; and
    determining a post-neuromodulation risk score of the human patient developing the sleep disorder,
    wherein attenuating neural traffic along the renal sympathetic nerve reduces the risk of the patient developing the sleep disorder.

2. The method of claim 1 wherein the initial risk score of developing the sleep disorder and the post-neuromodulation risk score are calculated using a sleep quality screening tool.

3. The method of claim 1 wherein the patient has one or more sleep disorder risk factors selected from the group consisting of hypertension, elevated norepinephrine whole body spillover, cardiovascular disease, prior incidence of stroke, and prior traumatic brain injury.

4. The method of claim 1 wherein the patient has a personal or family history of sleep disorders, anxiety disorders and/or depression, and wherein attenuating neural traffic along the renal sympathetic nerve reduces an incidence of a future sleep disorder in the patient.

5. The method of claim 1 wherein the patient is currently experiencing an adverse life circumstance and is diagnosed with one or more of low heart rate variability, elevated plasma or urine catecholamine levels, elevated systolic blood pressure, elevated morning surge in blood pressure, non-dipping nocturnal blood pressure, low neuropeptide Y level, elevated plasma cortisol level, glucocorticoid resistance, elevated cortisol awakening rise (CAR), reduced baroreceptor sensitivity, or an elevated level of an inflammatory biomarker.

6. The method of claim 1 wherein the patient has a polymorphism in at least one of the genes encoding for FK506-binding protein 5 (FKBP5 gene), glucocorticoid receptor (NR3C1 gene), cortisol releasing hormone receptor-1 (CRHR1 gene), and tumor necrosis factor (TNF)-alpha, that provide an increased likelihood of developing the sleep disorder.

7. A method for improving a patient's risk score corresponding to a sleep disorder status of the patient, the method comprising:
    determining an initial risk score of the patient developing the sleep disorder, wherein the sleep disorder comprises one or more of insomnia, hypersomnia, a circadian rhythm disorder, a movement disorder, parasomnia, or a non-apnea sleep disorder;
    intravascularly positioning a catheter carrying a neuromodulation assembly within a renal blood vessel and adjacent to a renal sympathetic nerve in the patient;
    delivering energy to the renal sympathetic nerve via the neuromodulation assembly to attenuate neural traffic along the renal sympathetic nerve;
    removing the catheter and the neuromodulation assembly from the patient after treatment;
    determining a post-neuromodulation risk score of the patient developing the sleep disorder; and
    comparing the post-neuromodulation risk score to the initial risk score,
    wherein attenuating neural traffic along the renal sympathetic nerve results in improving the post-neuromodulation risk score relative to the initial risk score.

8. The method of claim 7 wherein the initial risk score and the post-neuromodulation risk score are calculated using a sleep quality screening tool.

9. The method of claim 7 wherein the initial risk score and the post-neuromodulation risk score are based upon one or more factors comprising a psychological evaluation, type and/or severity of sleep dysfunction-associated symptoms, duration of sleep dysfunction-associated symptoms experienced by the patient, number of instances of trauma exposure, or symptoms associated with a mood disorder.

10. The method of claim 7 wherein improving the post-neuromodulation risk score relative to the initial risk score includes one or more of improving sleep dysfunction-associated symptoms, improving the patient's sleep quality, reducing a level of systemic inflammation in the patient, or improving a patient's body mass index.

11. In a normotensive patient diagnosed with a sleep disorder, a method comprising:
intravascularly positioning a neuromodulation assembly within a renal blood vessel of the patient and adjacent to a renal nerve of the patient, wherein the sleep disorder comprises one or more of insomnia, hypersomnia, a circadian rhythm disorder, a movement disorder, parasomnia, or a non-apnea sleep disorder; and
at least partially inhibiting sympathetic neural activity in the renal nerve of the patient via the neuromodulation assembly,
wherein at least partially inhibiting sympathetic neural activity results in a therapeutically beneficial improvement in a measurable parameter associated with the sleep disorder of the patient.

12. The method of claim 11 wherein reducing sympathetic neural activity in the patient in the manner that results in the therapeutically beneficial improvement in the measurable parameter associated with the sleep disorder comprises improving one or more of a difficulty in getting to sleep, the number of times the patient wakes up during the night or early morning, the amount of snoring, the number of bad dreams or night terrors, the number of times a patient takes medication to fall asleep, or the level of fatigue during waking hours as measured on a sleep quality screening tool.

13. The method of claim 11 wherein reducing sympathetic neural activity in the patient in the manner that results in the therapeutically beneficial improvement in the measurable parameter associated with the sleep disorder comprises reducing a level of sleep-related symptoms and/or a number of sleep-related symptoms.

14. The method of claim 11 wherein the patient is between the ages of 18 and 45, between the ages of 18 and 30, between the ages of 20 and 40, between the ages of 20 and 35, between the ages of 35 and 65, between the ages of 45 and 65, between the ages of 50 and 70, or the patient is at least 35 years old.

15. The method of claim 11 wherein at least partially inhibiting sympathetic neural activity in the patient further comprises reducing an incidence of stroke, cardiovascular disease, hypertension, a metabolic disorder, obesity, dementia, chronic kidney disease, osteoporosis or infertility in the patient.

16. The method of claim 11 wherein the patient has a history of cardiovascular disease or stroke, and wherein at least partially inhibiting sympathetic neural activity in the patient further comprises reducing an incidence of a future cardiovascular event or stroke.

17. The method of claim 11 wherein a post-neuromodulation condition of the parameter associated with the sleep disorder is improved compared to a baseline condition of the parameter, and wherein the baseline condition and the post-neuromodulation condition are determined using a sleep quality screening tool for determining a severity of the sleep disorder of the patient.

18. The method of claim 11 wherein at least partially inhibiting sympathetic neural activity in the patient in a manner that results in the therapeutically beneficial improvement in the measurable parameter associated with the sleep disorder includes one or more of:
improving a sleep pattern of the patient;
improving a sleep quality of the patient;
reducing a level of insomnia in the patient;
reducing a morning surge blood pressure in the patient;
reducing a nocturnal blood pressure in the patient;
increasing a heart rate variability of the patient;
increasing baroreceptor sensitivity in the patient;
reducing a plasma cortisol level in the patient;
reducing a level of glucocorticoid resistance in the patient; or
reducing a level of an inflammatory biomarker in the patient.

\* \* \* \* \*